United States Patent [19]

Thøgersen et al.

[11] Patent Number: 5,739,281
[45] Date of Patent: Apr. 14, 1998

[54] INTERATIVE METHOD OF AT LEAST THREE CYCLES FOR THE REFOLDING OF PROTEINS

[75] Inventors: Hans Christian Thøgersen, Mundelstrup; Thor Las Holtet, Aarhus V; Michael Etzerodt, Hinnerup, all of Denmark

[73] Assignee: Denzyme APS, Aarhus C, Denmark

[21] Appl. No.: 469,486

[22] Filed: Jun. 6, 1995

Related U.S. Application Data

[63] Continuation of Ser. No. 192,060, filed as PCT/GB93/02495, Dec. 3, 1993, abandoned.

[30] Foreign Application Priority Data

Feb. 4, 1993 [DK] Denmark ................... 130/93
Feb. 5, 1993 [DK] Denmark ................... 139/93

[51] Int. Cl.$^6$ ............ C07K 14/00; C07K 14/745; C07K 16/00; C12P 21/00
[52] U.S. Cl. ............ 530/350; 530/402; 530/412; 530/427; 530/384; 530/387.3; 435/183
[58] Field of Search ............ 530/350, 387.3, 530/384, 402, 412, 417, 427, 300; 435/183

[56] References Cited

U.S. PATENT DOCUMENTS

| | | | |
|---|---|---|---|
| 4,444,878 | 4/1984 | Paulus | 435/7.5 |
| 4,656,255 | 4/1987 | Seely | 530/417 |
| 4,999,422 | 3/1991 | Galliher | 530/351 |
| 5,074,977 | 12/1991 | Cheung et al. | 435/7.1 |
| 5,077,392 | 12/1991 | Rudolph et al. | 530/402 |
| 5,231,168 | 7/1993 | Dziegiel et al. | 530/350 |
| 5,284,933 | 2/1994 | Döbeli et al. | 530/413 |
| 5,324,436 | 6/1994 | John et al. | 210/638 |

FOREIGN PATENT DOCUMENTS

| | | |
|---|---|---|
| 0 035 384 A2 | 9/1981 | European Pat. Off. . |
| 0 161 937 A2 | 11/1985 | European Pat. Off. . |
| 0 432 419 A1 | 6/1991 | European Pat. Off. . |
| WO 86/05809 | 10/1986 | WIPO . |

OTHER PUBLICATIONS

Reeck et al., 1987, Homology in Proteins and nucleic acids: a terminology muddle and a way out of it, Cell, 50: 667.

Sleigh, 1993, Antibody–based therapeutics –the third generation, Australasian Biotech., 3: 328–331.

Zhang et al., "Reconstitution of the Diiron Sites in Hemerythrin and Myo–hemerythrin", Biochem. 30: 583–589 (1991).

Katagiri et al, "Bovine endo Thelial cell plasminogen activator inhibitor" Eur. J. Biochem. 176 : 81–87 (1988).

Holliger et al "'Diabodies': Small bivalent and bispecific antibody fragments" PNAS 90: 6444–6448 (Jul. 1993).

Messier et al, Gene 99 : 291–294 (1991) "Cloning and expression in COS–1 cells of a full–length cDNA encoding human coagulation factor X".

Morita et al, "Localization of the Structural Difference between Bovine Blood Coagulation Factors $X_1$ and $X_2$ ...", J. Biol. Chem. 261(9):4008–4014 (Mar. 1986).

Kaul et al "Isolation and characterization of human factor X cDNA" Gene 41 : 311–314 (1986).

Mozhaev et al, Chem Abst. 91:248, abst#119,502; (1979).

Hoffmann et al, "Purification of uis–tagged proteins . . ." Nuc. Acids Res. 19(22): 6337–6338 (1991).

Brey et al, "Dielectric Measurements of Water Sorbed on Ovalbumin and Lysozyme", J. Cell. Interface Sci. 30(1): 13–20 (May 1969).

Buchner, J., et al., "Renaturation, Purification and Characterization of Recombinant $F_{ab}$–Fragments Produced in Escherichia Coli", 1991, Biotechnology, vol. 9, pp. 157–162.

Dalbøge, H., et al., "A Novel Enzymatic Method for Production of Authentic hGH From an Escherichia Coli Produced hGH–Precursor", 1987, Bio/Technology, vol. 5, pp. 161–164.

Fung, M., et al., "Blood Coagulation Factor X mRNA Encodes a Single Polypeptide Chain Containing a Prepro Leader Sequence", 1984, Nucleic Acids Research, vol. 12, pp. 4481–4492.

Jaenicke, R., et al., MRC Lab. of Molec. Biol., Cambridge, UK, "Folding Proteins", 1989, Protein Structure, A Practical Approach, IRL Press, pp. 191–223.

Nagai, K., et al., "Synthesis and Sequence–Specific Proteolysis of Hybrid Proteins Produced in Escherichia Coli", 1987, Methods in Enzymology, vol. 153, pp. 461–481.

Schein, C., "Solubility as a Function of Protein Structure and Solvent Components", 1990, Bio/Technology, vol. 8, pp. 308–317.

Holtet, T.H. et al., Febs Letters, vol. 344, No. 2,3, May 16, 1994, pp. 242–246.

*Primary Examiner*—Stephen Walsh
*Assistant Examiner*—Claire M. Kaufman
*Attorney, Agent, or Firm*—Fish & Richardson P.C.

[57] ABSTRACT

A novel, generally applicable method for producing correctly folded proteins from a mixture of misfolded proteins, e.g. bacterial inclusion-body aggregates. A major new aspect of the method is that over-all efficiency is achieved by subjecting proteins to a time-sequence of multiple denaturation-renaturation cycles, resulting in gradual accumulation of the correctly folded protein. The method has proven efficient for a variety of recombinant proteins. Also provided are novel encrypted recognition sites for bovine coagulation factor $X_a$. The encrypted recognition sites described may be activated in vitro by controlled oxidation or by reversible derivatization of cysteine residues and thereby generate new cleavage sites for factor $X_a$. Two new recombinant serine protease exhibiting narrow substrate specificity for factor $X_a$ recognition sites are also provided. They may replace natural coagulation factor $X_a$ for cleavage of chimeric proteins.

60 Claims, 29 Drawing Sheets

Human β2-microglobulin:

```
      -20                -10                 -1 1                 10
    M S R S V A L A V L A L L S L S G L E A I Q R T P K I Q V Y
                20                 30                 40
    S R H P A E N G K S N F L N C Y V S G F H P S D I E V D L L
                50                 60                 70
    K N G E R I E K V E H S D L S F S K D W S F Y L L Y Y T E F
                80                 90
    T P T E K D E Y A C R V N H V T L S Q P K I V K W D R D M
                                                          SEQ ID NO: 49
```

Fig. 3a

Murine β2-microglobulin:

```
      -20                -10                 -1 1                 10
    M A R S V T L V F L V L V S L T G L Y A I Q K T P Q I Q V Y
                20                 30                 40
    S R H P P E N G K P N I L N C Y V T Q F H P P H I E I Q M L
                50                 60                 70
    K N G K K I P K V E M S D M S F S K D W S F Y I L A H T E F
                80                 90
    T P T E T D T Y A C R V K H D S M A E P K T V Y W D R D M
                                                          SEQ ID NO: 50
```

Fig. 3b

Human Growth Hormone (Somatotropin).

```
     -26                                    -11           4
      M A T G S R T S L L L L A F G L L C L P W L Q E G S A F P T I
                        10                  20                30
      P L S R L F D N A S L R A H R L H Q L A F D T Y Q E F E E A
              40                  50                  60
      Y I P K E Q K Y S F L Q N P Q T S L C F S E S I P T P S N R
              70                  80                  90
      E E T Q Q K S N L E L L R I S L L L I Q S W L E P V Q F L R
              100                 110                 120
      S V F A N S L V Y G A S D S N V Y D L L K D L E E G I Q T L
              130                 140                 150
      M G R L E D G S P R T G Q I F K Q T Y S K F D T N S H N D D
              160                 170                 180
      A L L K N Y G L L Y C F R K D M D K V E T F L R I V Q C R S
              190
      V E G S C G F
```

SEQ ID NO: 51

```
             G  S  I  E  G  R  A  I                C  R  *
    #1       GATCCATCGAGGGTAGGGCTATC ----- TGCCGATA

G  S  I  E  G  R  A  I                K  A  *
    #2       GATCCATCGAGGGTAGGGCTATC ----- AAGGCCTA

G  S  I  E  G  R  A  I                K  K  *
    #3       GATCCATCGAGGGTAGGGCTATC ----- AAGAAGTA
```

```
     M  G  S  H  H  H  H  H  H
    CATATGGGATCGCATCACCATCACCATCACG ----- AGCTTGAATTC
                                    BamHI        HindIII
```

SEQ ID NO: 52
SEQ ID NO: 38

α₂MR:

```
            G  S  I  E  G  R  G  T           L  D  *
    #4      GATCCATCGAGGGTAGGGGCACC  -----  CTGGACTA
```

SEQ ID NO: 52
SEQ ID NO: 38

```
            G  S  I  E  G  R  V  P           D  Q  *
    #5      GATCCATCGAGGGTAGGGTGCCT  -----  GACCAGTA
```

```
            G  S  I  E  G  R  G  G  Q  C        F  K  *
    #6      GATCAATCGAGGGTAGGGGTGGTCAGTGC  ----  TTTAAGTA
```

```
   G  K  G  S  H  H  H  H  H  H
   GGGAAGGGATCGCATCACCATCACCATCACG  -----  AGCTTGGCGTA
                                    BamHI        HindIII
```

α₂MR:

```
            G  S  I  E  G  R  G  T              F  K  *
#7          GATCCATCGAGGGTAGGGGCACC -----        TTTAAGTA

G  S  I  E  G  R  A  V              H  I  *
#8          GATCCATCGAGGGTAGGGCGGTG -----        CACATCTA

G  S  I  E  G  R  V  S              S  I  *
#9          GATCCATCGAGGGTAGGGTGTCC -----        AGCATCTA
```

```
G  K  G  S  H  H  H  H  H  H
GGGAAGGGATCGCATCACCATCACCATCACG ------ AGCTTGGCGTA
                                       BamHI  HindIII
```

SEQ ID NO: 52
SEQ ID NO: 38

α₂-Macroglobulin Receptor.                                    SEQ ID NO: 52

```
                  20
  1 MLTPPLLLLLPLLSALVAAAIDAPKTCSPKQFACRDQITCISKGWRCDGERDCPDGSDEA
                                                          109
 61 PEICPQSKAQRCQPNEHNCLGTELCVPMSRLCNGVQDCMDGSDEGPHCRELQGNCSRLGC
121 QHHCVPTLDGPTCYCNSSFQLQADGKTCKDFDECSVYGTCSQLCTNTDGSFICGCVEGYL
                  190
181 LQPDNRSCKAKNEPVDRPPVLLIANSQNILATYLSGAQVSTITPTSTRQTTAMDFSYANE
241 TVCWVHVGDSAAQTQLKCARMPGLKGFVDEHTINISLSLHHVEQMAIDWLTGNFYFVDDI
301 DDRIFVCNRNGDTCVTLLDLELYNPKGIALDPAMGKVFFTDYGQIPKVERCDMDGQNRTK
361 LVDSKIVFPHGITLDLVSRLVYWADAYLDYIEVVDYEGKGRQTIIQGILIEHLYGLTVFE
421 NYLYATNSDNANAQQKTSVIRVNRFNSTEYQVVTRVDKGGALHIYHQRRQPRVRSHACEN
                                        521
481 DQYGKPGGCSDICLLANSHKARTCRCRSGFSLGSDGKSCKKPEHELFLVYGKGRPGIIRG
541 MDMGAKVPDEHMIPIENLMNPRALDFHAETGFIYFADTTSYLIGRQKIDGTERETILKDG
601 IHNVEGVAVDWMGDNLYWTDDGPKKTISVARLEKAAQTRKTLIEGKMTHPRAIVVDPLNG
661 WMYWTDWEEDPKDSRRGRLERAWMDGSHRDIFVTSKTVLWPNGLSLDIPAGRLYWVDAFY
721 DRIETILLNGTDRKIVYEGPELNHAFGLCHHGNYLFWTEYRSGSVYRLERGVGGAPPTVT
                  803
781 LLRSERPPIFEIRMYDAQQQQVGTNKCRVNNGGCSSLCLATPGSRQCACAEDQVLDADGV
841 TCLANPSYVPPPQCQPGEFACANSRCIQERWKCDGDNDCLDNSDEAPALCHQHTCPSDRF
901 KCENNRCIPNRWLCDGDNDCGNSEDESNATCSARTCPPNQFSCASGRCIPISWTCDLDDD
961 CGDRSDESASCAYPTCFPLTQFTCNNGRCININWRCDNDNDCGDNSDEAGCSHSCSSTQF
1021 KCNSGRCIPEHWTCDGDNDCGDYSDETHANCTNQATRPPGGCHTDEFQCRLDGLCIPLRW
1081 RCDGDTDCMDSSDEKSCEGVTHVCDPSVKFGCKDSARCISKAWVCDGDNDCEDNSDEENC
                                        1184
1141 ESLACRPPSHPCANNTSVCLPPDKLCDGNDDCGDGSDEGELCDQCSLNNGGCSHNCSVAP
1201 GEGIVCSCPLGMELGPDNHTCQIQSYCAKHLKCSQKCDQNKFSVKCSCYEGWVLEPDGES
                  1265
1261 CRSLDPFKPFIIFSNRHEIRRIDLHKGDYSVLVPGLRNTIALDFHLSQSALYWTDVVEDK
1321 IYRGKLLDNGALTSFEVVIQYGLATPEGLAVDWIAGNIYWVESNLDQIEVAKLDGTLRTT
1381 LLAGDIEHPRAIALDPRDGILFWTDWDASLPRIEAASMSGAGRRTVHRETGSGGWPNGLT
1441 VDYLEKRILWIDARSDAIYSARYDGSGHMEVLRGHEFLSHPFAVTLYGGEVYWTDWRTNT
1501 LAKANKWTGHNVTVVQRTNTQPFDLQVYHPSRQPMAPNPCEANGGQGPCSHLCLINYNRT
                  1582
1561 VSCACPHLMKLHKDNTTCYEFKKFLLYARQMEIRGVDLDAPYYNYIISFTVPDIDNVTVL
1621 DYDAREQRVYWSDVRTQAIKRAFINGTGVETVVSADLPNAHGLAVDWVSRNLFWTSYDTN
1681 KKQINVARLDGSFKNAVVQGLEQPHGLVVHPLRGKLYWTDGDNISMANMDGSNRTLLFSG
1741 QKGPVGLAIDFPESKLYWISSGNHTINRCNLDGSGLEVIDAMRSQLGKATALAIMGDKLW
1801 WADQVSEKMGTCSKADGSGSVVLRNSTTLVMHMKVYDESIQLDHKGTNPCSVNNGDCSQL
1861 CLPTSETTRSCMCTAGYSLRSGQQACEGVGSFLLYSVHEGIRGIPLDPNDKSDALVPVSG
1921 TSLAVGIDFHAENDTIYWVDMGLSTISRAKRDQTWREDVVTNGIGRVEGIAVDWIAGNIY
1981 WTDQGFDVIEVARLNGSFRYVVISQGLDKPRAITVHPEKGYLFWTEWGQYPRIERSRLDG
2041 TERVVLVNVSISWPNGISVDYQDGKLYWCDARTDKIERIDLETGENREVVLSSNNMDMFS
2101 VSVFEDFIYWSDRTHANGSIKRGSKDNATDSVPLRTGIGVQLKDIKVFNRDRQKGTNVCA
2161 VANGGCQQLCLYRGRGQRACACAHGMLAEDGASCREYAGYLLYSERTILKSIHLSDERNL
2221 NAPVQPFEDPEHMKNVIALAFDYRAGTSPGTPNRIFFSDIHFGNIQQINDDGSRRITIVE
2281 NVGSVEGLAYHRGWDTLYWTSYTTSTITRHTVDQTRPGAFERETVITMSGDDHPRAFVLD
2341 ECQNLMFWTNWNEQHPSIMRAALSGANVLTLIEKDIRTPNGLAIDHRAEKLYFSDATLDK
2401 IERCEYDGSHRYVILKSEPVHPFGLAVYGEHIFWTDWVRRAVQRANKHVGSNMKLLRVDI
                                                          2520
2461 PQQPMGIIAVANDTNSCELSPCRINNGGCQDLCLLTHQGHVNCSCRGGRILQDDLTCRAV
2521 NSSCRAQDEFECANGECINFSLTCDGVPHCKDKSDEKPSYCNSRRCKKTFRQCSNGRCVS
2581 NMLWCNGADDCGDGSDEIPCNKTACGVGEFRCRDGTCIGNSSRCNQFVDCEDASDEMNCS
2641 ATDCSSYFRLGVKGVLFQPCERTSLCYAPSWVCDGANDCGDYSDERDCPGVKRPCPLNY
2701 FACPSGRCIPMSWTCDKEDDCEHGEDETHCNKFCSEAQFECQNHRCISKQWLCDGSDDCG
```

Fig. 9a

```
2761 DGSDEAAHCEGKTCGPSSFSCPGTHVCVPERWLCDGDKDCADGADESIAAGCLYNSTCDD
2821 REFMCQNRQCIPKHFVCDHDRDCADGSDESPECEYPTCGPSEFRCANGRCLSSRQWECDG
2881 ENDCHDQSDEAPKNPHCTSPEHKCNASSQFLCSSGRCVAEALLCNGQDDCGDSSDERGCH
     2941
2941 INECLSRKLSGCSQDCEDLKIGFKCRCRPGFRLKDDGRTCADVDECSTTFPCSQRCINTH
3001 GSYKCLCVEGYAPRGGDPHSCKAVTDEEPFLIFANRYYLRKLNLDGSNYTLLKQGLNNAV
3061 ALDFDYREQMIYWTDVTTQGSMIRRMHLNGSNVQVLHRTGLSNPDGLAVDWVGGNLYWCD
3121 KGRDTIEVSKLNGAYRTVLVSSGLREPRALVVDVQNGYLYWTDWGDHSLIGRIGMDGSSR
3181 SVIVDTKITWPNGLTLDYVTERIYWADAREDYIEFASLDGSNRHVVLSQDIPHIEFALTLF
3241 EDYVYWTDWETKSINRAHKTGTNKTLLISTLHRPMDLHVFHALRQDVPNHPCKVNNGG
     3331
3301 CSNLCLLSPGGGHKCACPTNFYLGSDGRTCVSNCTASQFVCKNDKCIPFWWKCDTEDDCG
3361 DHSDEPPDCPEFKCRPGQFQCSTGICTNPAFICDGDNDCQDNSDEANCDIHVCLPSQFKC
3421 TNTNRCIPGIFRCNGQDNCGDGEDERDCPEVTCAPNQFQCSITKRCIPRVWVCDRDNDCV
3481 DGSDEPANCTQMTCGVDEFRCKDSGRCIPARWKCDGEDDCGDGSDEPKEECDERTCEPYQ
3541 FRCKNNRCVPGRWQCDYDNDCGDNSDEESCTPRPCSESEFSCANGRCIAGRWKCDGDHDC
3601 ADGSDEKDCTPRCDMDQFQCKSGHCIPLRWRCDADADCMDGSDEEAACGTGVRTCPLDEFQ
3661 CNNTLCKPLAWKCDGEDDCGDNSDENPEECARFVCPNRPFRCKNDRVCLWIGRQCDGTD
     3778
3721 NCGDGTDEEDCEPPTAHTHCKDKKEFLCRNQRCLSSLRCNMFDDCGDGSDEEDCSIDP
3781 KLTSCATNASICGDEARCVRTEKAAYCACRSGFHTVPGQPGCQDINECLRFGTCSQLCNN
3841 TKGGHLCSCARNFMKTHNTCKAEGSEYQVLYIADDNEIRSLFPGHPHSAYEQAFQGDESV
3901 RIDAMDVHVKAGRVYWTNWHTGTISYRSLPPAAPPTSNRHRRQIDRGVTHLNISGLKMP
3961 RGIAIDWVAGNVYWTDSGRDVIEVAQMKGENRKTLISGMIDEPHAIVVDPLRGTMYWSDW
4021 GNHPKIETAAMDGTLRETLVQDNIQWPTGLAVDYHNERLYWADAKLSVIGSIRLNGTDPI
4081 VAADSKRGLSHPFSIDVFEDYIYGVTYINNRVFKIHKFGHSPLVNLTGGLSHASDVVLYH
4141 QHKQPEVTNPCDRKKCEWLCLLSPSGPVCTCPNGKRLDNGTCVPVPSPTPPDAPRPGTC
4201 NLQCFNGGSCFLNARRQPKCRCQPRYTGDKCELDQCWEHCRNGGTCAASPSGMPTCRCPT
4261 GFTGPKCTQQVCAGYCANNSTCTVNQGNQPQCRCLPGFLGDRCQYRQCSGYCENFGTCQM
4321 AADGSRQCRCTAYFEGSRCEVNKCSRCLEGACVVNKQSGDVTCNCTDGRVAPSCLTCVGH
4381 CSNGGSCTMNSKMMPECQCPPHMTGPRCEEHVFSQQQPGHIASILIPLLLLIVLVAGV
4441 VFWYKRRVQGAKGFQHQRMTNGAMNVEIGNPTYKMYEGGEPDDVGGLLDADFALDPDKPT
4501 NFTNPVYATLYMGGHGSRHSLASTDEKRELLGRGPEDEIGDPLA
```

SEQ ID NO: 52

Fig. 9b

Bovine FX.

SEQ ID NO: 53

Glu - Plasminogen.

```
  1  EPLDDYVNTQGASLFSVTKKQLGAGSIEEC
 31  AAKCEEDEEFTCRAFQYHSKEQQCVIMAEN
 61  RKSSIIRMRDVVLFEKKVYLSECKTGNGKN
 91  YRGTMSKTKNGITCQKWSSTSPHRPRFSPA
121  THPSEGLEENYCRNPDPQKTGPWCYTTDPE
151  KRYDYCDILECEEECMHCSGENYDGKISKT
181  MSGLECQAWDSQSPHAHGYIPSKFPNRLKT
211  KNCRCTTPPDPPSRLRPWCFTTDPNKRWEL
241  RCHTCQRNPDGPTYQCCLKTHTRRRTKTNT
271  VSGHTCRNPDGKRAPWCHTTNSQVRWEYCN
301  ENYCRNPDGKRAPWCHTTNSQVRWEYCKIP
331  SCDDSPVSTEQLAPTAPPELTPVVQDCYHG
361  DGQSYRGTSSTTTGKKCQSWSSMTPHRHQT
391  KTPENYPNAGLTMNYCRNPDADKGPWCFTT
421  DPSVRWEYCNLKKCSGTEAASAPEEKTKEA
451  PAQNVETPSEEDCMFGNGKGYRGKKATTVT
481  PCQDWAAQEPHRHSIFTPETNPRAGLEKNY
511  CRNPDGDVSGPWCYTTNPRKLYDVVPLVEN
541  AAPSFDCGKPQVEPKKCPGRVVGGCVAHPH
571  SWPWQVSLRTRFGMHFCGGTLISPEWVLTA
601  AHCLEKSPRPSSYKVVLGAHHLKKSPLCE
631  VPACLPSPNYVVADRTECFITGNGKFFVAK
661  AHCEIPACLPSPNYVVADRTECFITGNGDK
691  FGAGLLKEAQLPVACLPVIACCSWGCGDSK
721  STELCAGHLAGGTDSCQGDSGGPLVCFEKD
751  KYILQGVTSWGLGCARPNKPGVYVRVSRFV
781  TWIEGVMRNN
```

SEQ ID NO: 54

Fig. 14

Human α₂MRBDv

SEQ ID NO: 38

```
            G  S  I  E  G  R  V  Y           N  A  *
            GATCCATCGAGGGTAGGGTCTAC ------ AATGCTTGA

M  G  S  H  H  H  H  H  H
CATATGGGATCGGATCCATCACCATCACCATCACG ------ AGCTTGAATTC
            BamHI                          HindIII
```

Fig. 18 pT₇H₆

Phage T7 Promoter
Ori
Ampʳ

Human $\alpha_2$MRBDv.

```
                                 10                                      20                                      30
(1299)V Y L Q T S L K Y N I L P E K E E F P F A L G V Q T L P Q T 40                                      50                                      60
      C D E P K A H T S F Q I S L S V S Y T G S R S A S N M A I V 70                                      80                                      90
      D V K M V S G F I P L K P T V K M L E R S N H V S R T E V S 100                                     110                                     120
      S N H V L I Y L D K V S N Q T L S L F F T V L Q D V P V R D 130                                     140                                     150
      L K P A I V K V Y D Y Y E T D E F A I A E Y N A P C S K D L

153
      G N A(1451)
```

SEQ ID NO: 55

Human Tetranectin.

```
    -21
    M E L W G A Y L L L C L F S L L T Q V T T E P P T Q K P K K
     10                    20             30
    I V N A K K D V V N T K M F E E L K S R L D T L A Q E V A L
     40                    50             60
    L K E Q Q A L Q T V C L K G T K V H M K C F L A F T Q T K T
     70                    80             90
    F H E A S E D C I S R G G T L S T P Q T G S E N D A L Y E Y
    100                   110            120
    L R Q S V G N E A E I W L G L N D M A A E G T W V D M T G A
    130                   140            150
    R I A Y K N W E T E I T A Q P D G G K T E N C A V L S G A A
    160                   170            180
    N G K W F D K R C R D Q L P Y I C Q F G I V
```

SEQ ID NO: 56

```
  1 QVKLQQSGAELVKPGASVKMSCKASGYTFA
 31 SYWINWVKQRPGQGLEWIGHIYPVRSITKY
 61 NEKFKSKATLTLDTSSSTAYMQLSSLTSED
 91 SAVYYCSRGDGSDYYAMDYWGQGTTVTVSS
121 GGGGSDIELTQSPAILSASPGGKVTMTCRA
151 SSSVSYMHWYQQKPGSSPKPWIYATSNLAS
181 GVPTRFSGSGTGSGTSYSLTISRVEAEDAATY
211 YCQQWSRNPFTFGSGTKLEIKRAAAEQKLI
241 SEEDLN
```

SEQ ID NO: 57

Fig. 23

Human Psoriasin.

```
  1                            10                            20                            30
  M  S  N  T  Q  A  E  R  S  I  I  G  M  I  D  M  F  H  K  Y  T  R  R  D  D  K  I  D  K  P
                                 40                            50                            60
  S  L  L  T  M  M  K  E  N  F  P  N  F  L  S  A  C  D  K  K  G  T  N  Y  L  A  D  V  F  E
                                 70                            80                            90
  K  K  D  K  N  E  D  K  K  I  D  F  S  E  F  L  S  L  L  G  D  I  A  T  D  Y  H  K  Q  S
                                100
  H  G  A  A  P  C  S  G  G  S  Q
```

SEQ ID NO: 58

Fig. 25

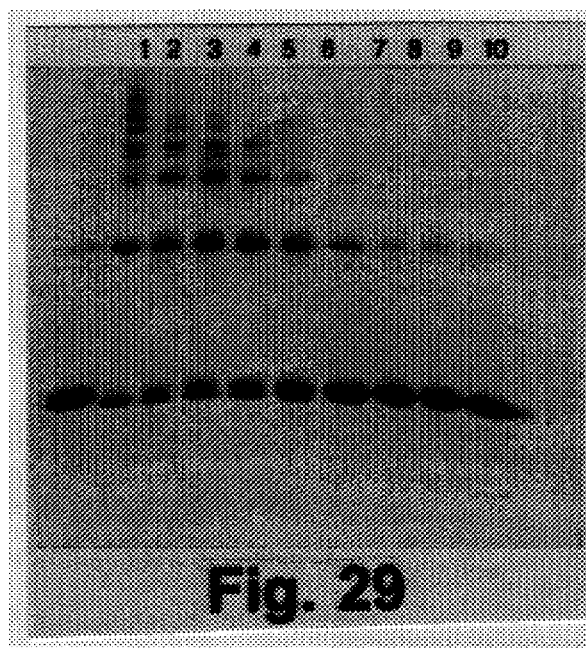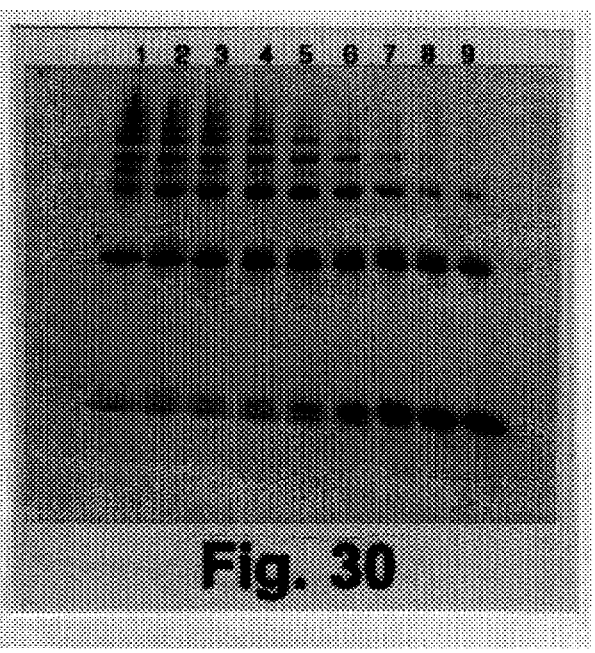

5,739,281

INTERATIVE METHOD OF AT LEAST THREE CYCLES FOR THE REFOLDING OF PROTEINS

This is a continuation of application Ser. No. 08/192,060, filed on Feb. 4, 1994 (now abandoned), which is a continuation of Danish applications: Serial No. 130/93, filed Feb. 4, 1993; and Serial No. 139/93, filed Feb. 5, 1993; and International application, Ser. No. PCT/GB93/02492, filed Dec. 3, 1993.

FIELD OF THE INVENTION

This invention relates to recombinant DNA technology and, in particular to protein engineering technologies for the production of correctly folded proteins by expression of genes or gene fragments in a host organism, heterologous or homologous, as recombinant protein products, by describing novel general principles and methodology for efficient in vitro refolding of misfolded and/or insoluble proteins, including proteins containing disulphide bonds. This invention further relates to the refolding of unfolded or misfolded polypeptides of any other origin. The invention also relates to novel designs of encrypted recognition sites for factor $X_a$ cleavage of chimeric proteins, sites that only become recognized after in vitro derivatization. Two analogues of bovine coagulation factor $X_a$, suitable for small-, medium-, or large-scale technological applications involving specific cleavage of chimeric proteins at sites designed for cleavage by factor $X_a$ are provided, too. Finally the invention relates to designs of reversible disulphide-blocking reagents, useful as auxiliary compounds for refolding of cysteine-containing proteins, including a general assay procedure by which such disulphide exchange reagents can be evaluated for suitability for this specific purpose.

GENERAL BACKGROUND OF THE INVENTION

Technologies for the production of virtually any polypeptide by introduction, by recombinant DNA methods, of a natural or synthetic DNA fragment coding for this particular polypeptide into a suitable host have been under intense development over the past fifteen years, and are at present essential tools for biochemical research and for a number of industrial processes for production of high-grade protein products for biomedical or other industrial use.

Four fundamental properties of biological systems render heterologous production of proteins possible.

(i) The functional properties of a protein are entirely specified by its three-dimensional structure, and, due to the molecular environment in the structure, manifested by chemical properties exhibited by specific parts of this structure.

(ii) The three-dimensional structure of a protein is, in turn, specified by the sequence information represented by the specific sequential arrangement of amino acid residues in the linear polypeptide chain(s). The structure information embedded in the amino acid sequence of a polypeptide is by itself sufficient, under proper conditions, to direct the folding process, of which the end product is the completely and correctly folded protein.

(iii) The linear sequence of amino acid residues in the polypeptide chain is specified by the nucleotide sequence in the coding region of the genetic material directing the assembly of the polypeptide chain by the cellular machinery. The translation table governing translation of nucleic acid sequence information into amino acid sequence is known and is almost universal among known organisms and hence allows nucleic acid segments coding for any polypeptide segment to direct assembly of polypeptide product across virtually any cross-species barrier.

(iv) Each type of organism relies on its own characteristic array of genetic elements present within its own genes to interact with the molecular machinery of the cell, which in response to specific intracellular and extracellular factors regulates the expression of a given gene in terms of transcription and translation.

In order to exploit the protein synthesis machinery of a host cell or organism to achieve substantial production of a desired recombinant protein product, it is therefore necessary to present the DNA-segment coding for the desired product to the cell fused to control sequences recognized by the genetic control system of the cell.

The immediate fate of a polypeptide expressed in a host is influenced by the nature of the polypeptide, the nature of the host, and possible host organism stress states invoked during production of a given polypeptide. A gene product expressed in a moderate level and similar or identical to a protein normally present in the host cell, will often undergo normal processing and accumulation in the appropriate cellular compartment or secretion, whichever is the natural fate of this endogenous gene product. In contrast, a recombinant gene product which is foreign to the cell or is produced at high levels often activates cellular defence mechanisms similar to those activated by heat shock or exposure to toxic amino acid analogues, pathways that have been designed by nature to help the cell to get rid of "wrong" polypeptide material by controlled intracellular proteolysis or by segregation of unwanted polypeptide material into storage particles ("inclusion bodies"). The recombinant protein in these storage particles is often deposited in a misfolded and aggregated state, in which case it becomes necessary to dissolve the product under denaturing and reducing conditions and then fold the recombinant polypeptide by in vitro methods to obtain a useful protein product.

Expression of eukaryotic genes in eukaryotic cells often allows the direct isolation of the correctly folded and processed gene product from cell culture fluids or from cellular material. This approach is often used to obtain relatively small amounts of a protein for biochemical studies and is presently also exploited industrially for production of a number of biomedical products. However, eukaryotic expression technology is expensive in terms of technological complexity, labour- and material costs. Moreover, the time scale of the development phase required to establish an expression system is at least several months, even for laboratory scale production. The nature and extent of post-translational modification of the recombinant product often differs from that of the natural product because such modifications are under indirect genetic control in the host cell. Sequence signals invoking a post-synthetic modification are often mutually recognized among eukaryotes, but availability of the appropriate suite of modification enzymes is given by the nature and state of the host cell.

A variety of strategies have been developed for expression of gene products in prokaryotic hosts, advantageous over eukaryotic hosts in terms of capital, labour and material requirements. Strains of the eubacteria *Escherichia coli* are often preferred as host cells because *E. coli* is far better characterized genetically than any other organism, also at the molecular level.

Prokaryotic host cells do not possess the enzymatic machinery required to carry out post-translational modification, and an eukaryotic gene product will therefore necessarily be produced in its unmodified form. Moreover, the product must be synthesized with an N-terminal extension, at least one additional methionine residue arising from the required translation initiation codon, more often also including an N-terminal segment corresponding to that of a highly expressed host protein. General methods to remove such N-terminal extensions by sequence specific proteolysis at linker segments inserted at the junction between the N-terminal extension and the desired polypeptide product have been described (Enterokinase-cleavable linker sequence: EP 035384, The Regents of the University of California; Factor $X_a$-cleavable linker sequence: EP 161937, Nagai & Thøgersen, Assignee: Celltech Ltd.).

Over the years a considerable effort has been directed at the development of strategies for heterologous expression in prokaryotes to generate recombinant protein products in a soluble form or fusion protein constructs that allow secretion from the cell in an active, possibly N-terminally processed form, an effort resulting in limited success only, despite recent developments in the chaperone field. Typically, much time and effort is required to develop and modify an expression system before even a small amount of soluble and correctly folded fusion protein product can be isolated. More often all of the polypeptide product is deposited within the host cell in an improperly folded state in "inclusion bodies". This is particularly true when expressing eukaryotic proteins containing disulphide bridges.

Available methods for in vitro refolding of proteins all describe processes in which the protein in solution or non-specifically adsorbed to ion exchange resins etc. is exposed to solvent, the composition of which is gradually changed over time from strongly denaturing (and possibly reducing) to non-denaturing in a single pass. This is often carried out by diluting a concentrated solution of protein containing 6–8M guanidine hydrochloride or urea into a substantial volume of non-denaturing buffer, or by dialysis of a dilute solution of the protein in the denaturing buffer against the non-denaturing buffer. Numerous variants of this basic procedure have been described, including addition of specific ligands or cofactors of the active protein and incorporation of polymer substances like poly ethylene oxide (polyethylene glycol), thought to stabilize the folded structure.

Although efficient variants of the standard in vitro refolding procedure have been found for a number of specific protein products, including proteins containing one or more disulphide bonds, refolding yields are more often poor, and scale-up is impractical and expensive due to the low solubility of most incompletely folded proteins which implies the use of excessive volumes of solvent.

The common characteristic of all traditional in vitro refolding protocols is that refolding induced by sudden or gradual reduction of denaturant is carried out as a single-pass operation, the yield of which is then regarded as the best obtainable for the protein in question.

The general field of protein folding has been summarized in a recent text book edited by Thomas W. Creighton ("Protein folding", ed. Creighton T. E., Freeman 1992) and a more specific review of practical methods for protein refolding was published in 1989 by Rainer Jaenicke & Rainer Rudolph (p. 191–223 in. "Protein Structure, a practical approach", ed. T. E. Creighton, IRL Press 1989). Among the numerous more detailed publications, state-of-the-art reviews like those by Schein (Schein C. H., 1990, Bio/Technology 8, 308–317) or Buchner and Rudolph (Buchner J. and Rudolph R, 1991 Bio/Technology 9, 157–162) may be consulted.

In conclusion, there is a definite need for generally applicable high-yield methods for the refolding of un- or misfolded proteins derived from various sources, such as prokaryotic expression systems or peptide synthesis.

SUMMARY OF THE INVENTION

It has been found by the inventors that refolding yields can be greatly increased by taking into account that the protein folding process is a kinetically controlled process and that interconversion between folded, unfolded and misfolded conformers of the protein are subject to hysteresis and time-dependent phenomena that can be exploited to design a cyclic denaturation-renaturation process, in which refolded protein product accumulates incrementally in each cycle at the expense of unfolded and misfolded conformers, to generate a new refolding process of much greater potential than the basic traditional approach.

By the term "folded protein" is meant a polypeptide in (a) conformational state(s) corresponding to that or those occurring in the protein in its biologically active form or unique stable intermediates that in subsequent steps may be converted to generate the biologically active species. The covalent structure of the folded protein in terms of crosslinking between pairs of cysteine residues in the polypeptide is identical to that of the protein in its biologically active form.

Accordingly, the term "unfolded protein" refers to a polypeptide in conformational states less compact and well-defined than that or those corresponding to the protein in its biologically active, hence folded, form. The covalent structure of the unfolded protein in terms of crosslinking between pairs of cysteine residues in the polypeptide may or may not be identical to that of the protein in its biologically active form. Closely related to an unfolded protein is a "misfolded protein" which is a polypeptide in a conformational state which is virtually thermodynamically stable, sometimes even more so than that or those states corresponding to the protein in its folded form, but which does not exhibit the same degree, if any, of the biological activity of the folded protein. As is the case for the unfolded protein, the covalent structure in terms of crosslinking between pairs of cysteine residues in the polypeptide may or may not be the same as that of the folded protein.

By the term "refolded protein" is meant a polypeptide which has been converted from an unfolded state to attain its biologically active conformation and covalent structure in terms of crosslinking between correct pairs of cysteine residues in the polypeptide.

The new generally applicable protein refolding strategy has been designed on the basis of the following general properties of protein structure.

(a) The low solubility of unfolded proteins exposed to non-denaturing solvents reflects a major driving force inducing the polypeptide either to form the compact correctly refolded structure or to misfold and generate dead-end aggregates or precipitates, which are unable to refold and generate the correctly refolded structure under non-denaturing conditions within a reasonable amount of time.

(b) A newly formed dead-end aggregate is more easily "denatured" i.e. converted into an unfolded form than the correctly refolded protein because the structure of the dead-end aggregate is more disordered. Probably misfolding is also in general a kinetically controlled process.

(c) An unfolded protein is often not (or only very slowly) able to refold into the correctly refolded form at denaturant levels required to denature dead end aggregates within a reasonable amount of time.

(d) The body of evidence available to support (b) includes detailed studies of folding and unfolding pathways and intermediates for several model proteins. Also illustrative is the observation made for many disulphide bonded proteins that the stability of disulphide bonds against reduction at limiting concentrations of reducing and denaturing agents is often significantly different for each disulphide bridge of a given protein, and that the disulphide bridges in the folded protein are in general much less prone to reduction or disulphide exchange than "non-native" disulphide bonds in a denatured protein or protein aggregate.

The new strategy for a refolding procedure is most easily illustrated by way of the following theoretical example:

Consider a hypothetical protein—stably folded in a non-denaturing buffer "A" and stably unfolded in the strongly denaturing buffer "B" (being e.g. a buffer containing 6M guanidine-HCl)—exposed to buffer A or to buffer B and then subjected to incubation at intermediate levels of denaturation in mixtures of buffers A and B.

Levels between e.g. 100 to 75% B lead to conversion of both folded protein and dead-end aggregated protein to the unfolded form within a short period of time.

Levels between e.g. 75-50% B lead to conversion of newly formed dead-end aggregate to the unfolded form, whereas almost all refolded protein remains in a native-like structure, stable at least within a period of time of hours, from which it may snap back into the refolded form upon removal of the denaturant.

Levels in excess of 10% B prevent rapid formation of refolded form from unfolded form.

A solvent composition step from 100% B to 0% B converts unfolded protein to dead-end aggregate (75% yield) and refolded protein (25% yield).

Let us now subject a sample of this protein, initially in its unfolded form in 100% B, to a time-series of programmed denaturation-renaturation cycles as illustrated in FIG. 1, each consisting of a renaturation phase ($F_n$) (<10% B) and a denaturation phase ($D_n$). At the end of the renaturation phase of cycle (i) the denaturant content is changed to a level, $k_i$ % less than the denaturant level of the previous cycle. Following a brief incubation the denaturant is again removed, and the next renaturation phase $F_{i+1}$ entered. Assuming the denaturation level starts out at 100% B and $k_i$ for each cycle is fixed at 4%, this recipe will generate a damped series of "denaturation steps" dying out after 25 cycles.

Through 25 cycles, as outlined above, the accumulation of refolded protein would progress as follows:

In cycles 1 to 5 all of the protein, folded as well as misfolded will become unfolded in each of the denaturation phases $D_n$.

Cycles 7 through 12: Dead-end aggregates will be converted to unfolded protein in each step whereas protein recoverable as refolded product will accumulate in the following amounts, cycle by cycle: 25%, 44%, 58%, 68%, 76% and 82%.

No further conversions take place through cycles 13 to 25.

The cyclic refolding process would therefore produce a total refolding yield of over 80%, whereas traditional one-pass renaturation at best would produce a yield of 25%.

It will be appreciated that a great number of simplifying approximations in terms of all-or-none graduation of each characteristic of the various conformational states of the hypothetical protein have been made. The basic working principle, nevertheless, remains similar if a more complicated set of presumptions are incorporated in the model.

Arranging a practical setup for establishing a cyclic denaturation/renaturation protein refolding process can be envisaged in many ways.

The protein in solution could e.g. be held in an ultrafiltration device, held in a dialysis device or be confined to one of the phases of a suitable aqueous two-phase system, all of which might allow the concentration of low-molecular weight chemical solutes in the protein solution to be controlled by suitable devices.

Alternatively, the protein could be adsorbed to a suitable surface in contact with a liquid phase, the chemical composition of which could be controlled as required. A suitable surface could e.g. be a filtration device, a hollow-fibre device or a beaded chromatographic medium. Adsorption of the protein to the surface could be mediated by non-specific interactions, e.g. as described in WO 86/05809 (Thomas Edwin Creighton), by folding-compatible covalent bonds between surface and protein or via specific designs of affinity handles in a recombinant derivative of the protein exhibiting a specific and denaturation-resistant affinity for a suitably derivatized surface.

The specific implementation of the cyclic denaturation/ renaturation protein refolding process established to investigate the potential of the general method was based on a design of cleavable hybrid proteins (EP 161937, Nagai & Thøgersen, Assignee: Celltech Ltd.) containing a metal affinity handle module (EP 0282042 (Heinz Döbeli, Bernhard Eggimann, Reiner Gentz, Erich Hochuli; Hoffmann-La Roche)) inserted N-terminally to the designed factor $X_a$ cleavage site. Recombinant proteins of this general design, adsorbed on Nickel-chelating agarose beads could then be subjected to the present cyclic refolding process in a chromatographic column "refolding reactor" perfused with a mixture of suitable denaturing and non-denaturing buffers, delivered by an array of calibrated pumps, the flow rates of which was time-programmed through computer control.

A general scheme of solid-state refolding entails cycling the immobilized protein as outlined above or by any other means and implementations between denaturing and non-denaturing conditions in a progressive manner, in which the concentration of the denaturing agent is gradually reduced from high starting values towards zero over a train of many renaturation-denaturation cycles. Using this approach it is not necessary to determine precisely which limiting denaturant concentration is required to obtain folding yield enrichment in the course of cycling of the specific protein at hand, because the progressive train of cycles will go through (up to) three phases, an early phase in which folded product present at the end of cycle (i) is completely denatured at the denaturation step of cycle (i+1), an intermediate productive phase during which refolded protein accumulates in increasing quantity, and a late phase during which the concentration of denaturant is too low to perturb the refolded protein or any remaining misfolded structures. Subjecting the protein to a progressing series of denaturation-renaturation cycles as outlined will therefore include several productive cycles.

For disulphide-containing proteins progressive denaturation-renaturation cycling may be enhanced by using equipment similar to advanced chromatography equipment with on-line facilities to monitor buffer compositions of folding reactor effluent. Information on effluent composition with regard to reductant and disulphide reshuffling reagent concentration profile would reveal productive cycling, and could therefore be used as input to an intelligent processor unit, in turn regulating the progression of denaturant concentration in a feed-back loop to ensure that most of the cycling effort is spent within the productive phase of the denaturation-renaturation cycle train. Such auto-optimization of cycling conditions would be possible because the analytical system may be used to measure extent and direction of changes in redox equilibrium in the buffer stream, measurements that directly reflect titration of thiol-groups/disulphide equivalents in the immobilized protein sample, and is therefore directly translatable into average number of disulphide bonds being disrupted or formed during the various phases of a cycle.

Other possible inputs for the intelligent processor controlling the progression of cycling include measurements of ligand-binding, substrate conversion, antibody binding ability and, indeed, any other interacting soluble agent interacting in distinct ways with misfolded and folded protein, which in the assessing stage of folding measurement might be percolated through the refolding reactor and then in-line monitored in the effluent by suitable analytical devices.

An intelligent monitoring and control system could furthermore use the available information to direct usable portions of reactor effluent to salvage/recycling subsystems thereby minimizing expenses for large scale operations.

After execution of the folding procedure the final product may be eluted from the affinity matrix in a concentrated form, processed to liberate the mature authentic protein by cleavage at the designed protease cleavage site and then subjected to final work-up using standard protein purification and handling techniques, well-known within the field of protein chemistry.

DETAILED DISCLOSURE OF THE INVENTION

Thus, the present invention relates to a method for generating a processed ensemble of polypeptide molecules, in which processed ensemble the conformational states represented contain a substantial fraction of polypeptide molecules in one particular uniform conformation, from an initial ensemble of polypeptide molecules which have the same amino acid sequence as the processed ensemble of polypeptide molecules, comprising subjecting the initial ensemble of polypeptide molecules to a series of at least two successive cycles each of which comprises a sequence of 1) at least one denaturing step involving conditions exerting a denaturing influence on the polypeptide molecules of the ensemble followed by 2) at least one renaturing step involving conditions having a renaturing influence on the polypeptide molecules having conformations resulting from the preceding step.

In the present specification and claims, the term "ensemble" is used in the meaning it has acquired in the art, that is, it designates a collection of molecules having essential common features. Initially ("an initial ensemble"), they have at least their amino acid sequence in common (and of course retain this common feature). When the ensemble of polypeptide molecules has been treated in the method of the invention (to result in "a processed ensemble"), the conformational states represented in the ensemble will contain a substantial fraction of polypeptide molecules with one particular conformation. As will be understood from the discussion which follows, the substantial fraction of polypeptide molecules with one particular conformation in the processed ensemble may vary dependent on the parameters of the treatment by the method of the invention, the size of the protein in the particular conformation, the length and identity of the amino acid sequence of the molecules, etc. In the examples reported herein, in which the process parameters have not yet been optimized, the fraction of polypeptide molecules with one particular conformation varied between 15% and 100% of the ensemble, which in all cases is above what could be obtained prior to the present invention. In example 13 it is further demonstrated that purification of the polypeptide molecules prior to their subjection to the method of the invention increases the fraction of polypeptide molecules with one particular conformation.

"Denaturing step" refers to exposure of an ensemble of polypeptide molecules during a time interval to physical and/or chemical circumstances which subject the ensemble of polypeptide molecules to conditions characterized by more severe denaturing power than those characterizing conditions immediately prior to the denaturing step.

Accordingly, the term "renaturing step" refers to exposure of an ensemble of polypeptide molecules during a time interval to physical and/or chemical circumstances which subject the ensemble of polypeptide molecules to conditions characterized by less severe denaturing power than those characterizing conditions immediately prior to the denaturing step.

It will be understood, that the "substantial fraction" mentioned above will depend in magnitude on the ensemble of polypeptide molecules which are subjected to the method of the invention. If the processed ensemble of polypeptides consists of monomeric proteins of relatively short lengths and without intramolecular disulphide bridges the method will in general result in very high yields, whereas complicated molecules (such as polymeric proteins with a complicated disulphide bridging topology) may result in lower yields, even if the conditions of the method of the invention are fully optimized.

An interesting aspect of the invention relates to a method described above wherein the processed ensemble comprises a substantial fraction of polypeptide molecules in one conformational state the substantial fraction constituting at least 1% (w/w) of the initial ensemble of polypeptide molecules. Higher yields are preferred, such as at least 5%, at least 10%, at least 20%, and at least 25% of the initial ensemble of polypeptide molecules. More preferred are yields of at least 30%, such as at least 40%, 50%, 60%, 70%, and at least 80%. Especially preferred are yields of at least 85%, such as 90%, 95%, 97%, and even at 99%. Sometimes yields close to 100% are observed.

When the polypeptide molecules of the ensemble contain cysteine, the processed ensemble will comprise a substantial fraction of polypeptide molecules in one particular uniform conformation which in addition have substantially identical disulphide bridging topology.

In most cases, the polypeptide molecules subjected to the method of the invention will be molecules which have an amino acid sequence identical to that of an authentic polypeptide, or molecules which comprise an amino acid sequence corresponding to that of an authentic polypeptide joined to one or two additional polypeptide segments.

By the term "authentic protein or polypeptide" is meant a polypeptide with primary structure, including N- and C-terminal structures, identical to that of the corresponding natural protein. The term also denotes a polypeptide which has a known primary structure which is not necessarily identical to that of a natural protein, which polypeptide is the intentional end-product of a protein synthesis.

By the term "natural protein" is meant a protein as isolated in biologically active form from an organism, in which it is present not as a consequence of genetic manipulation.

In contrast, the term "artificial protein or polypeptide" as used in the present specification and claims is intended to relate to a protein/polypeptide which is not available from any natural sources, i.e. it cannot be isolated and purified from any natural source. An artificial protein/polypeptide is thus the result of human intervention, and may for instance be a product of recombinant DNA manipulation or a form of in vitro peptide synthesis. According to the above definitions such an artificial protein may be an authentic protein, but not a natural protein.

Thus, the invention also relates to a method wherein natural proteins as well as artificial proteins are subjected to the refolding processes described herein.

As will be explained in greater detail below, it may be advantageous for various reasons that the authentic polypeptide is joined to polypeptide segments having auxiliary functions during the cycling and other previous or subsequent processing, e.g. as "handles" for binding the polypeptide to a carrier, as solubility modifiers, as expression boosters which have exerted their beneficial function during translation of messenger RNA, etc. Such an auxiliary polypeptide segment will preferably be linked to the authentic polypeptide via a cleavable junction, and where two such auxiliary polypeptide segments are linked to the authentic polypeptide, this may be via similar cleavable junctions which will normally be cleaved simultaneously, or through dissimilar cleavable junctions which may be cleaved in any time sequence.

In accordance with what is explained above, it is believed to be a major novel characteristic feature of the present invention that the cycling (which, as explained above, comprises at least two successive cycles) will give rise to at least one event where a renaturing step is succeeded by a denaturing step where at least a substantial fraction of the refolded polypeptides will be denatured again.

In most cases, the processing will comprise at least 3 cycles, often at least 5 cycles and more often at least 8 cycles, such as at least 10 cycles and, in some cases at least 25 cycles. On the other hand, the series of cycles will normally not exceed 2000 cycles and will often comprise at most 1000 cycles and more often at most 500 cycles. The number of cycles used will depend partly on the possibilities made available by the equipment in which the cycling is performed.

Thus, if the cycling treatment is performed with the polypeptide molecules immobilized to a carrier column, such as will be explained in greater detail below, the rate with which the liquid phase in contact with the column can be exchanged will constitute one limit to what can realistically be achieved. On the other hand, high performance liquid chromatography (HPLC) equipment will permit very fast exchange of the liquid environment and thus make cycle numbers in the range of hundreds or thousands realistic.

Other consideration determining the desirable number of cycles are, e.g., inherent kinetic parameters such as interconversion between cis and trans isomers at proline residues which will tend to complicate redistribution over the partially folded states and will thus normally require due consideration of timing. Another time-critical characteristic resides in the kinetics of disulphide reshuffling (cf. the discussion below or disulphide-reshuffling systems).

With due consideration of the above, the cycling series will often comprise at most 200 cycles, more often at most 100 cycles and yet more often at most 50 cycles.

In accordance with what is stated above, the duration of each denaturing step may be a duration which, under the particular conditions in question, is at least one millisecond and at most one hour, and the duration of each renaturing step may be a duration which, under the particular conditions in question, is at least 1 second and at most 12 hours.

In most embodiments of the method, the denaturing conditions of each individual denaturing step are kept substantially constant for a period of time, and the renaturing conditions of each individual renaturing step are kept substantially constant for a period of time, the periods of time during which conditions are kept substantially constant being separated by transition periods during which the conditions are changed. The transition period between steps for which conditions are kept substantially constant may have a duration varying over a broad range, such as between 0.1 second and 12 hours and will normally be closely adapted to the durations of the denaturing and renaturing steps proper.

Bearing this in mind, the period of time for which the denaturing conditions of a denaturing step are kept substantially constant may, e.g. have a duration of at least one millisecond and at most one hour, often at most 30 minutes, and the period of time for which the renaturing conditions of a renaturing step are kept substantially constant has a duration of at least 1 second and at most 12 hours, and often at most 2 hours.

In practice, the period of time for which the denaturing conditions of a denaturing step are kept substantially constant will often have a duration of between 1 and 10 minutes, and the period of time for which the renaturing conditions of a renaturing step are kept substantially constant will often have a duration of between 1 and 45 minutes.

It will be understood from the above, that adjustments should be made to the intervals stated above, taking into consideration the change of kinetics resulting from the change in physical conditions to which the polypeptides are subjected. For instance, the pressure may be very high (up to 5000 Bar) when using an HPLC system when performing the method of the invention, and under such circumstances very rapid steps may be accomplished and/or necessary. Further, as can be seen from the examples, the temperature parameter is of importance, as some proteins only will refold properly at temperatures far from the physiological range. Both temperature and pressure will of course have an effect on the kinetics of the refolding procedure of the invention, and therefore the above-indicated time intervals of renaturing and denaturing steps are realistic boundaries for the many possible embodiments of the invention.

For a given utilization of the method of the invention, the skilled person will be able to determine suitable conditions based, e.g., on preliminary experiments.

As indicated above, the polypeptide molecules are normally in contact with a liquid phase during the denaturing and renaturing steps, the liquid phase normally being an aqueous phase. This means that any reagents or auxiliary substances used in the method will normally be dissolved in the liquid phase, normally in an aqueous phase. However, if convenient, the liquid phase may also be constituted by one or more organic solvents.

In connection with renaturing of proteins, it is well known to use a so-called "chaperone" or "chaperone complex". Chaperones are a group of recently described proteins that show a common feature in their capability of enhancing refolding of unfolded or partly unfolded proteins. Often, the chaperones are multimolecular complexes. Many of these chaperones are heat-shock proteins, which means that in vivo, they are serving as factors doing post traumatic "repair" on proteins that have been destabilized by the trauma. To be able to fulfil this function, chaperones tend to be more stable to traumatic events than many other proteins and protein complexes. While the method of the invention does not depend on the use of a molecular chaperone or a molecular chaperone complex, it is, of course, possible to have a suitable molecular chaperone or molecular chaperone complex present during at least one renaturing step, and it may be preferred to have a molecular chaperone or a molecular chaperone complex present during substantially all cycles.

As mentioned above, the polypeptide molecules are preferably substantially confined to an environment which allows changing or exchanging the liquid phase substantially without entraining the polypeptide molecules. This can be achieved in a number of ways. For instance, the polypeptide molecules may be contained in a dialysis device, or they may be confined to one of the phases of a suitable liquid two-phase system. Such a suitable aqueous two phase system may, e.g., contain a polymer selected from the group consisting of polyethylene oxide (polyethylene glycol), polyvinyl acetate, dextran and dextran sulphate. In one interesting setup, one phase contains polyethylene oxide (polyethylene glycol) and the other phase contains dextran, whereby the polypeptide molecules will be confined to the dextran-containing phase.

Another way of avoiding entraining the polypeptide by having the polypeptide molecules bound to a solid or semi-solid carrier, such as a filter surface, a hollow fibre or a beaded chromatographic medium, e.g. an agarose or polyacrylamide gel, a fibrous cellulose matrix or an HPLC or FPLC (Fast Performance Liquid Chromatography) matrix. As another measure, the carrier may be a substance having molecules of such a size that the molecules with the polypeptide molecules bound thereto, when dissolved or dispersed in a liquid phase, can be retained by means of a filter, or the carrier may be a substance capable of forming micelles or participating in the formation of micelles allowing the liquid phase to be changed or exchanged substantially without entraining the micelles. In cases where the micelle-forming components would tend to escape from the system as monomers, e.g. where they would be able to some extent to pass an ultrafilter used in confining the system, this could be compensated for by replenishment with additional micelle-forming monomers.

The carrier may also be a water-soluble polymer having molecules of a size which will substantially not be able to pass through the pores of a filter or other means used in confining the system.

The polypeptide molecules are suitably non-covalently adsorbed to the carrier through a moiety having affinity to a component of the carrier. Such a moiety may, e.g., be a biotin group or an analogue thereof bound to an amino acid moiety of the polypeptide, the carrier having avidin, streptavidin or analogues thereof attached thereto so as to establish a system with a strong affinity between the thus modified polypeptide molecules and the thus modified carrier. It will be understood that the affinity between the modified polypeptide and the modified carrier should be sufficiently stable so that the adsorption will be substantially unaffected by the denaturing conditions; the removal of the polypeptide molecules from the carrier after the cycling should be performed using specific cleaving, such as is explained in the following.

An example of a suitable amino acid residue to which a biotinyl group may be bound is lysine.

One interesting way of introducing an amino acid carrying a moiety having affinity to the carrier is CPY synthesis. CPY (carboxy peptidase Y) is known to be capable of adding amino acid amide irrespective of the nature of the side chain of that amino acid amide.

In an interesting embodiment, the moiety having affinity to the carrier is the polypeptide segment SEQ ID NO: 47, in which case the carrier suitably comprises a Nitrilotriacetic Acid derivative (NTA) charged with $Ni^{++}$ ions, for instance an NTA-agarose matrix which has been bathed in a solution comprising $Ni^{++}$.

An important aspect of the invention relates to the presence of suitable means in the polypeptide molecule preparing the molecule for later cleavage into two or more segments, wherein one segment is an authentic polypeptide as defined above. Such combined polypeptide molecules (fusion polypeptide molecules) may for this purpose comprise a polypeptide segment which is capable of direction preferential cleavage by a cleaving agent at a specific peptide bond. The polypeptide segment in question may be one which directs the cleavage as a result of the conformation of the segment which serves as a recognition site for the cleaving agent.

The cleavage directing polypeptide segment may for instance be capable of directing preferential cleavage at a specific peptide bond by a cleaving agent selected from the group consisting of cyanogen bromide, hydroxylamine, iodosobenzoic acid and N-bromosuccinimide.

The cleavage-directing polypeptide segment may be one which is capable of directing preferential cleavage at a specific peptide bond by a cleaving agent which is an enzyme and one such possible enzyme is bovine enterokinase or an analogue and/or homologue thereof.

In an important aspect of the invention, the cleaving agent is the enzyme bovine coagulation factor $X_a$ or an analogue and/or homologue thereof (such analogues will be discussed in greater detail further below), and the polypeptide segment which directs preferential cleavage is a sequence which is substantially selectively recognized by the bovine coagulation factor $X_a$ or an analogue and/or homologue thereof. Important such segments are polypeptide segments that have a sequence selected from the group consisting of SEQ ID NO: 38, SEQ ID NO: 40, SEQ ID NO: 41 and SEQ ID NO: 42.

An interesting feature of the invention is the possibility of masking and unmasking polypeptide segments with respect to their ability to direct cleavage at a specific peptide bond, whereby it is obtained that different segments of the polypeptide can be cleaved at different stages in the cycles.

Thus, when the polypeptide molecules comprise a polypeptide segment which is in vitro-convertible into a derivatized polypeptide segment capable of directing preferential cleavage by a cleaving agent at a specific peptide bond, a masking/unmasking effect as mentioned becomes available. An especially interesting version of this strategy is where the in vitro-convertible polypeptide segment is convertible into a derivatized polypeptide segment which is substantially selectively recognized by the bovine coagulation factor $X_a$ of an analogue and/or homologue thereof.

It is contemplated that both cysteine and methionine residues can be converted into modified residues, which modified residues make the segments having amino acid sequences selected from the group consisting of SEQ ID NO: 43, SEQ ID NO: 44, SEQ ID NO: 45 and SEQ ID NO: 46 in vitro convertible into segments recognized by bovine coagulation factor $X_a$ or an analogue and/or homologue thereof.

According to the invention, one possible solution involving the cysteine residue is that a polypeptide segment with the amino acid sequence SEQ ID NO: 43 or SEQ ID NO: 44, is converted into a derivatized polypeptide which is substantially selectively recognized by bovine coagulation factor $X_a$, by reacting the cysteine residue with N (2 mercaptoethyl)morpholyl-2-thiopyridyl disulphide or mercaptothioacetate-2-thiopyridyl disulphide.

A possible strategy according to the invention involving methionine is that a polypeptide segment with the amino acid sequence SEQ ID NO: 45 or SEQ ID NO: 46, is converted into a derivatized polypeptide, which is substantially selectively recognized by bovine coagulation factor $X_a$, by oxidation of the thioether moiety in the methionine side group to a sulphozide or sulphone derivative.

Preferred embodiments of the method according to the invention are those wherein the cleavage-directing segments with the amino acid sequences SEQ ID NO: 38, SEQ ID NO: 40, SEQ ID NO: 41 or SEQ ID NO: 42, or the masked cleavage-directing segments with the amino acid sequences SEQ ID NO: 43, SEQ ID NO: 44, SEQ ID NO: 45 and SEQ ID NO: 46 are linked N-terminally to the authentic polypeptide, because then no further processing other than the selective cleaving is necessary in order to obtain the authentic polypeptide in solution. On the other hand, one possible reason for linking the cleavage directing sequences at the C-terminal and of the authentic polypeptide would be that the correct folding of the polypeptide molecules is dependent on a free N-terminal of the polypeptide molecules. In such a case, the part of the cleaving directing sequence remaining after cleaving can be removed by suitable use of carboxypeptidases A and B.

The change of conditions during the transition period between the steps may according to the invention be accomplished by changing the chemical composition of the liquid phase with which the polypeptide molecules are in contact. Thus, denaturing of the polypeptide molecules may be accomplished by contacting the polypeptide molecules with a liquid phase in which at least one denaturing compound is dissolved, and renaturing of the polypeptide molecules is accomplished by contacting the polypeptide molecules with a liquid phase which either contains at least one dissolved denaturing compound in such a concentration that the contact with the liquid phase will tend to renature rather than denature the ensemble of polypeptide molecules in their respective conformation states resulting from the preceding step, or contains substantially no denaturing compound.

The expression "denaturing compound" refers to a compound which when present as one of the solutes in a liquid phase comprising polypeptide molecules may destabilize folded states of the polypeptide molecules leading to partial or complete unfolding of the polypeptide chains. The denaturing effect exerted by a denaturing compound increases with increasing concentration of the denaturing compound in the solution, but may furthermore be enhanced or moderated due to the presence of other solutes in the solution, or by changes in physical parameters, e.g. temperature or pressure.

As examples of suitable denaturing compounds to be used in the method according to the invention may be mentioned urea, guanidine-HCl, di-$C_{1-6}$alkylformamides such as dimethylformamide and di-$C_{1-6}$-alkylsulphones.

The liquid phase used in at least one of the denaturing steps and/or in at least one of the renaturing steps may according to the invention contain a least one disulphide-reshuffling system.

"Disulphide reshuffling systems" are redox systems which contain mixtures of reducing and oxidating agents, the presence of which facilitate the breaking and making of disulphide bonds in a polypeptide or between polypeptides. Accordingly, "disulphide reshuffling agents" or "disulphide reshuffling compounds" are such reducing and oxidating agents which facilitate the breaking and making of disulphide bonds in a polypeptide or between polypeptides. In an important aspect of the invention, the disulphide-reshuffling system contained in the aqueous phase which is in contact with the proteins comprises as a disulphide reshuffling system a mixture of a mercaptan and its corresponding disulphide compound.

As an example, all cysteine residues in the polypeptide molecules may have been converted to mixed disulphide products of either glutathione, thiocholine, mercaptoethanol or mercaptoacetic acid, during at least one of the denaturing/renaturing cycles. Such a converted polypeptide is termed a "fully disulphide-blocked polypeptide or protein" and this term thus refers to a polypeptide or a protein in which cysteine residues have been converted to a mixed-disulphide in which each cysteine residue is disulphide-linked to a mercaptan, e.g. glutathione. The conversion of the cysteine residues to mixed disulphide products may be accomplished by reacting a fully denatured and fully reduced ensemble of polypeptide molecules with an excess of a reagent which is a high-energy mixed disulphide compound, such as aliphatic-aromatic disulphide compound, e.g. 2 thiopyridyl glutathionyl disulphide, or by any other suitable method.

As examples of high-energy mixed disulphides, that is, mixed disulphides having a relatively unstable S—S bond) may be mentioned mixed disulphides having the general formula:

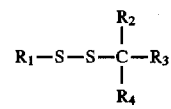

wherein $R_1$ is 2-pyridyl, and each of $R_2$, $R_3$ and $R_4$ is hydrogen or an optionally substituted lower aromatic or aliphatic hydrocarbon group. Examples of such mixed disulphides are glutathionyl-2-thiopyridyl disulphide, 2 thiocholyl 2-thiopyridyl disulphide, 2-mercaptoethanol-2-thiopyridyl disulphide and mercaptoacetate-2-thiopyridyl disulphide.

In interesting embodiments, the disulphide-reshuffling system contains glutathione, 2-mercaptoethanol or thiocholine, each of which is in admixture with its corresponding symmetrical disulphide.

The suitability of a given mixture of thiols for use as selective reducing and/or disulphide-reshuffling system in a cyclic refolding/reoxidation procedure for a specific protein product can be directly assayed by incubating ensembles of samples of a mixture of folded and misfolded protein with an array of thiol mixtures at several different concentrations of denaturant exerting weakly, intermediate or strongly denaturing effects on the protein. Following incubation, the disulphide topology in each sample is then locked by reaction with an excess of thiol-blocking reagent (e.g. Iodoacetamide) before subjecting each set of samples to SDS-PAGE under non-reducing conditions. Correctly disulphide-bridged material and material in undesired covalent topological states will appear in separate bands and will therefore allow quantitative assessment of folding state of the protein at the time of thiol-blocking, because only correctly unique disulphide-bonded topoisomer may correspond to correctly folded protein present at the end of incubation with thiol/disulphide and denaturant agents. This set of experiments allows identification of the range of denaturant levels at which a given thiol/disulphide reagent may be advantageously used as disulphide reshuffling agent, as revealed by preferential reduction and reshuffling of wrong disulphide bonds and low tendency to reduce bonds in the fully folded protein. This reagent testing procedure may be used as a general procedure for selecting advantageous reducing and/or thiol/disulphide reshuffling reagents. Example 12 demonstrates application of this analytical procedure to assess the suitability for selective reduction of misfolded forms of a model protein for 5 thiol reagents and thereby demonstrates the operability of the above procedure.

It will be understood that the above-indicated procedure for selecting suitable disulphide reshuffling systems may also be employed for selecting other compositions than mixtures of thiols. Any mixture containing suitable reducing/oxidating agents may be evaluated according to the above indicated procedure, and the composition of choice in the method of the invention will be the one which shows the highest ability to preferentially reduce incorrectly formed disulphide bridges.

Thus, a very important aspect of the invention is a method for protein refolding as described herein, wherein at least one disulphide-reshuffling system contained in liquid phase in at least one renaturing and/or denaturing step is one which is capable of reducing and/or reshuffling incorrectly formed disulphide bridges under conditions with respect to concentration of the denaturing agent at which unfolded and/or misfolded proteins are denatured and at which there is substantially no reduction and/or reshuffling of correctly formed disulphide bridges.

An interesting embodiment of the invention is a method as described above, wherein a disulphide reshuffling system is used in at least one denaturing/renaturing step and resulting in a ratio between the relative amount of reduced/reshuffled initially incorrectly formed disulphide bridges and the relative amount of reduced/reshuffled initially correctly formed disulphide bridges of at least 1.05. The ratio will preferably be higher, such as 1.1, 1.5, 2.0, 3.0, 5.0, 10, 100, 1000, but even higher ratios are realistic and are thus especially preferred according to the invention.

By the terms "initially incorrectly/correctly" with respect to the form of disulphide bridges is meant the disulphide bridging topology just before the disulphide reshuffling system exerts its effects.

It will be understood that the ratio has to be greater than 1 in order to allow the net formation of correctly formed disulphide bridges in a protein sample. Normally the ratio should be as high as possible, but even ratios which are marginally above 1 will allow the net formation of correctly formed disulphide bridges in the method of the invention, the important parameter in ensuring a high yield being the number of denaturing/renaturing cycles. Ratios just above one require that many cycles are completed before a substantive yield of correctly formed disulphide bridges is achieved, whereas high ratios only require a limited number of cycles.

In cases where only one disulphide reshuffling system is going to be employed such a disulphide-reshuffling system may according to the invention be selected by 1) incubating samples of folded and misfolded protein of the same amino acid sequence as the protein to be processed in the method of the invention with an array of disulphide-reshuffling systems at several different concentrations of a chosen denaturing agent, 2) assessing at each of the different concentrations of denaturing agent the ability of each of the disulphide reshuffling systems to reduce and/or reshuffle initially incorrectly formed disulphide bridges without substantially reducing and/or reshuffling initially correctly formed disulphide bridges as assessed by calculating the ratio between the relative amount of reduced/ reshuffled initially incorrectly formed disulphide bridges and the relative amount of reduced/reshuffled initially correctly formed disulphide bridges, and 3) selecting as the disulphide reshuffling system X, the disulphide-reshuffling system which exhibit the capability of reducing initially incorrectly formed disulphide bridges without substantially reducing and/or reshuffling initially correctly formed disulphide bridges in the widest range of concentrations of the chosen denaturing agent.

Alternatively more than one disulphide-reshuffling system may be employed, for instance in different cycles in the cyclic refolding method of the invention, but also simultaneously in the same cycles. This will e.g. be the case when it is likely or has been established by e.g. the method outlined above that the overall yield of correctly folded protein with correct disulphide bridging topology will be higher if using different disulphide-reshuffling systems in the method of the invention.

In order to calculate the above-indicated the ratio between the relative amount of reduced/reshuffled initially incorrectly formed disulphide bridges and the relative amount of reduced/reshuffled initially correctly formed disulphide bridges, the following method may be employed: to the initial mixture of reactants in step 1) is added a known amount of radioactively-labelled correctly folded protein. When the amounts of correctly and incorrectly folded protein are assessed in step 2) (for instance by non-reducing SDS-PAGE) the content of radioactivity in the correctly folded protein fraction is determined as well. Thereby an assessment of the now incorrectly folded (but initially correctly folded) protein can be determined in parallel with the determination of the total distribution of correctly/incorrectly folded protein. The above-mentioned ratio can thus be calculated as $$R = \frac{C_2 = \frac{A_2}{A_1} \cdot C_1}{U_1 - \frac{A_2}{A_1}}$$

wherein $C_1$ and $C_2$ are the initial and the final amounts of correctly folded proteins, respectively, $U_1$ is the amount of initially incorrectly folded protein, and $A_1$ and $A_2$ are the radioactivity in the initial correctly folded protein fraction and in the final correctly folded protein, respectively.

In addition to the denaturing means mentioned above, denaturing may also be achieved or enhanced by decreasing pH of the liquid phase, or by increasing pH of the liquid phase.

The polarity of the liquid phase used in the renaturing may according to the invention have been modified by the addition of a salt, a polymer and/or a hydrofluoro compound such as trifluoroethanol.

According to the invention, the denaturing and renaturing of the polypeptide molecules may also be accomplished by direct changes in physical parameters to which the polypeptide molecules are exposed, such as temperature or pressure, or these measures may be utilized to enhance or moderate the denaturing or renaturing resulting from the other measures mentioned above.

However, it will be understood that a most important practical embodiment of the method is performed by accomplishing chemical changes in the liquid phase by changing between a denaturing solution B and a renaturing solution A. In this case, the concentration of one or more denaturing compounds in B will often be adjusted after each cycle, and as one important example, the concentration of one or more denaturing compounds in B will be decremented after each cycle, but in another important embodiment, the concentration of one or more denaturing compounds in medium B is kept constant in each cycle.

This embodiment of the invention, wherein the concentration of denaturing compound(s) medium B is kept constant, is especially interesting when the most productive phase of the cycling process (with respect to correctly folded protein) has been identified, and large scale production of correctly folded protein is desired. As will be understood, the preferred concentration(s) of denaturing compound(s) of medium B in this embodiment is the concentration(s) which has been established to ensure maximum productivity in the cyclic process according to the invention.

The polypeptide molecules of the ensemble which is subjected to the method of the invention normally have a length of at least 25 amino acid residues, such as at least 30 amino acid residues or at least 50 amino acid residues. On the other hand, the polypeptide molecules of the ensemble normally have a length of at most 5000 amino acid residues, such as at most 2000 amino acid residues or at most 1000 or 800 amino acid residues.

As can be seen from example 10, the method of the invention has made possible the production of correctly folded diabody molecules (diabodies are described in Holliger et al., 1993).

An important aspect of the invention therefore relates to a method for producing correctly folded diabody molecules, wherein an initial ensemble of polypeptide molecules comprising unfolded and/or misfolded polypeptides having amino acid sequences identical to the amino acid sequences of monomer fragments of diabody molecules is subjected to a series of at least two successive cycles, each of which comprises a sequence of 1) at least one denaturing step involving conditions exerting a denaturing influence on the polypeptide molecules of the ensemble followed by 2) at least one renaturing step involving conditions having a renaturing influence on the polypeptide molecules having conformations resulting from the preceding step, the series of cycles being so adapted that a substantial fraction of the initial ensemble of polypeptide molecules is converted to a fraction of correctly folded diabody molecules.

Such a method for the correct folding of diabodies can be envisaged in any of the above-mentioned scenarios and aspects of the refolding method of the invention, that is, with respect to the choice of physical/chemical conditions as well as cycling schedules. However, an important aspect of the method for correct folding of diabodies is a method as the above-identified, wherein the polypeptide molecules are in contact with a liquid phase containing at least one disulphide reshuffling system in at least one denaturing or renaturing step. The preferred denaturing agent to be used in such a liquid phase is urea, and the preferred disulphide reshuffling system comprises glutathione as the main reducing agent.

A particular aspect of the invention relates to a polypeptide which is a proenzyme of a serine protease, but is different from any naturally occurring serine protease and, in particular, has an amino acid sequence different from that of bovine coagulation factor X (Protein Identification Resource (PIR), National Biomedical Research Foundation, Georgetown University, Medical Center, U.S.A., entry: P1;EXBO) and which can be proteolytically activated to generate the active serine protease by incubation of a solution of the polypeptide in a non-denaturing buffer with a substance that cleaves the polypeptide to liberate a new N-terminal residue, the substrate specificity of the serine protease being identical to or better than that of bovine blood coagulation factor $X_a$, as assessed by each of the ratios (k(I)/k(V) and k(III)/k(V) between cleavage rate against each of the substrates I and III:

I: Benzoyl-Val-Gly-Arg-paranitroanilide,

III: Tosyl-Gly-Pro-Arg-paranitroanilide, versus that against the substrate

V: Benzoyl-Ile-Glu-Gly-Arg-paranitroanilide at 20° C., pH=8 in a buffer consisting of 50 mM Tris, 100 mM NaCl, 1 mM $CaCl_2$, being identical to or lower than the corresponding ratio determined for bovine coagulation factor $X_a$ which is substantially free from contaminating proteases.

The characterization of the above-identified new polypeptides as serine proteases is in accordance with the normal nomenclatural use of the term serine proteases. As is well known in the art, serine proteases are enzymes which are believed to have a catalytic system consisting of an active site serine which is aligned with a histidine residue, and it is believed that the activation of the enzymes from the corresponding proenzymes is based on the liberation of a new N-terminal residue, the =-amino group of which is capable of repositioning within the polypeptide structure to form a salt bridge to an aspartic acid residue preceding an active-site serine residue, thereby forming the catalytic site characteristic of serine proteases.

The "artificial" serine proteases defined above are extremely valuable polypeptide cleaving tools for use in the method of the invention and in other methods where it is decisive to have a cleaving tool which will selectively cleave proteins, even large folded proteins. Analogously to bovine coagulation factor $X_a$, the above-defined artificial serine proteases in activated form are capable of selectively recognizing the cleaving-directing polypeptide segment SEQ ID NO: 38, but in contrast to bovine coagulation factor $X_a$, they can be established with such amino acid sequences that they can be readily produced using recombinant DNA techniques. Thus, the preferred artificial serine proteases of the invention are ones which have amino acid sequences allowing their synthesis by recombinant DNA techniques, in particular in prokaryote cells such as E. coli. As will appear from the following discussion and the examples, the artificial serine proteases of the invention, when produced in a prokaryote, may be given an enzymatically active conformation, in which the catalytically active domains are suitably exposed, by cycling according to the method of the present invention.

The quantitative test for selectivity of the artificial serine proteases involves determination of the cleavage rate, k, determined as the initial slope of a curve of absorption of light at 405 nm (absorption maximum of free paranitroaniline) versus time at 20° C.

Expressed quantitatively, the selectivity of the artificial serine proteases should be characterized by the value of (k(I)/k(V) being at most 0.06, and the value k(III)/k(V) being at most 0.5. It is preferred that (k(I)/k(V) is at most 0.05 and k(III)/k(V) is at most 0.4, and more preferred that (k(I)/k(V) is at most 0.04 and k(III)/k(V) is at most 0.15.

A more comprehensive specificity characterization involves further model substrates: thus, the substrate specificity could be assessed to be identical to or better than that of bovine blood coagulation factor $X_a$ by each of the ratios (k(I)/k(V), k(II)/k(V), k(III)/k(V) and k(IV)/k(V)) between cleavage rate against each of the substrates I–IV:

I: Benzoyl-Val-Gly-Arg-paranitroanilide,

II: Tosyl Gly Pro Lys paranitroanilide,

III: Tosyl-Gly-Pro-Arg-paranitroanilide,

IV: (d,l)Val-Leu-Arg-paranitroanilide
versus that against the substrate
V: Benzoyl-Ile-Glu-Gly-Arg-paranitroanilide
at 20° C., pH=8 in a buffer consisting of 50 mM Tris, 100 mM NaCl, 1 mM CaCl$_2$, being identical to or lower than the corresponding ratio determined for bovine coagulation factor X$_a$ which is substantially free from contaminating proteases.

Within this characterization, (k(I)/k(V) should be at most 0.06, k(II)/k(V) should be at most 0.03, k(III)/k(V) should be at most 0.5, and k(IV)/k(V)) should be at most 0.01, and it is preferred that (k(I)/k(V) is at most 0.05, k(II)/k(V) is at most 0.025, k(III)/k(V) is at most 0.4, and k(IV)/k(V) is at most 0.008, and more preferred that (k(I)/k(V) is at most 0.04, k(II)/k(V) is at most 0.015, k(III)/k(V) is at most 0.15, and k(IV)/k(V)) is at most 0.005.

The serine protease type polypeptide is defined above will normally have a molecular weight, M$_r$, of at most 70,000 and at least 15,000.

One such novel polypeptide according to the invention has the amino acid sequence SEQ ID NO: 2 or is an analogue and/or homologue thereof. Other important embodiments of the polypeptide of the invention have an amino acid sequence which is a subsequence of SEQ ID NO: 2 or an analogue and/or homologue of such a subsequence.

By the use of the term "an analogue of a polypeptide encoded by the DNA sequence" or "an analogue of a polypeptide having the amino acid sequence" is meant any polypeptide which is capable of performing as bovine coagulation factor X$_a$ in the tests mentioned above. Thus, included are also polypeptides from different sources, such as different mammals or vertebrates, which vary e.g. to a certain extent in the amino acid composition, or the post-translational modifications e.g. glycosylation or phosphorylation, as compared to the artificial serine protease described in the examples.

The term "analogue" is thus used in the present context to indicate a protein or polypeptide of a similar amino acid composition or sequence as the characteristic amino acid sequence SEQ ID NO: 2 derived from an artificial serine protease as described in Example 5, allowing for minor variations that alter the amino acid sequence e.g. deletions, site directed mutations, insertions of extra amino acids, or combinations thereof, to generate artificial serine protease analogues.

Therefore, in the present description and claims, an analogue (of a polypeptide) designates a variation of the polypeptide in which one or several amino acids may have been deleted or exchanged, and/or amino acids may have been introduced, provided the enzymatic activity with the above-defined specificity is retained, as can be assessed as described above.

With respect to homology, an analogue of a polypeptide according to the invention may have a sequence homology at the polypeptide level of at least 60% identity compared to the sequence of a fragment of SEQ ID NO: 2, allowing for deletions and/or insertions of at most 50 amino acid residues.

Such polypeptide sequences or analogues thereof which has a homology of at least 60% with the polypeptide shown in SEQ ID NO: 2 encoded for by the DNA sequence of the invention SEQ ID NO: 1 or analogues and/or homologues thereof, constitute an important embodiment of this invention.

By the term "sequence homology" is meant the identity in sequence of either the amino acids in segments of two or more amino acids in a amino acid sequence, or the nucleotides in segments of two or more nucleotides in a nucleotide sequence. With respect to polypeptides, the terms are thus intended to mean a homology between the amino acids in question between which the homology is to be established, in the match with respect to identity and position of the amino acids of the polypeptides.

The term "homologous" is thus used here to illustrate the degree of identity between the amino acid sequence of a given polypeptide and the amino sequence shown in SEQ ID NO: 2. The amino acid sequence to be compared with the amino acid sequence shown in SEQ ID NO: 2 may be deduced from a nucleotide sequence such as a DNA or RNA sequence, e.g. obtained by hybridization as defined in the following, or may be obtained by conventional amino acid sequencing methods.

Another embodiment relates to a polypeptide having an amino acid sequence from which a consecutive string of 20 amino acids is homologous to a degree of at least 40% with a string of amino acids of the same length selected from the amino acid sequence shown in SEQ ID NO: 2.

One serine protease polypeptide according to the invention has the amino acid sequence of SEQ ID NO: 2, residues 166–484, or is an analogue and/or homologue thereof.

A number of modifications of the sequences shown herein are particularly interesting: The insertion of the cleaving directing sequences SEQ ID NO: 38 or 40–42 instead of residues 230–233 in SEQ ID NO: 2, combined with exchange of cysteine residue 245 by preferably Gly, Ser or Arg in SEQ ID NO: 2. Another interesting possibility is insertion of SEQ ID NO: 38 or 40–42 instead of residues 179–182 in SEQ ID NO: 2. Quite generally, in any of the artificial serine proteases defined above, replacement of the cleaving sequence corresponding to residues 230–233 in SEQ ID NO: 2 with one of the cleavage-directing sequences defined above will give rise to extremely useful cleaving enzymes for use in the method according to the invention, in that these can be selectively and very efficiently cleaved by enzymes having the specific enzymatic activity of bovine coagulation factor X$_a$, and thus by artificial serine proteases as defined above, including by molecules identical to themselves. The latter fact means that artificial serine proteases modified by such insertion of the specific cleaving-directing sequences can be extremely effectively activated, as the first molecules cleaved and activated will be able to cleave other molecules, thus starting a chain reaction.

As mentioned above, it is a most important feature that the artificial serine proteases can be produced by recombinant DNA techniques, and hence, another important embodiment of the invention relates to a nucleic acid fragment capable of encoding an polypeptide according as defined above, in particular a DNA fragment which is capable of encoding an artificial serine protease polypeptide as defined above.

In one of its aspects, the invention relates to a nucleotide sequence encoding a polypeptide of the invention as defined above. In particular, the invention relates to a nucleotide sequence having the nucleotide sequence shown in the DNA sequence SEQ ID NO: 1 or an analogue thereof which has a homology with any of the DNA sequences shown in SEQ ID NO: 1 of at least 60%, and/or encodes a polypeptide, the amino acid sequence of which is at least 60% homologous with the amino acid sequences shown in SEQ ID NO: 2.

Generally, only coding regions are used when comparing nucleotide sequences in order to determine their internal homology.

The term "analogue" with regard to the DNA fragments of the invention is intended to indicate a nucleotide sequence which encodes a polypeptide identical or substantially identical to the polypeptide encoded by a DNA fragment of the invention. It is well known that the same amino acid may be encoded by various codons, the codon usage being related, inter alia, to the preference of the organisms in question expressing the nucleotide sequence. Thus, one of more nucleotides or codons of the DNA fragment of the invention may be exchanged by others which, when expressed, result in a polypeptide identical or substantially identical to the polypeptide encoded by the DNA fragment in question.

Furthermore, the term "analogue" is intended to allow for variations in the sequence such as substitution, insertion (including introns), addition and rearrangaement of one or more nucleotides, which variations do not have any substantial effect on the polypeptide encoded by the DNA fragment.

Thus, within the scope of the present invention is a modified nucleotide sequence which differs from the DNA sequence shown in SEQ ID NO: 1 in that at least one nucleotide has been substituted, added, inserted, deleted and/or rearranged.

The term "substitution" is intended to mean the replacement of one or more nucleotides in the full nucleotide sequence with one or more different nucleotides, "addition" is understood to mean the addition of one or more nucleotides at either end of the full nucleotide sequence, "insertion" is intended to mean the introduction of one or more nucleotides within the full nucleotide sequence, "deletion" is intended to indicate that one or more nucleotides have been deleted from the full nucleotide sequence whether at either end of the sequence or at any suitable point within it, and "rearrangement" is intended to mean that two or more nucleotide residues have been exchanged within the DNA or polypeptide sequence, respectively. The DNA fragment may, however, also be modified by mutagenesis either before or after inserting it in the organism. The DNA or protein sequence of the invention may be modified in such a way that it does not lose any of its biophysical, biochemical or biological properties, or part of such properties (one and/or all) or all of such properties (one and/or all).

An example of a specific analogue of the DNA sequence of the invention is a DNA sequence which comprises the DNA sequence shown in SEQ ID NO: 1 and particularly adapted for expression in *E. coli*. This DNA sequence is one which, when inserted in *E. coli* together with suitable regulatory sequences, results in the expression of a polypeptide having substantially the amino acid sequence shown in SEQ ID NO: 2. Thus, this DNA sequence comprises specific codons recognized by *E. coli*.

The terms "fragment", "sequence", "homologue" and "analogue", as used in the present specification and claims with respect to fragments, sequences, homologues and analogues according to the invention should of course be understood as not comprising these phenomena in their natural environment, but rather, e.g., in isolated, purified, in vitro or recombinant form.

One embodiment of the nucleic acid fragment according to the invention is a nucleic acid fragment as define above in which at least 60% of the coding triplets encode the same amino acids as a nucleic acid fragment of the nucleic acid which encodes bovine coagulation factor x, allowing for insertions and/or deletions of a most 150 nucleotides. An example of such a nucleic acid fragment is SEQ ID NO: 1, nucleotides 76–1527, and analogues and/or homologues there of. Another example is SEQ ID NO: 1, nucleotides 319–1527, and analogues and/or homologues thereof. Still another example is SEQ ID NO: 1, nucleotides 571–1527, and analogues and/or homologues thereof.

The DNA fragment described above and constituting and important aspect of the invention may be obtained directly from the genomic DNA or by isolating mRNA and converting it into the corresponding DNA sequence by using reverse transcriptase, thereby producing a cDNA. When obtaining the DNA fragment from genomic DNA, it is derived directly by screening for genomic sequences as is well known for the person skilled in the art. It can be accomplished by hybridization to a DNA probe designed on the basis of knowledge of the sequences of the invention, or the sequence information obtained by amino acid sequencing of a purified serine protease. When the DNA is of complementary DNA (cDNA) origin, it may be obtained by preparing a cDNA library with mRNA from cells containing an artificial serine protease. Hybridization can be accomplished by a DNA probe designed on the basis of knowledge of the cDNA sequence, or the sequence information obtained by amino acid sequencing of a purified artificial serine protease.

The DNA fragment of the invention or an analogue an/or homologue thereof of the invention can be replicated by fusing it with a vector and inserting the complex into a suitable microorganism or a mammalian cell line. Alternatively, the DNA fragment can be manufactured using chemical synthesis. Also, polymerase chain reaction (PCR) primers can be synthesized based on the nucleotide sequence shown in SEQ ID NO: 1. These primers can then be used to amplify the whole or a part of a sequence encoding an artificial serine protease polypeptide.

Suitable polypeptides of the invention can be produced using recombinant DNA technology. More specifically, the polypeptides may by produced by a method which comprises culturing or breeding an organism carrying the DNA sequence shown in SEQ ID NO: 1 or an analogue and/or homologue thereof of the invention under conditions leading to expression of said DNA fragment, and subsequently recovering the expressed polypeptide from the said organism.

The organism which is used for the production of the polypeptide may be a higher organism, e.g. and animal, or a lower organism, e.g. a microorganism. Irrespective of the type of organism used, the DNA fragment of the invention (described above) should be introduced in the organism either directly or with the help of a suitable vector. Alternatively, the polypeptides may be produced in the mammalian call lines by introducing the DNA fragment or an analogue and/or homologue thereof of the invention either directly or with the help of an expression vector.

The DNA fragment of the invention can also be cloned in a suitable stable expression vector and then put into a suitable cell line. The cells expressing the desired polypeptides are then selected using the conditions suitable for the vector and the cell line used. The selected cells are then grown further and form a very important and continuous source of the desired polypeptides.

Thus, another aspect of the invention relates to an expression system comprising a nucleic acid fragment as defined above and encoding an artificial serine protease polypeptide as defined above, the system comprising a 5' flanking sequence capable of mediating expression of said nucleic acid fragment. The expression system may be a replicable expression vector carrying the nucleic acid fragment, which vector is capable of replicating in a host organism or a cell line; the vector may, e.g., be a plasmid, phage, cosmid, mini-chromosome or virus; the vector may be one which, when introduced in a host cell, is integrated in the host cell genome.

Another aspect of the invention relates to an organism which carries and is capable of replicating the nucleic acid fragment as defined above. The organism may be a microorganism such as a bacterium, a yeast, a protozoan, or a cell derived from a multicellular organism such as a fungus, an insect cell, a plant cell, a mammalian cell or a cell line. Particularly interesting host organisms are microorganisms such as a bacterium of the genus Escherichia, Bacillus or Salmonella.

A further aspect of the invention relates to a method of producing an artificial serine protease polypeptide as defined above, comprising the following steps of:

1. inserting a nucleic acid fragment as defined above in an expression vector,
2. transforming a host organism as defined above with the vector produced in step a,
3. culturing the host organism produced in step b to express the polypeptide,
4. harvesting the polypeptide,
5. optionally subjecting the polypeptide to post-translational modification,
6. if necessary subjecting the polypeptide to the denaturing/renaturing cycling method according to the present invention, and
7. optionally subjecting the polypeptide to further modification to obtain an authentic polypeptide as defined above.

Further modifications of the polypeptides may for instance by accomplished by subjecting the polypeptide molecules to carboxypeptidase A or B, whereby selected amino acid residues may be removed from the C-terminus of the polypeptide molecules. This is desirable under circumstances wherein the optimal folding of the authentic polypeptide molecules only is achieved when the N-terminus is free and the cleavage directing polypeptide (such as SEQ ID NO: 37) thus is placed C-terminally of the authentic polypeptide. As is known, carboxypeptidase B cleaves sequentially from the C-terminus, and only cleaves off basic amino acids, whereas carboxypeptidase A cleaves off non-basic amino acids. By carefully designing which residue is adjoined C-terminally to the authentic polypeptide it is possible to ensure that all but the authentic polypeptide is cleaved by the carboxypeptidases. If the C-terminus of the authentic polypeptide is a basic amino acid residue one should assure that the C-terminally linked residue which is to be removed is non-basic and vice versa. It one knows the sequence of the amino acid residues from the C-terminus to the C-terminus of the authentic polypeptide it is possible to alternate between treatments with the two carboxypeptidases until only the naked, authentic polypeptide is left. A practical embodiment would be to use immobilized carboxypeptidases.

The polypeptide produced may be isolated by a method comprising one of more steps life affinity chromatography using immobilized polypeptide or antibodies reactive with said polypeptide an/or other chromatographic and electrophoretic procedures.

Also, it will be understood that a polypeptide of the invention may be prepared by the well known methods of liquid or solid phase peptide synthesis utilizing the successive coupling of the individual amino acids of the polypeptide sequence. Alternatively, the polypeptide can be synthesized by the coupling of individual amino acids forming fragments of the polypeptide sequence which are later coupled so as to result in the desired polypeptide. These methods thus constitute another interesting aspect of the invention.

The invention also relates to the use of an artificial serine protease polypeptide as defined above for cleaving polypeptides at the cleavage site for bovine coagulation factor $X_a$, the cleavage site having the amino acid sequence selected from the group consisting of SEQ ID NO: 38, SEQ ID NO: 40, SEQ ID NO: 41 and SEQ ID NO: 42, and to the use of a an artificial serine protease polypeptide as defined above for cleaving polypeptides at the cleavage site for bovine coagulation factor $X_a$, the cleavage site having a modified version of the amino acid sequence selected from the group of SEQ ID NO: 43, SEQ ID NO: 44, SEQ ID NO: 45 and SEQ ID NO: 46, which has been converted to a cleavable form as described further above.

Solvent composition is expressed in terms of a binary mixture of a non-denaturing 'buffer A' and a denaturing 'buffer B' in terms of relative content of buffer B. Three consecutive cycles are represented, each consisting of a renaturation phase 'F' and a denaturation phase 'D'. Changes in level of denaturing power of the solvent mixture during denaturation phases in consecutive cycles are denoted 'k'.

Figure 1:
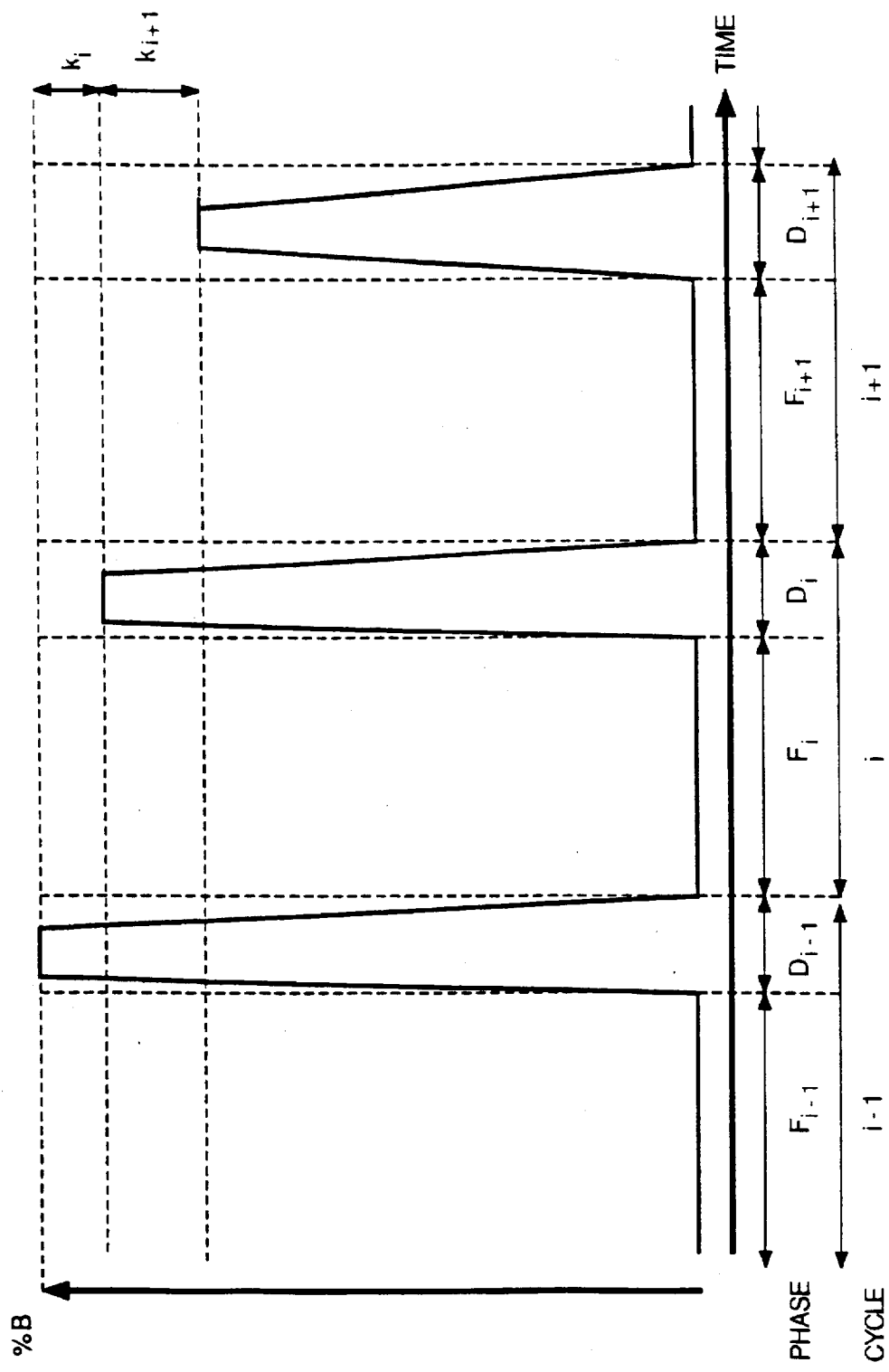
FIG. 1: Schematic representation of segment of a cyclic denaturation/renaturation time programme.
Figure 2:
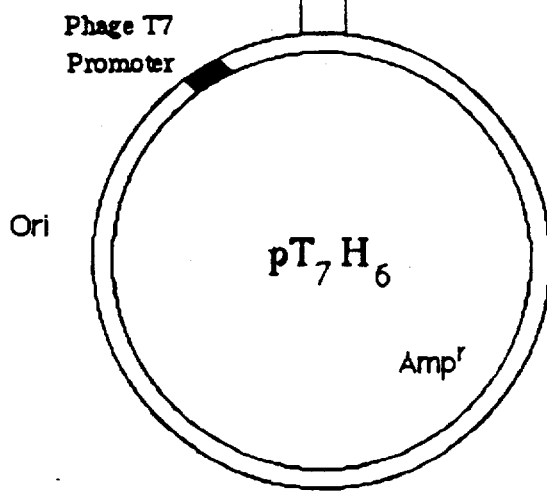

FIG. 2: Construction of the expression plasmids $pT_7H_6FX$-h$\beta$2m and $pT_7H_6FX$-m$\beta$2m.

The amplified DNA fragments containing the reading frames of human- and murine $\beta_2$-microglobulin from amino acid residues $Ile_1$ to $Met_{99}$, fused at the 5'-end to the nucleotide sequences encoding the $FX_a$ cleavage site (SEQ ID NO: 37), were out with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

FIG. 3: Amino acid sequences of human- and murine $\beta_2$-microglobulin.

A: Predicted amino acid sequence of the full length reading frame encoding human $\beta_2$-microglobulin (SEQ ID NO: 49). Amino acid residue one (Ile) in the processed mature protein is indicated. B: Predicted amino acid sequence of the full length reading frame encoding murine $\beta_2$-microglobulin (SEQ ID NO: 50). Amino acid residue one (Ile) in the processed mature protein is indicated.

Figure 4:
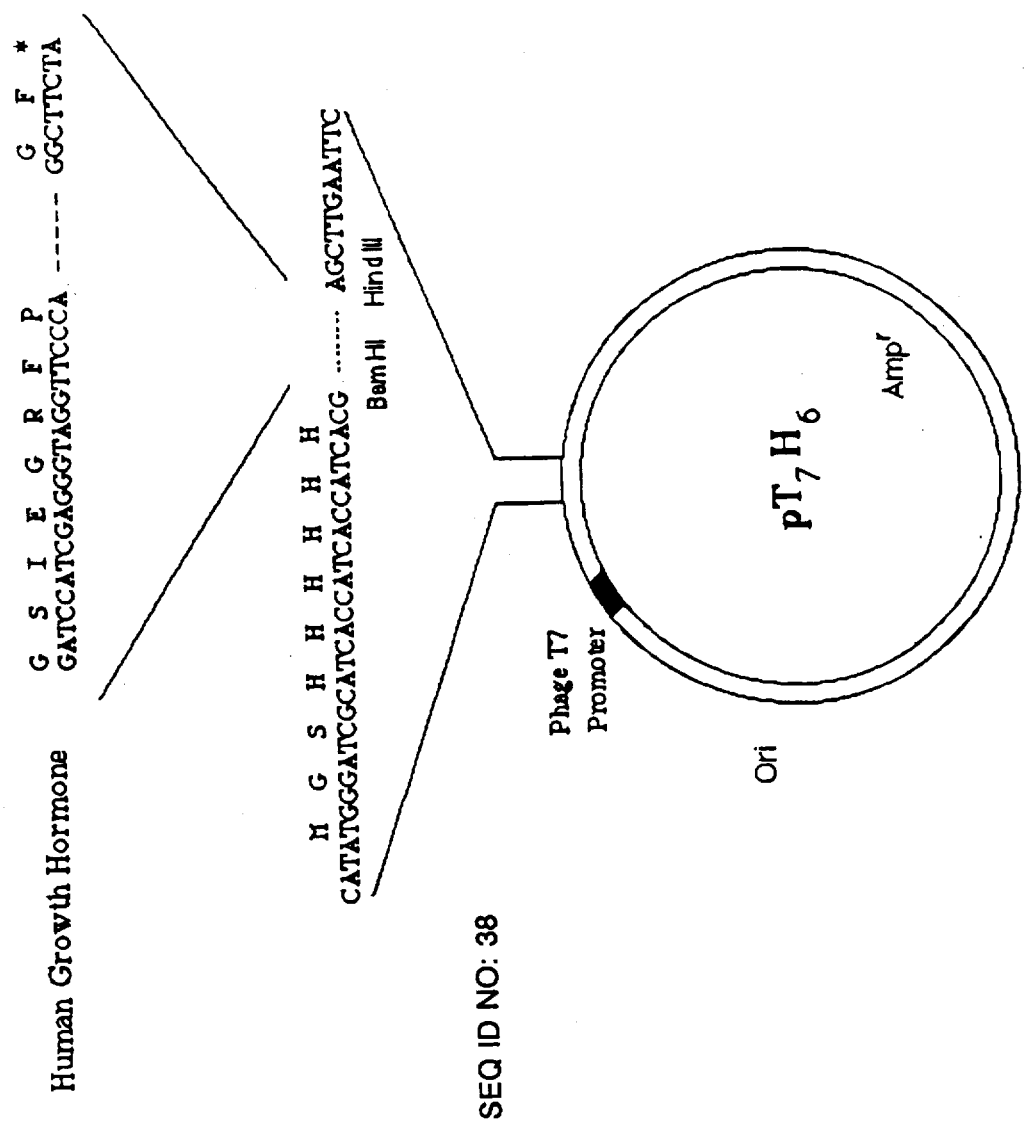

FIG. 4: Construction of the expression plasmid $pT_7H_6FX$-hGH.

The amplified DNA fragment containing the reading frame of human Growth Hormone from amino acid residues $Phe_1$ to $Phe_{191}$, fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

FIG. 5: Amino acid sequence of human Growth Hormone (Somatotropin).

The predicted amino acid sequence of the full length reading frame encoding human Growth Hormone (SEQ ID NO: 51). The first Amino acid residue in the processed mature protein ($Phe_1$) is indicated.

Figure 6:
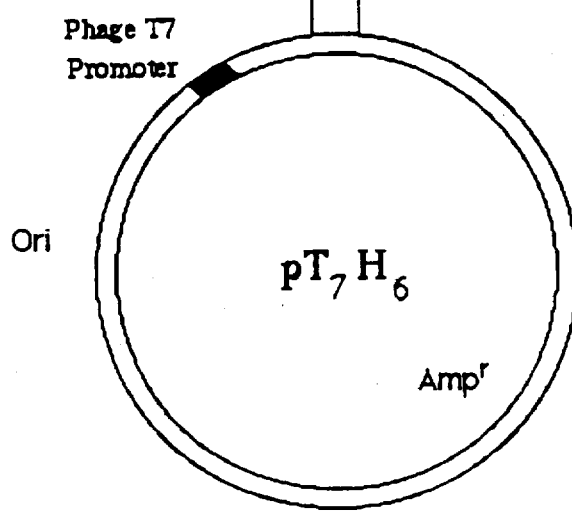

FIG. 6: Construction of the plasmids $pT_7H_6FX$-#1, #2, and #3 expressing amino acid residue no. 20 (Ala) to 109 (Arg), amino acid residue no 20 (Ala) to 190 (Ala), and amino acid residue no. 20 (Ala) to 521 (Lys) of the human $\alpha_2$-Macroglobulin Receptor Protein ($\alpha_2$MR) (SEQ ID NO: 52).

The amplified DNA fragments derived from the reading frame of the $\alpha_2$MR from #1: amino acid residue no. 20 (Ala) to 109 (Arg), #2: amino acid residue no. 20 (Ala) to 190 (Ala), and #3: amino acid residue no. 20 (Ala) to 521 (Lys), fused at the 5'-end to the nucleotide sequence encoding the $FX_a$ cleavage site IEGR (SEQ ID NO: 38), were cut with the restriction endonucleases Bam HI and Hind III (purchased from Boehringer, Germany) and ligated with $T_4$DNA ligase (purchased from Boehringer, Germany) into Bam HI and Hind III cut $pT_7H_6$ using standard procedures.

Figure 7:
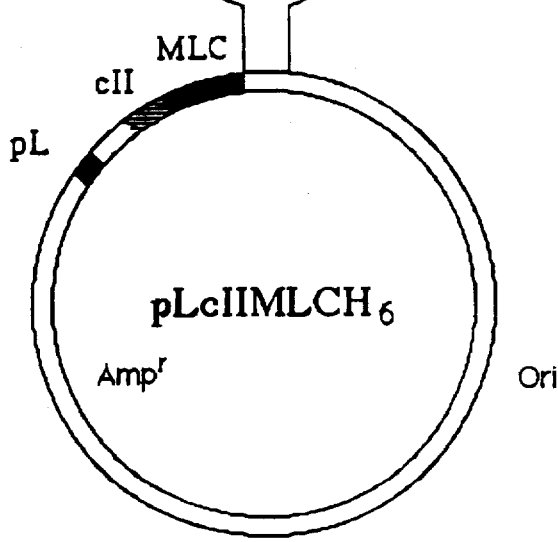

FIG. 7: Construction of the plasmids pLcIIMLCH$_6$FX-#4, #5, and #6 expressing amino acid residue no. 803 (Gly) to 1265 (Asp), amino acid residue no. 849 (Val) to 1184 (Gln), and amino acid residue no. 1184 (Gln) to 1582 (Lys) of the human $\alpha_2$-Macroglobulin Receptor Protein ($\alpha_2$MR) (SEQ ID NO: 52).

The amplified DNA fragments derived from the reading frame of the $\alpha_2$MR from #4: amino acid residue no. 803 (Gly) to 1265 (Asp), #5: amino acid residue no. 849 (Val) to 1184 (Gln), and #6: amino acid residue no. 1184 (Gln) to 1582 (Lys), fused at the 5'-end to the nucleotide sequence encoding the $FX_a$ cleavage site IEGR (SEQ ID NO: 38), were cut with the restriction endonucleases Bam HI or BcI and Hind III (purchased from Boehringer, Germany) and ligated with $T_4$ DNA ligase (purchased from Boehringer, Germany) into Bam HI and Hind III cut pLcIIMLCH$_6$FX using standard procedures.

Figure 8:
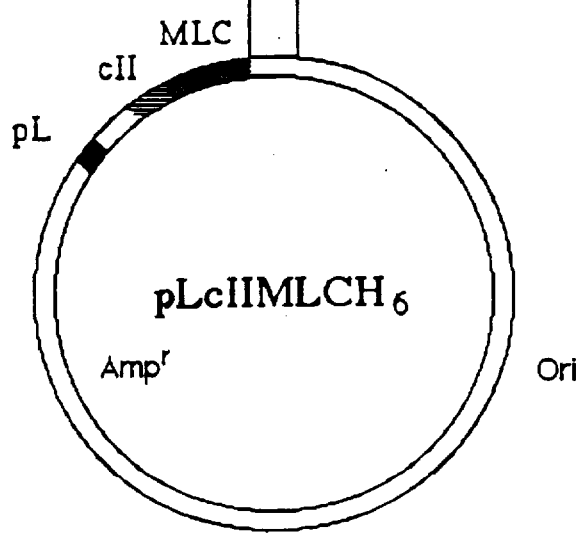

FIG. 8: Construction of the plasmids pLcIIMLCH$_6$FX-#7, #8, and #9 expressing amino acid residue no. 803 (Gly) to 1582 (Lys), amino acid residue no. 2519 (Ala) to 2941 (Ile), and amino acid residue no. 3331 (Val) to 3778 (Ile) of the human $\alpha_2$-Macroglobulin Receptor Protein ($\alpha_2$MR) (SEQ ID NO: 52).

The amplified DNA fragments derived from the reading frame of the $\alpha_2$MR from #7: amino acid residue no. 803 (Gly) to 1582 (Lys), #8: amino acid residue no. 2519 (Ala) to 2941 (Ile), and #9: amino acid residue no. 3331 (Val) to 3778 (Ile), fused at the 5'-end to the nucleotide sequence encoding the $FX_a$ cleavage site IEGR (SEQ ID NO: 38), were cut with the restriction endonucleases Bam HI and Hind III (purchased from Boehringer, Germany) and ligated with $T_4$DNA ligase (purchased from Boehringer, Germany) into Bam HI and Hind III cut pLcIIMLCH$_6$FX using standard procedures.

FIGS. 9a and 9b.: Amino acid sequence of human $\alpha_2$-Macroglobulin Receptor Protein ($\alpha_2$MR) (SEQ ID NO: 52).

The predicted amino acid sequence of the full length reading frame encoding the $\alpha_2$MR. Amino acid residues present in the recombinant proteins as N- or C-terminal residues are identified by their numbers above the $\alpha_2$MR sequence.

Figure 10:
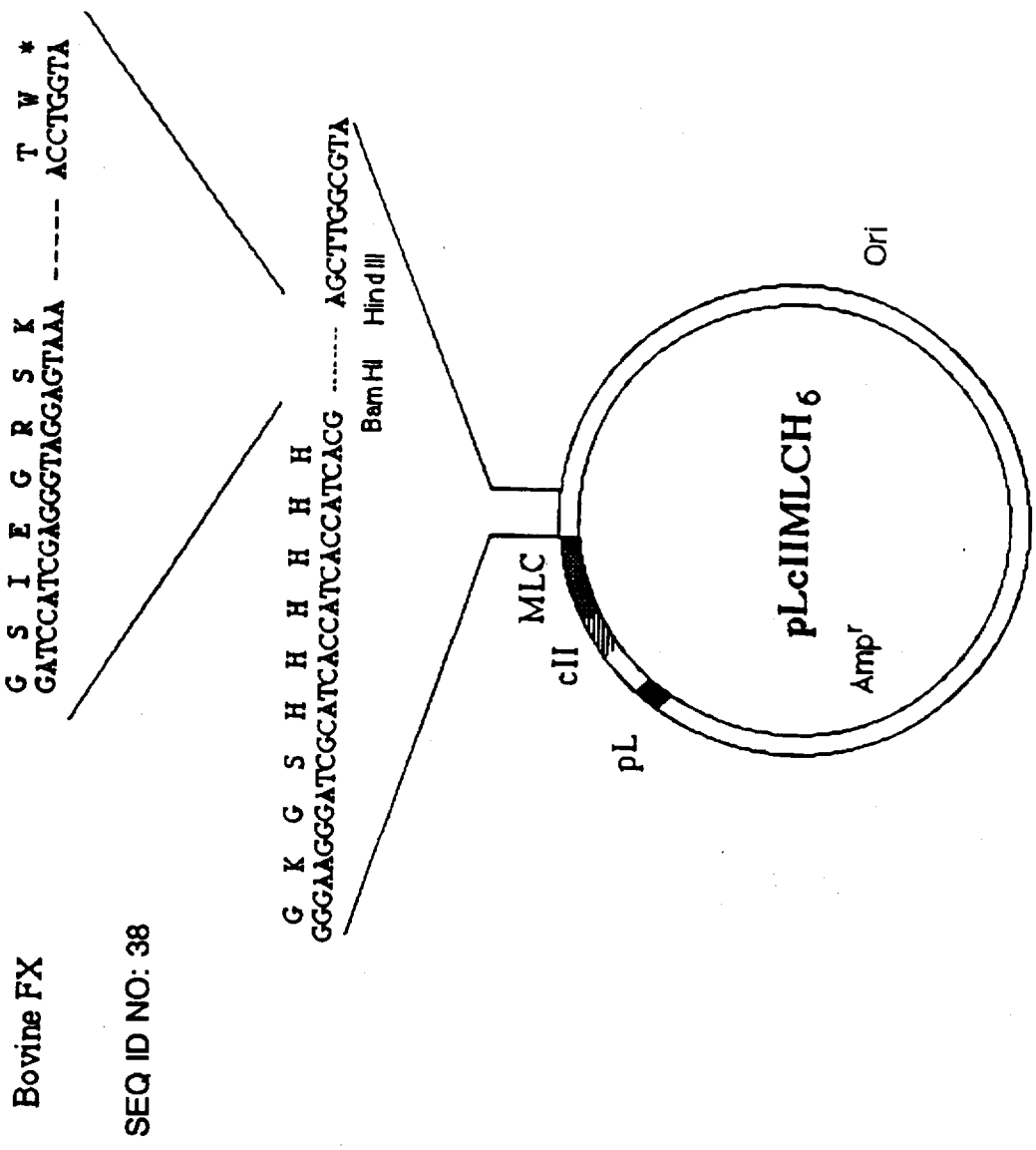

FIG. 10: Construction of the expression plasmid pLcIIMLCH$_6$FX-FX$\Delta\gamma$.

The amplified DNA fragment containing the reading frame of bovine blood coagulation Factor X from amino acid residue Ser$_{82}$ to Trp$_{484}$, (FX$\Delta\gamma$) fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut pLcIIMLCH$_6$FX using standard procedures.

Figure 11:
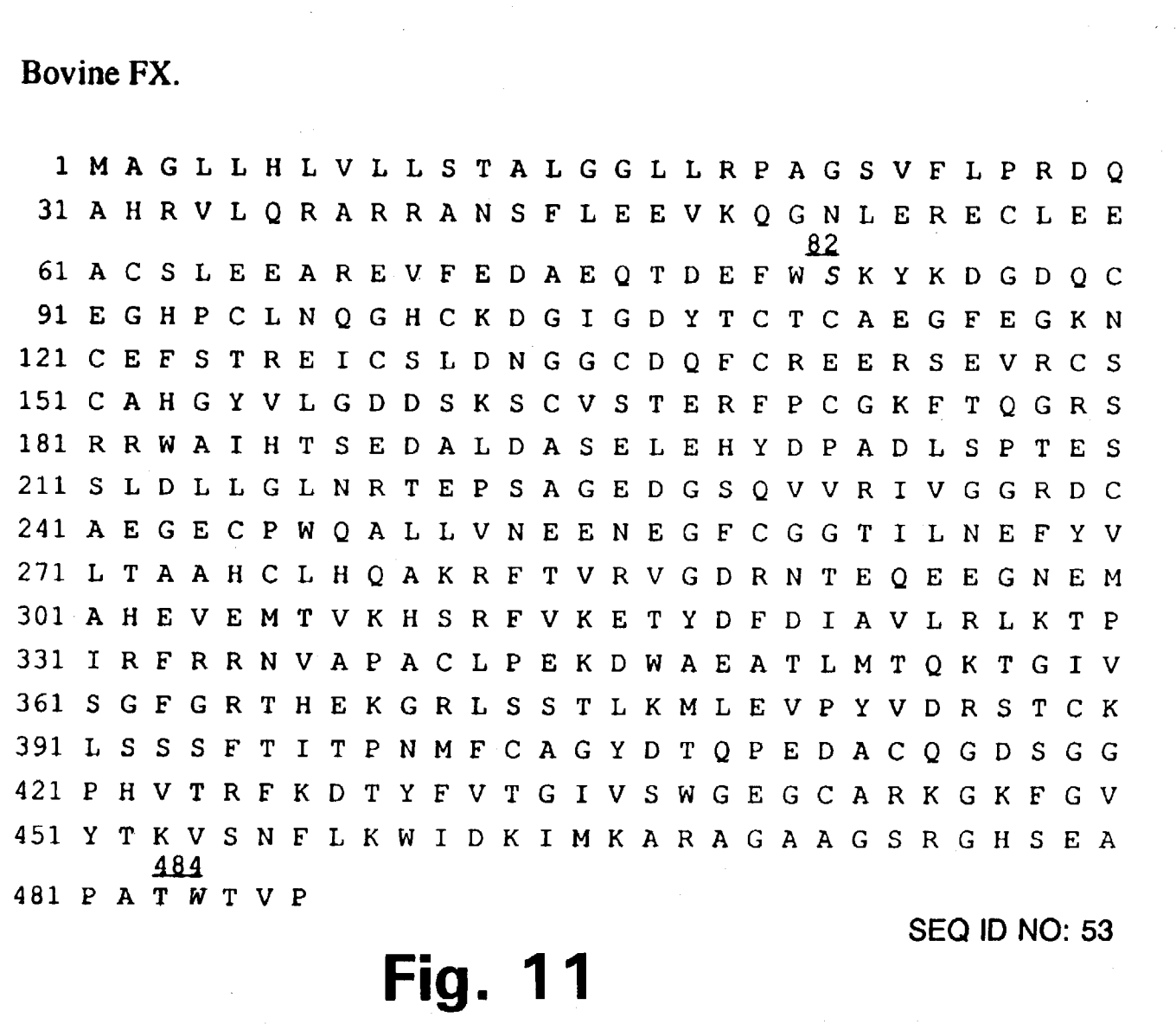

FIG. 11: Amino acid sequence of bovine blood coagulation Factor X (FX).

The predicted amino acid sequence of the full length reading frame encoding bovine FX (SEQ ID NO: 53). The N-terminal amino acid residue Ser$_{82}$ and the C terminal Trp$_{484}$ residue in the FX$\Delta\gamma$ construct are identified.

Figure 12:
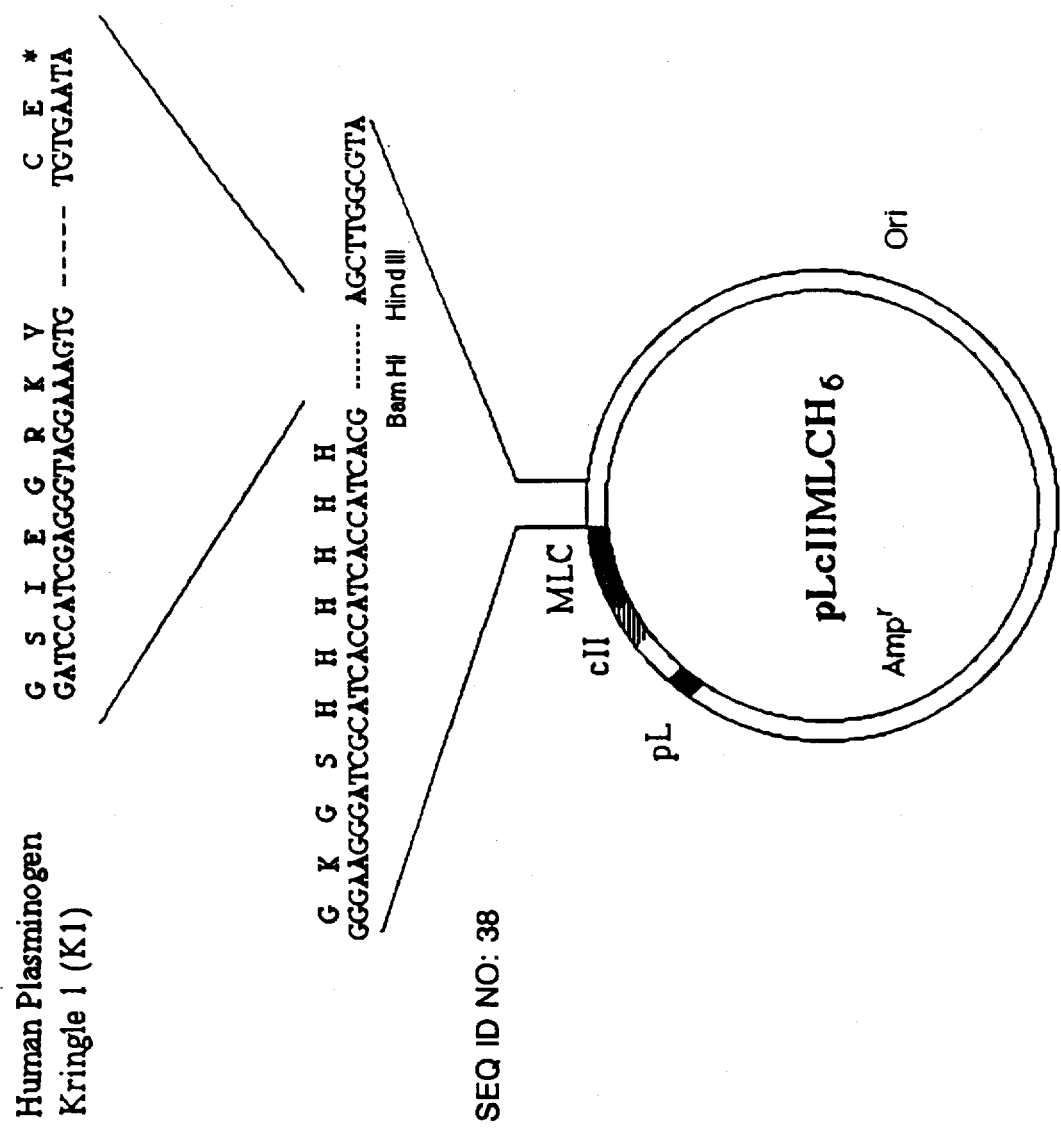

FIG. 12: Construction of the expression plasmid pLcIIMLCH$_6$FX-K1.

The amplified DNA fragment containing the reading frame of human plasminogen kringle 1 (K1) from amino acid residue Ser$_{82}$ Glu$_{162}$ (numbering as in "Glu"-plasminogen), fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut pLcIIMLCH$_6$FX using standard procedures.

Figure 13:
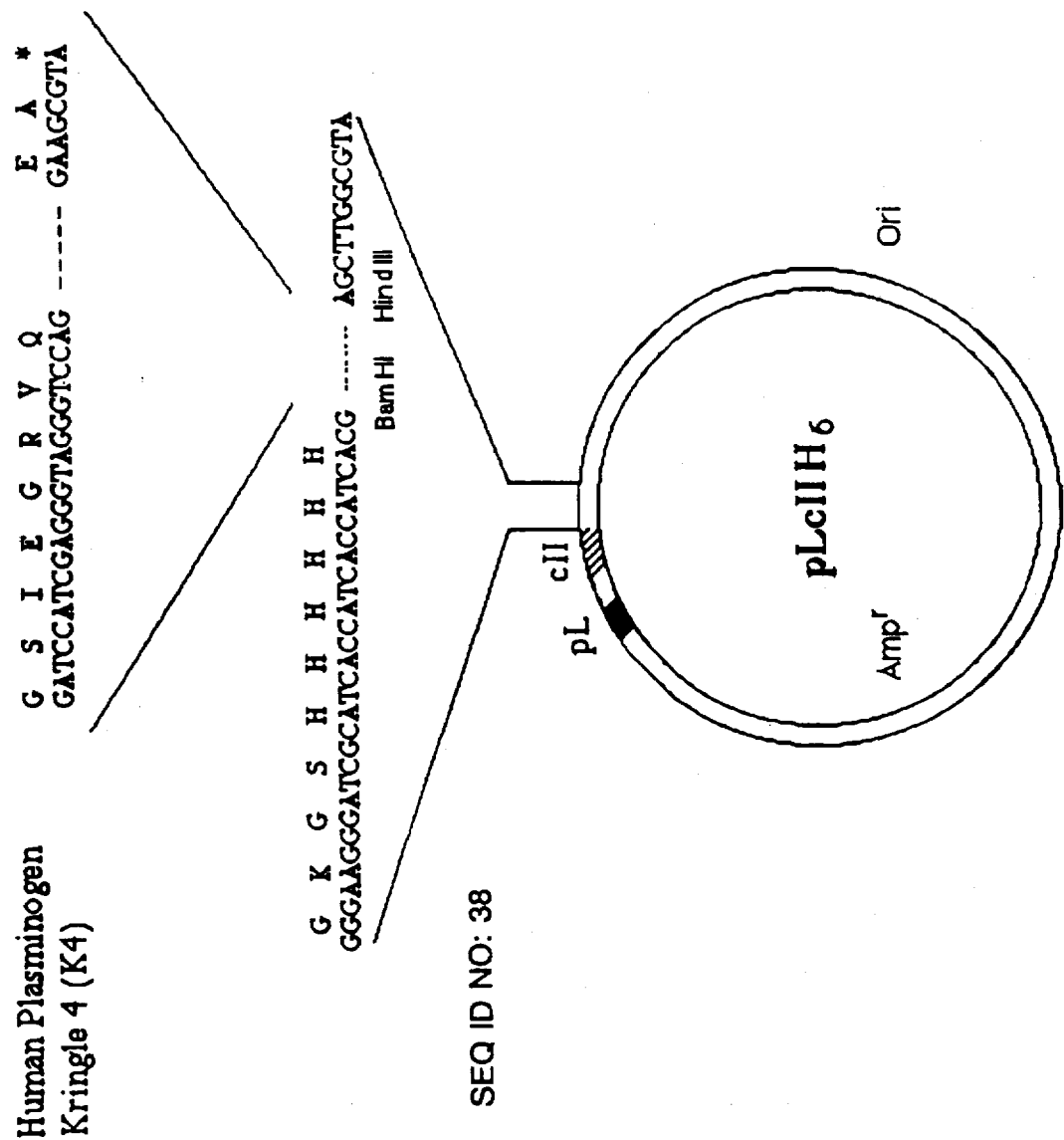

FIG. 13: Construction of the expression plasmid pLcIIH$_6$FX-K4.

The amplified DNA fragment containing the reading frame of human plasminogen kringle 4 (K4) from amino acid residue Val$_{354}$ to Ala$_{439}$ (numbering as in "Glu"-plasminogen), fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut pLcIIH$_6$Fx using standard procedures.

FIG. 14: Amino acid sequence of human "Glu"-Plasminogen (SEQ ID NO: 54). The N- and C-terminal amino acid residues in the K1 and K4 constructs are identified by their numbers in the sequence.

Figure 15:
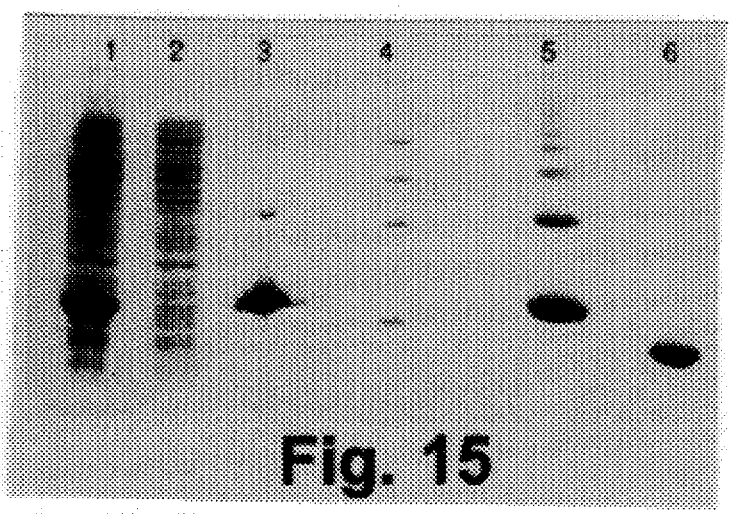

FIG. 15: SDS-PAGE analysis of production and in vitro folding of recombinant human $\beta_2$-microglobulin.

Lane 1: Crude protein extract before application to the Ni$^{2+}$NTA-agarose column (reduced sample).

Lane 2: Column flow-through during application of the crude protein extract onto the Ni$^{2+}$NTA-agarose column (reduced sample)

Lane 3: Human $\alpha_2$-microglobulin eluted from the Ni$^{2+}$ NTA-agarose column after the cyclic folding procedure by the non-denaturing elution buffer (reduced sample).

Lane 4: Protein markers (Pharmacia, Sweden): From top of gel; 94 kDa, 67 kDa, 43 kDa, 30 kDa, 20.1 kDa, and 14.4 kDa (reduced sample)

Lane 5: Same as lane 3 (non-reduced sample)

Lane 6: Recombinant human $\beta_2$-microglobulin after $FX_a$ cleavage and final purification (non-reduced sample).

Figure 16:
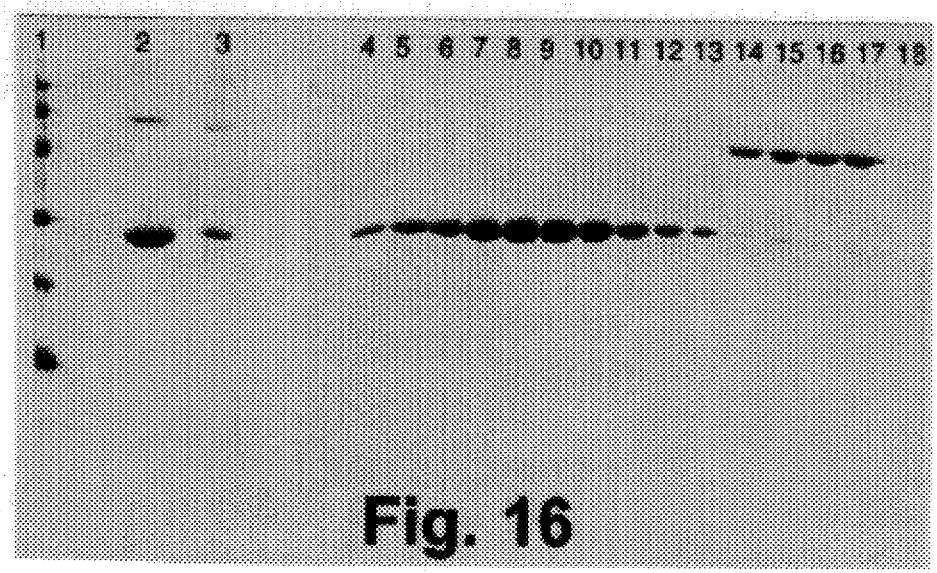

FIG. 16: SDS-PAGE analysis of in vitro folding of recombinant human Growth Hormone; hGH (Somatotropin).

Lane 1: Protein markers (Pharmacia, Sweden): From top of gel; 94 kDa, 67 kDa, 43 kDa, 30 kDa, 20.1 kDa, and 14.4 kDa (reduced sample)

Lane 2: Human hGH eluted from the Ni$^{2+}$NTA-agarose column after the cyclic folding procedure by the non-denaturing elution buffer (non-reduced sample).

Lane 3: Human hGH eluted from the Ni$^{2+}$NTA-agarose column after the cyclic folding procedure by the denaturing elution buffer B from the folding procedure (non-reduced sample).

Lane 4–18: Fractions collected during the separation of monomeric hGH-fusion protein from dimer and multimer fusion proteins after the cyclic folding procedure by ion exchange chromatography on Q-Sepharose (Pharmacia, Sweden). The monomeric protein was eluted in a peak well separated from the peak containing the dimer and multimer proteins (non-reduced samples).

FIG. 17: SDS-PAGE analysis of in vitro folding of recombinant kringle 1 and 4 from human plasminogen and recombinant fusion protein #4 derived from human $\alpha_2$-Macroglobulin Receptor Protein ($\alpha_2$MR).

Lane 1: Protein markers (Pharmacia, Sweden): From top of gel; 94 kDa, 67 kDa, 43 kDa, 30 kDa, 20.1 kDa, and 14.4 kDa (reduced sample).

Lane 2: Crude K1-fusion protein extract before application to the $Ni^{2+}$NTA-agarose column (reduced sample).

Lane 3: K1-fusion protein eluted from the $Ni^{2+}$NTA-agarose column after the cyclic folding procedure by the non-denaturing elution buffer (reduced sample).

Lane 4: Same as lane 3 (non-reduced sample).

Lane 5: Flow-through from the lysine-agarose column during application of the K1-fusion protein (non-reduced sample).

Lane 6: K1-fusion protein eluted from the lysine-agarose column (non-reduced sample).

Lane 7: K4-fusion protein eluted from the $Ni^{2+}$NTA-agarose column after the cyclic folding procedure by the non-denaturing elution buffer (reduced sample).

Lane 8: Same as lane 7 (non-reduced sample).

Lane 9: $\alpha_2$MR#4 fusion protein eluted from the $Ni^{2+}$NTA-agarose column after the cyclic folding procedure by the non-denaturing elution buffer (reduced sample).

Lane 10: Same as lane 9 (non-reduced sample).

FIG. 18: Construction of the expression plasmid $pT_7H_6FX$ $\alpha_2$MRBDv.

The amplified DNA fragment containing the reading frame of human $\alpha_2$-Macroglobulin from amino acid residues $Val_{1299}$ to $Ala_{1451}$, fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

FIG. 19: Amino acid sequence of the receptor-binding domain of human $\alpha_2$-Macroglobulin (from residue $Val_{1299}$ to $Ala_{1451}$) (SEQ ID NO: 55).

Figure 20:
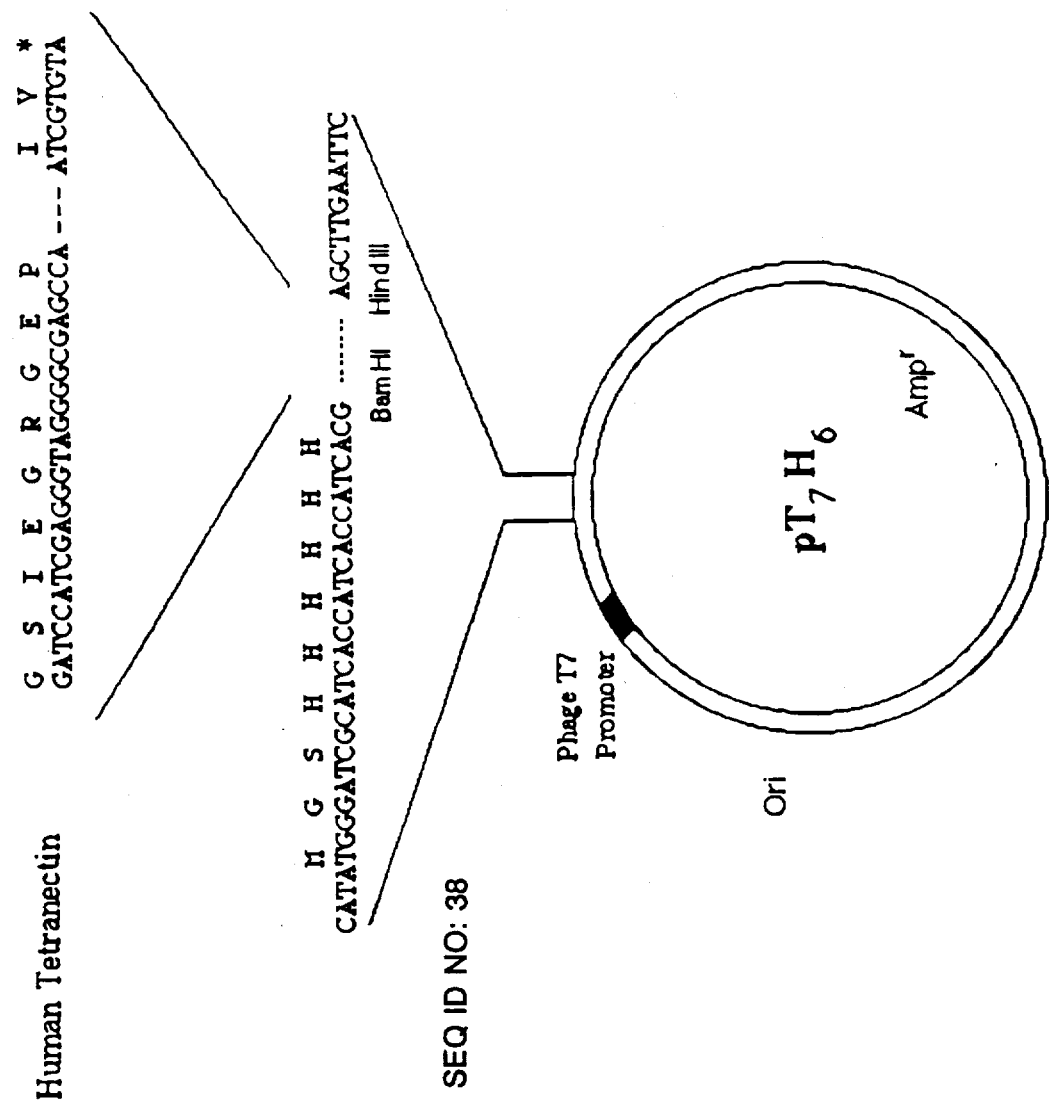

FIG. 20: Construction of the expression plasmid $pT_7H_6FX$-TETN.

The amplified DNA fragment containing the reading frame of mature monomeric human Tetranectin from amino acid residues $Glu_1$ to $Val_{181}$, fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

FIG. 21: Amino acid sequence of human monomeric Tetranectin.

The predicted amino acid sequence of the full length reading frame encoding human Tetranectin (SEQ ID NO: 56). The first Amino acid residue in the processed mature protein ($Glu_1$) is indicated.

Figure 22:
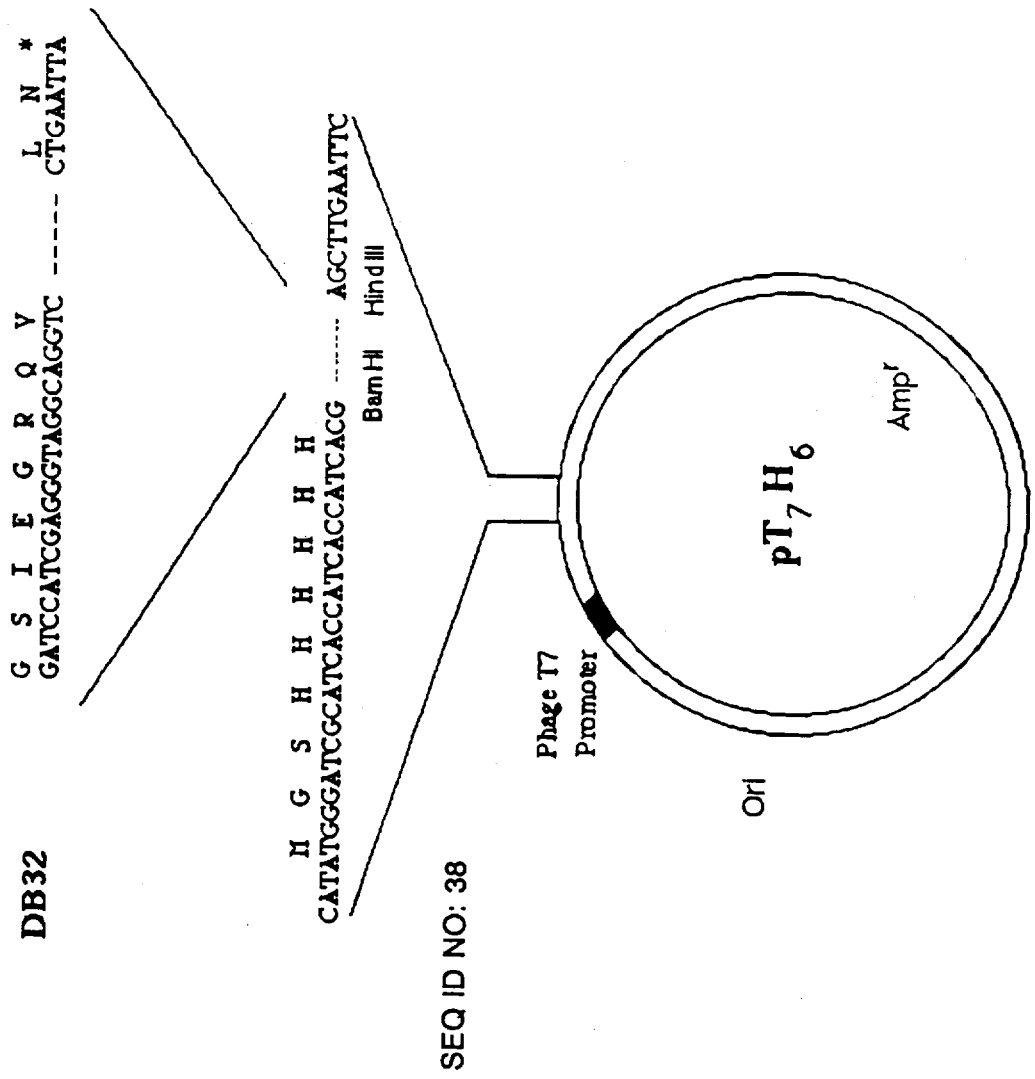

FIG. 22: Construction of the expression plasmid $pT_7H_6FX$-DB32.

The amplified DNA fragment containing the reading frame of the artificial diabody DB32 from amino acid residues $Glu_1$ to $Asn_{246}$, fused at the 5'-end to the nucleotide sequence encoding the $FX_a$ cleavage site IEGR (SEQ ID NO: 38), was cut with the restriction endonucleases Bam HI and Hind III (purchased from Boehringer, Germany) and ligated with $T_4$ DNA ligase (purchased from Boehringer, Germany) into Bam HI and Hind III cut $pT_7H_6$ using standard procedures.

FIG. 23: Amino acid sequence of the artificial diabody DB32 (SEQ ID NO: 57).

Figure 24:
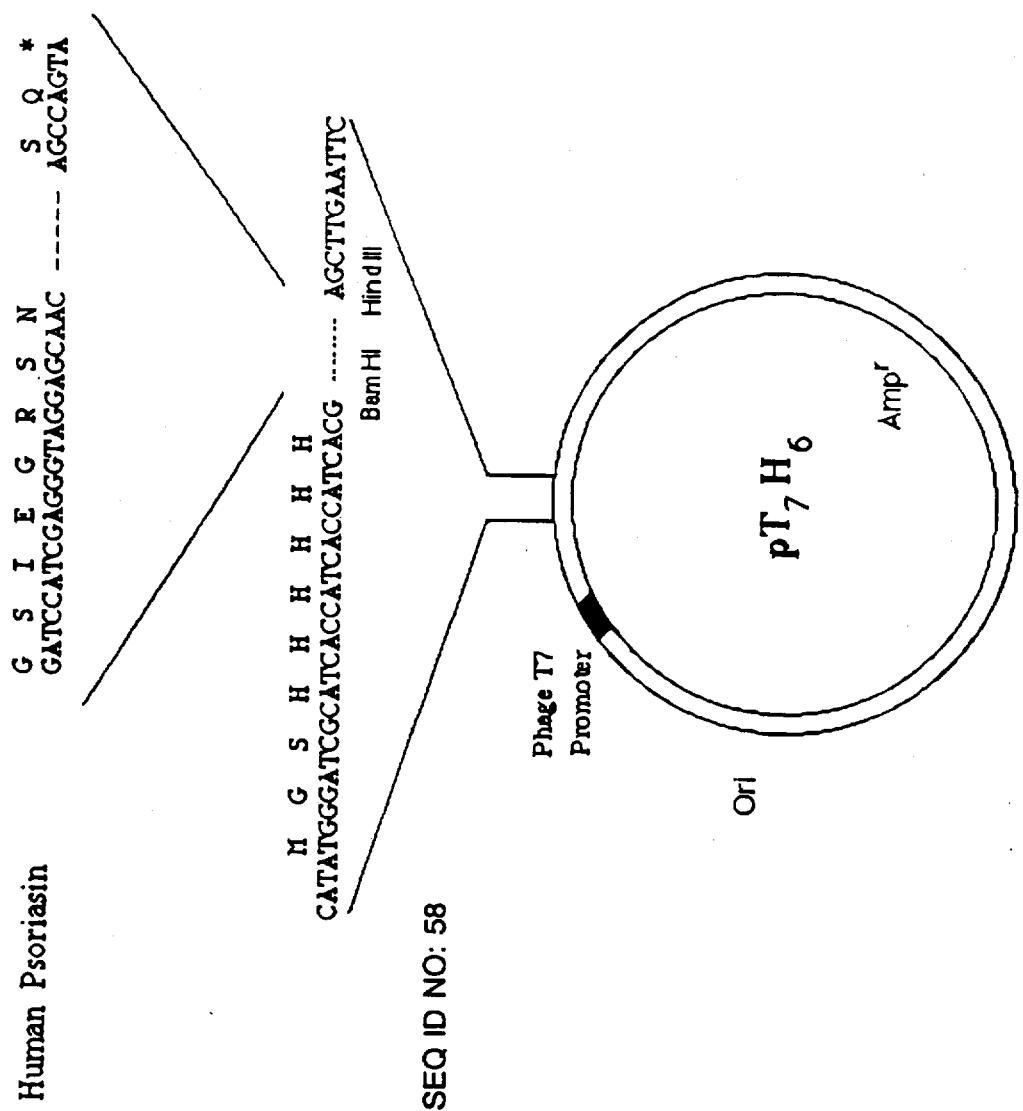

FIG. 24: The expression plasmid $pT_7H_6FX$-PS.4.

The construction of $pT_7H_6FX$-PS.4 expressing human psoriasin from amino acid residues $Ser_2$ to $Gln_{101}$ has previously been described (Hoffman, 1994).

FIG. 25: Amino acid sequence of human psoriasin.

The predicted amino acid sequence of the full length reading frame encoding human psoriasin (SEQ ID NO: 58).

Figure 26A:
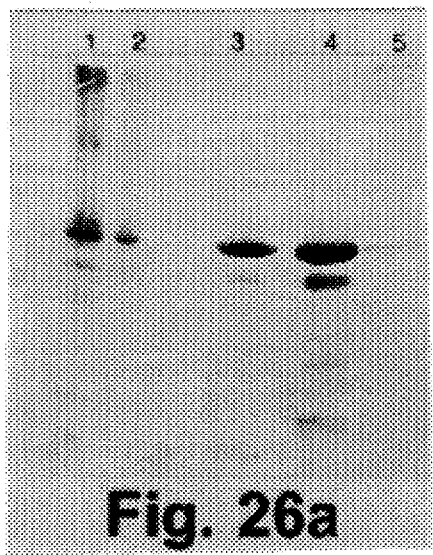
Figure 26B:
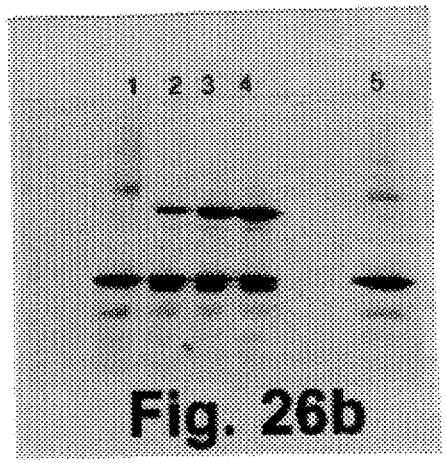

FIGS. 26a and 26b: SDS-PAGE analysis of purification and $FX_a$ cleavage of recombinant Mab 32 diabody.

FIG. 26a: Different stages of the purification

Lanes 1 and 2: Crude product from folding.

Lanes 3: Final purified Mab 32 diabody fusion protein product

Lane 4: Supernatant of crude folding product after 50-fold concentration and centrifugation.

Lane 5: Pellet from crude folding product after 50-fold concentration and centrifugation.

FIG. 26b: $FX_a$ cleavage of Mab 32 diabody fusion protein.

Lanes 1 and 5: purified Mab 32 diabody fusion protein

Lane 2: Molar ration 1:5 $Fx_a$:Mab 32 diabody fusion protein at 37° C. for 20 hours.

Lane 3: Molar ratio 1:2 $FX_a$: Mab 32 diabody fusion protein at 37° C. for 20 hours p1 Lane 4: Molar ratio 1:1 $FX_a$:Mab 32 diabody fusion protein at 37° C. for 20 hours.

Figure 27:
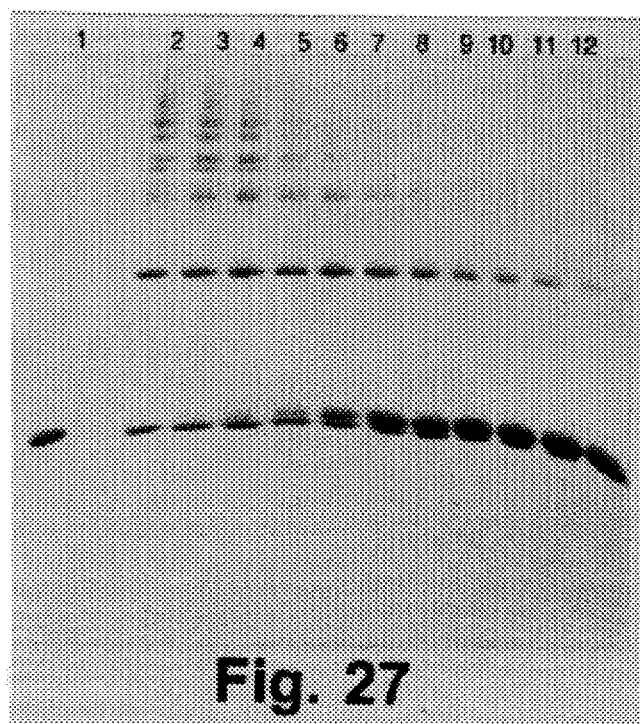

FIG. 27: Suitability of glutathione as reducing agent in cyclic refolding of human $\beta_2$-microglobulin fusion protein.

Lane 1: Reduced sample of test no. 1.
Lane 2: Non-reduced sample of test no.1.
Lane 3: Non-reduced sample of test no.2.
Lane 4: Non-reduced sample of test no.3.
Lane 5: Non-reduced sample of test no.4.
Lane 6: Non-reduced sample of test no.5.
Lane 7: Non-reduced sample of test no.6.
Lane 8: Non-reduced sample of test no.7.
Lane 9: Non-reduced sample of test no.8.
Lane 10: Non-reduced sample of test no.9.
Lane 11: Non-reduced sample of test no.10.
Lane 12: Non-reduced sample of test no.11.

Figure 28:
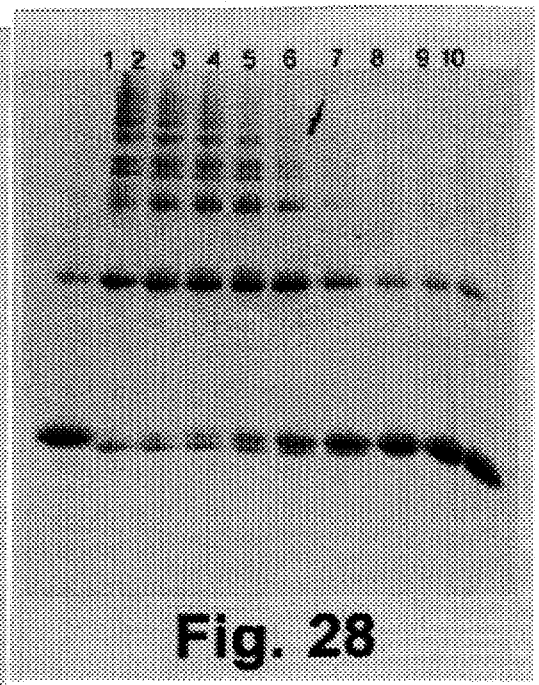

FIG. 28: Suitability of L-cystein ethyl ester as reducing agent in cyclic refolding of human $\beta_2$-microglobulin fusion protein.

Lane 1: Reduced sample of test no. 1.
Lane 2: Non-reduced sample of test no.1.
Lane 3: Non-reduced sample of test no.2.
Lane 4: Non-reduced sample of test no.3.
Lane 5: Non-reduced sample of test no.4.
Lane 6: Non-reduced sample of test no.5.
Lane 7: Non-reduced sample of test no.6.
Lane 8: Non-reduced sample of test no.7.
Lane 9: Non-reduced sample of test no.8.
Lane 10: Non-reduced sample of test no.9.

FIG. 29: Suitability of 2-Mercaptoethanol as reducing agent in cyclic refolding of human $\beta_2$-microglobulin fusion protein.

Lane 1: Reduced sample of test no. 1.
Lane 2: Non-reduced sample of test no.1.
Lane 3: Non-reduced sample of test no.2.
Lane 4: Non-reduced sample of test no.3.
Lane 5: Non-reduced sample of test no.4.
Lane 6: Non-reduced sample of test no.5.
Lane 7: Non-reduced sample of test no.6.
Lane 8: Non-reduced sample of test no.7.
Lane 9: Non-reduced sample of test no.8.
Lane 10: Non-reduced sample of test no.9.

FIG. 30: Suitability of Mercaptosuccinic acid as reducing agent in cyclic refolding of human $\beta_2$microglobulin fusion protein.

Lane 1: Non-reduced sample of test no.1.
Lane 2: Non-reduced sample of test no.2.
Lane 3: Non-reduced sample of test no.3.
Lane 4: Non-reduced sample of test no.4.
Lane 5: Non-reduced sample of test no.5.
Lane 6: Non-reduced sample of test no.6.
Lane 7: Non-reduced sample of test no.7.
Lane 8: Non-reduced sample of test no.8.
Lane 9: Non-reduced sample of test no.9.

Figure 31:
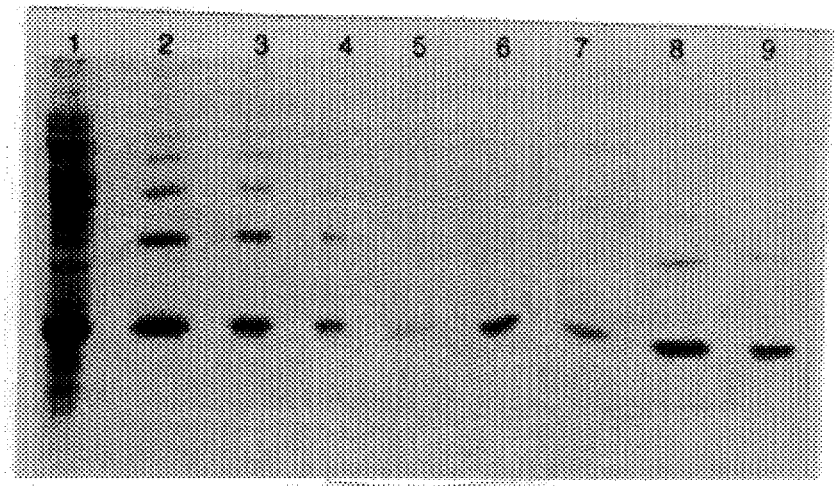

FIG. 31: Suitability of N-Acetyl-L-cysteine as reducing agent in cyclic refolding of human $\beta_2$-microglobulin fusion protein.

Lane 1: Reduced sample of test no.1.
Lane 2: Non-reduced sample of test no.1.
Lane 3: Non-reduced sample of test no.2.
Lane 4: Non-reduced sample of test no.3.
Lane 5: Non-reduced sample of test no.4.
Lane 6: Non-reduced sample of test no.5.
Lane 7: Non-reduced sample of test no.6.
Lane 8: Non-reduced sample of test no.7.
Lane 9: Non-reduced sample of test no.8.
Lane 10: Non-reduced sample of test no.9.

Figure 32:
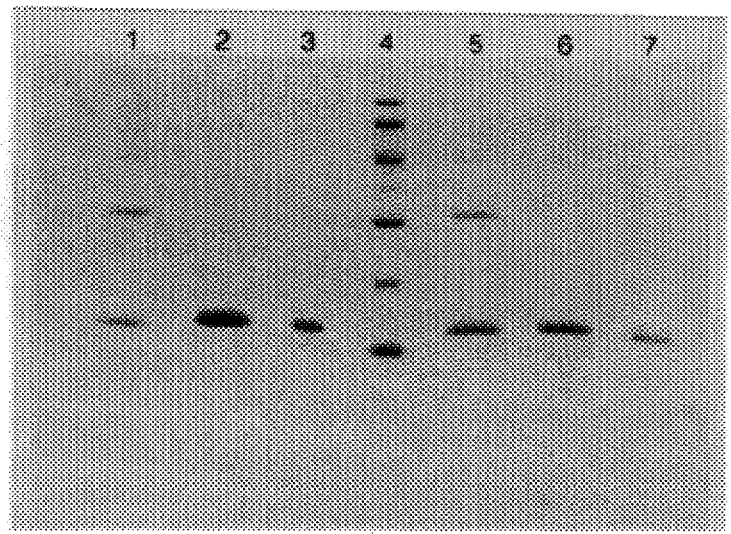

FIG. 32: SDS-PAGE analysis of cyclic refolding of human $\beta_2$-microglobulin fusion protein.

Lane 1: Crude protein extract before application to the Ni$^{2+}$NTA-agarose column (reduced sample).
Lane 2: 8 µl sample of soluble fraction of refolded h$\beta_2$m as described in EXAMPLE 1.
Lane 3: 4 µl sample of soluble fraction of refolded h$\beta_2$m as described in EXAMPLE 1.
Lane 4: 2 µl sample of soluble fraction of refolded h$\beta_2$m as described in EXAMPLE 1.
Lane 5: 8 µl sample of insoluble fraction of refolded h$\beta_2$m as described in EXAMPLE 1.
Lane 6 and 7: h$\beta_2$m final product after purification by ion exchange chromatography.
Lane 8 and 9: Refolded h$\beta_2$m after optimized refolding protocol as described in EXAMPLE 13.

Figure 33:
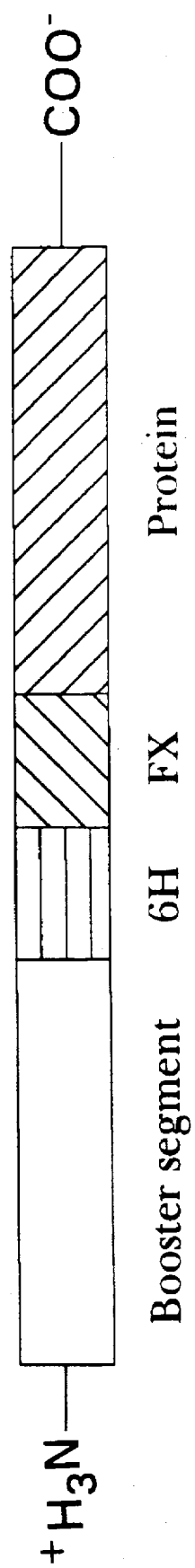

FIG. 33: SDS-PAGE analysis of refolding of human $\beta_2$-microglobulin fusion protein by buffer step and linear gradient.

Lane 1: Sample from soluble fraction of refolded h$\beta_2$m, folded by the buffer step protocol as described in EXAMPLE 13.
Lane 2 and 3: Sample of insoluble fraction of refolded h$\beta_2$m, folded by the buffer step protocol as described in EXAMPLE 13.
Lane 4: Protein molecular weight markers (Pharmacia, Sweden): From top of gel; 94 kDa, 67 kDa, 43 kDa, 30 kDa, 20.1 kDa, and 14.4 kDa (reduced sample).
Lane 5: Sample of soluble fraction of refolded h$\beta_2$m, folded by the linear gradient protocol as described in EXAMPLE 13
Lane 6 and 7: Sample of insoluble fraction of refolded h$\beta_2$m, folded by the linear gradient protocol as described in EXAMPLE 13.

Figure 34:
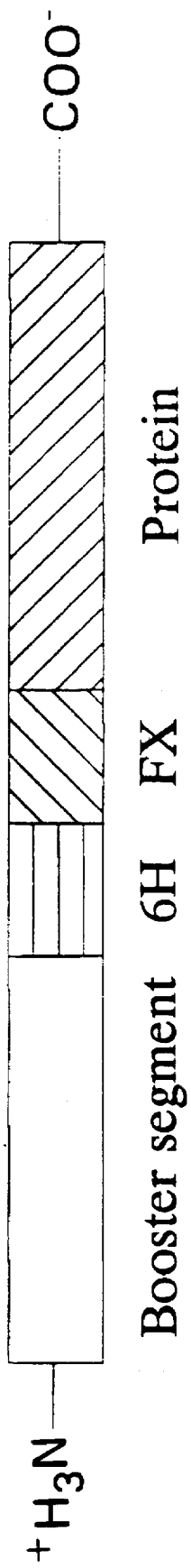

FIG. 34: The general scheme of the design of the fusion proteins described in the examples.

In the N-terminal end of the fusion protein is optionally inserted a "booster segment" enhancing the level of expression of the fusion protein in the cell expressing the DNA encoding the fusion protein. C-terminally to this, the "6H" indicates the 6 histidinyl residues which constitute an ion chelating site used as a "affinity handle" during purification and refolding of the fusion proteins. The "FX" at the C-terminal of the 6-histidinyl site is the FX$_a$ cleavage site. Finally, the part of the fusion protein denoted "protein" represents the protein which is going to be refolded according to the method of the invention.

EXAMPLES

Example 1 to 11 given in this section, which are used to exemplify the "cyclic folding procedure", all describe the process of folding a recombinant cleavable hybrid protein (fusion protein) produced in E. coli, purified from a crude protein extract and subjected to folding without further purification by one general procedure.

The nucleotide sequence encoding the recombinant protein, which is to be produced, is a the 5'-end used to a nucleotide sequence encoding an amino acid sequence specifying a FX$_a$ cleavage site (FX), in turn linked N-terminally to a segment containing six histidinyl residues (SEQ ID NO: 47). The linking of the FX$_a$ cleavage site is normally achieved during a Polymerase Chain Reaction, wherein the 5'-terminal primer comprises nucleotides encoding this sequence. The linking of the six histidinyl residues is normally obtained by employing a vector which comprises a nucleotide fragment encoding SEQ ID NO: 47. The six histidinyl residues constitute a metal ion chelating site, which is utilized as affinity handle during purification of the fusion protein and subsequently as the point of contact to the solid matrix during the cyclic folding process. Occasionally 'booster segments'(e.g. a segment derived from the N-terminus of the $\lambda$cII protein in some cases followed by a segment derived from myosin light chain) are inserted N-terminal to the affinity handle in order to improve the level of expression of the fusion protein in E. coli.

The fusion proteins are all designed according to the same general scheme (cf. FIG. 34). The presence of booster segments, affinity handle and FX$_a$ cleavage site might complicate refolding of the recombinant protein of interest. Furthermore, the cyclic folding process is initiated immediately after the affinity purification of the fusion protein. This means that fusion protein material, which has been partially degraded by the E. coli host, is retained on the affinity matrix in addition to the full length fusion protein column. This degraded fusion protein may well interfere severely with refolding of the full-length fusion protein, thereby reducing the apparent efficiency of the process. The folding efficiency results reported in Examples 1 to 11 therefore cannot directly be compared to the efficiency of the process of refolding a purified fusion protein.

Examples 1 to 11 describe the refolding procedure for 21 different proteins, protein domains or domain-clusters, ranging from a size of 82 amino acids (K1, Example 6) to 780 amino acids ($\alpha_2$MR#7, Example 4), and the number of disulphide bridges in the proteins ranges from zero ($\alpha_2$MRAP, Example 3) to 33 ($\alpha_2$MR#4, Example 4) and 36 ($\alpha_2$MR#7, Example 4).

The efficiency of the refolding of the proteins ranges from 15 to 95%, and the yield of active protein lies in the order on 10–100 mg for refolding on a 40 ml Ni+NTA-agarose column (NTA denotes a substituted nitrilotriacetic acid).

The following tables 1–5 demonstrate the gradient profiles used in the examples. "Time" is given in minutes and "flow" in ml/min.

TABLE 1

| Step | Time | Flow | % A | % B | Step | Time | Flow | %A | % B |
|---|---|---|---|---|---|---|---|---|---|
| 1 | 0 | 2 | 100 | 0 | 61 | 900 | 2 | 100 | 0 |
| 2 | 45 | 2 | 100 | 0 | 62 | 945 | 2 | 100 | 0 |
| 3 | 46 | 2 | 0 | 100 | 65 | 946 | 2 | 60 | 40 |
| 4 | 52 | 2 | 0 | 100 | 64 | 952 | 2 | 60 | 40 |
| 5 | 60 | 2 | 100 | 0 | 65 | 960 | 2 | 100 | 0 |
| 6 | 105 | 2 | 100 | 0 | 66 | 1005 | 2 | 100 | 0 |
| 7 | 106 | 2 | 4 | 96 | 67 | 1006 | 2 | 62 | 38 |
| 8 | 113 | 2 | 4 | 96 | 68 | 1012 | 2 | 62 | 38 |
| 9 | 120 | 2 | 100 | 0 | 69 | 1020 | 2 | 100 | 0 |
| 10 | 165 | 2 | 100 | 0 | 70 | 1065 | 2 | 100 | 0 |
| 11 | 166 | 2 | 8 | 92 | 71 | 1066 | 2 | 64 | 36 |
| 12 | 172 | 2 | 8 | 92 | 72 | 1072 | 2 | 64 | 36 |
| 13 | 180 | 2 | 100 | 0 | 75 | 1080 | 1 | 100 | 0 |
| 14 | 225 | 2 | 100 | 0 | 74 | 1125 | 2 | 100 | 0 |
| 15 | 226 | 2 | 12 | 88 | 75 | 1126 | 2 | 66 | 34 |
| 16 | 232 | 2 | 12 | 88 | 76 | 1132 | 2 | 66 | 34 |
| 17 | 240 | 2 | 100 | 0 | 77 | 1140 | 2 | 100 | 0 |
| 18 | 285 | 2 | 100 | 0 | 78 | 1185 | 2 | 100 | 0 |
| 19 | 286 | 2 | 16 | 84 | 79 | 1186 | 2 | 68 | 32 |
| 20 | 202 | 2 | 16 | 84 | 80 | 1192 | 2 | 68 | 32 |
| 21 | 300 | 2 | 100 | 0 | 81 | 1200 | 2 | 100 | 0 |
| 22 | 345 | 2 | 100 | 0 | 82 | 1245 | 2 | 100 | 0 |
| 23 | 346 | 2 | 20 | 80 | 83 | 1246 | 2 | 70 | 30 |
| 24 | 352 | 2 | 20 | 80 | 84 | 1252 | 2 | 70 | 30 |
| 25 | 360 | 2 | 100 | 0 | 05 | 1260 | 2 | 100 | 0 |
| 26 | 405 | 2 | 100 | 0 | 86 | 1305 | 2 | 100 | 0 |
| 27 | 406 | 2 | 24 | 76 | 87 | 1306 | 2 | 72 | 28 |
| 28 | 412 | 2 | 24 | 76 | 88 | 1312 | 2 | 72 | 28 |
| 29 | 120 | 2 | 100 | 0 | 89 | 1319 | 2 | 100 | 0 |
| 30 | 465 | 2 | 100 | 0 | 90 | 1364 | 2 | 100 | 0 |
| 31 | 466 | 2 | 28 | 72 | 91 | 1365 | 2 | 74 | 26 |
| 32 | 172 | 2 | 28 | 72 | 92 | 1371 | 2 | 74 | 26 |
| 33 | 480 | 2 | 100 | 0 | 93 | 1378 | 2 | 100 | 0 |
| 34 | 525 | 2 | 100 | 0 | 94 | 1423 | 2 | 100 | 0 |
| 35 | 526 | 2 | 32 | 68 | 93 | 1424 | 2 | 76 | 24 |
| 36 | 532 | 2 | 32 | 68 | 96 | 1430 | 2 | 76 | 24 |
| 37 | 540 | 2 | 100 | 0 | 97 | 1437 | 2 | 100 | 0 |
| 38 | 585 | 2 | 100 | 0 | 98 | 1482 | 2 | 100 | 0 |
| 39 | 586 | 2 | 36 | 64 | 99 | 1483 | 2 | 78 | 22 |
| 40 | 592 | 2 | 36 | 64 | 100 | 1489 | 2 | 78 | 22 |
| 41 | 600 | 2 | 100 | 0 | 101 | 1496 | 2 | 100 | 0 |
| 42 | 645 | 2 | 100 | 0 | 102 | 1541 | 2 | 100 | 0 |
| 43 | 646 | 2 | 40 | 60 | 103 | 1542 | 2 | 80 | 20 |
| 44 | 652 | 2 | 40 | 60 | 104 | 1540 | 2 | 80 | 20 |
| 45 | 660 | 2 | 100 | 0 | 105 | 1555 | 2 | 100 | 0 |
| 45 | 705 | 2 | 100 | 0 | 106 | 1556 | 2 | 82 | 18 |
| 47 | 706 | 2 | 44 | 56 | 107 | 1502 | 2 | 82 | 18 |
| 48 | 713 | 2 | 44 | 56 | 108 | 1569 | 2 | 100 | 0 |
| 49 | 720 | 2 | 100 | 0 | 109 | 1614 | 1 | 100 | 0 |
| 50 | 765 | 2 | 100 | 0 | 110 | 1615 | 2 | 84 | 16 |
| 51 | 766 | 2 | 48 | 52 | 111 | 1621 | 2 | 84 | 16 |
| 52 | 772 | 2 | 48 | 52 | 112 | 1628 | 2 | 100 | 0 |
| 53 | 780 | 2 | 100 | 0 | 113 | 1673 | 2 | 100 | 0 |
| 54 | 825 | 2 | 100 | 0 | 114 | 1674 | 2 | 88 | 12 |
| 55 | 826 | 2 | 52 | 48 | 115 | 1732 | 2 | 88 | 12 |
| 56 | 832 | 2 | 52 | 48 | 116 | 1733 | 2 | 100 | 0 |
| 57 | 840 | 2 | 100 | 0 | 117 | 1778 | 2 | 100 | 0 |
| 58 | 885 | 2 | 100 | 0 | | | | | |
| 59 | 886 | 2 | 56 | 44 | | | | | |
| 60 | 892 | 2 | 56 | 44 | | | | | |

TABLE 2

| Step | Time | Flow | % A | % B | Step | Time | Flow | %A | % B |
|---|---|---|---|---|---|---|---|---|---|
| 1 | 0 | 2 | 100 | 0 | 49 | 720 | 2 | 100 | 0 |
| 2 | 45 | 2 | 100 | 0 | 50 | 765 | 2 | 100 | 0 |
| 3 | 46 | 2 | 0 | 100 | 51 | 766 | 2 | 74 | 26 |
| 4 | 52 | 2 | 0 | 100 | 52 | 772 | 2 | 74 | 26 |
| 5 | 60 | 2 | 100 | 0 | 53 | 780 | 2 | 100 | 0 |
| 6 | 105 | 2 | 100 | 0 | 54 | 825 | 2 | 100 | 0 |
| 7 | 106 | 2 | 8 | 92 | 55 | 826 | 2 | 76 | 24 |
| 8 | 113 | 2 | 8 | 92 | 56 | 832 | 2 | 76 | 24 |
| 9 | 120 | 2 | 100 | 0 | 57 | 840 | 2 | 100 | 0 |
| 10 | 165 | 2 | 100 | 0 | 58 | 885 | 2 | 100 | 0 |
| 11 | 166 | 2 | 20 | 80 | 59 | 886 | 2 | 78 | 22 |
| 12 | 172 | 2 | 20 | 80 | 60 | 892 | 2 | 78 | 22 |
| 13 | 180 | 2 | 100 | 0 | 61 | 900 | 2 | 100 | 0 |
| 14 | 225 | 2 | 100 | 0 | 62 | 945 | 2 | 100 | 0 |
| 15 | 226 | 2 | 28 | 72 | 63 | 946 | 2 | 80 | 20 |
| 16 | 232 | 2 | 28 | 72 | 64 | 952 | 2 | 80 | 20 |
| 17 | 240 | 2 | 100 | 0 | 65 | 960 | 2 | 100 | 0 |
| 18 | 285 | 2 | 100 | 0 | 66 | 1005 | 2 | 100 | 0 |
| 19 | 286 | 2 | 34 | 66 | 67 | 1006 | 2 | 82 | 18 |
| 20 | 292 | 2 | 34 | 66 | 68 | 1012 | 2 | 82 | 18 |
| 21 | 300 | 2 | 100 | 0 | 69 | 1020 | 2 | 100 | 0 |
| 22 | 345 | 2 | 100 | 0 | 70 | 1065 | 2 | 100 | 0 |
| 23 | 348 | 2 | 47 | 58 | 71 | 1066 | 2 | 84 | 16 |
| 24 | 352 | 2 | 42 | 58 | 72 | 1072 | 2 | 84 | 16 |
| 25 | 360 | 2 | 100 | 0 | 73 | 1080 | 2 | 100 | 0 |
| 26 | 405 | 2 | 100 | 0 | 74 | 1125 | 2 | 100 | 0 |
| 27 | 406 | 2 | 50 | 50 | 75 | 1126 | 2 | 86 | 14 |
| 28 | 412 | 2 | 50 | 50 | 76 | 1132 | 2 | 86 | 14 |
| 29 | 420 | 2 | 100 | 0 | 77 | 1140 | 2 | 100 | 0 |
| 30 | 465 | 2 | 100 | 0 | 78 | 1185 | 2 | 100 | 0 |
| 31 | 466 | 2 | 54 | 46 | 79 | 1186 | 2 | 88 | 12 |
| 32 | 472 | 2 | 54 | 46 | 80 | 1192 | 2 | 88 | 12 |
| 33 | 480 | 2 | 100 | 0 | 81 | 1200 | 2 | 100 | 0 |
| 34 | 525 | 2 | 100 | 0 | 82 | 1245 | 2 | 100 | 0 |
| 35 | 526 | 2 | 58 | 42 | 83 | 1246 | 2 | 90 | 10 |
| 36 | 532 | 2 | 58 | 42 | 84 | 1252 | 2 | 90 | 10 |
| 37 | 540 | 2 | 100 | 0 | 85 | 1260 | 2 | 100 | 0 |
| 38 | 585 | 2 | 100 | 0 | 86 | 1305 | 2 | 100 | 0 |
| 39 | 586 | 2 | 62 | 38 | 87 | 1306 | 2 | 95 | 5 |
| 40 | 592 | 2 | 62 | 38 | 88 | 1312 | 2 | 95 | 5 |
| 41 | 600 | 2 | 100 | 0 | 89 | 1319 | 2 | 100 | 0 |
| 42 | 645 | 2 | 100 | 0 | 90 | 1364 | 2 | 100 | 0 |
| 43 | 646 | 2 | 66 | 34 | | | | | |
| 44 | 652 | 2 | 66 | 34 | | | | | |
| 45 | 660 | 2 | 100 | 0 | | | | | |
| 46 | 705 | 2 | 100 | 0 | | | | | |
| 47 | 706 | 2 | 70 | 30 | | | | | |
| 48 | 713 | 2 | 70 | 30 | | | | | |

TABLE 3

| Step | Time | Flow | % A | % B | Step | Time | Flow | %A | % B |
|---|---|---|---|---|---|---|---|---|---|
| 1 | 0,0 | 1,0 | 0,0 | 100,0 | 25,0 | 420,5 | 1,0 | 60,0 | 40,0 |
| 2 | 10,0 | 1,0 | 0,0 | 100,0 | 26,0 | 420,5 | 1,0 | 60,0 | 40,0 |
| 3 | 40,0 | 1,0 | 100,0 | 0,0 | 27,0 | 430,0 | 1,0 | 100,0 | 0,0 |
| 4 | 70,0 | 1,0 | 100,0 | 0,0 | 28,0 | 460,0 | 1,0 | 100,0 | 0,0 |
| 5 | 70,5 | 1,0 | 10,0 | 90,0 | 29,0 | 490,0 | 1,0 | 70.0 | 30,0 |
| 6 | 80,0 | 1,0 | 10,0 | 90,0 | 30,0 | 500,0 | 1,0 | 70,0 | 30,0 |
| 7 | 110,0 | 1,0 | 100,0 | 0,0 | 31,0 | 530,0 | 1,0 | 100,0 | 0,0 |
| 8 | 140,0 | 1,0 | 100,0 | 0,0 | 32,0 | 560,0 | 1,0 | 100,0 | 0,0 |
| 9 | 140,5 | 1,0 | 20,0 | 80,0 | 33,0 | 560,5 | 1,0 | 80,0 | 20,0 |
| 10 | 150,0 | 1,0 | 20,0 | 80,0 | 34,0 | 570,0 | 1,0 | 80,0 | 20,0 |
| 11 | 180,0 | 1,0 | 100,0 | 0,0 | 35,0 | 600,0 | 1,0 | 100,0 | 0,0 |
| 12 | 210,0 | 1,0 | 100,0 | 0,0 | 36,0 | 630,0 | 1,0 | 100,0 | 0,0 |
| 13 | 210,5 | 1,0 | 30,0 | 70,0 | 37,0 | 630,5 | 1,0 | 85,0 | 15,0 |
| 14 | 220,0 | 1,0 | 30,0 | 70,0 | 38,0 | 640,0 | 1,0 | 85,0 | 15,0 |
| 15 | 250,0 | 1,0 | 100,0 | 0,0 | 39,0 | 670,0 | 1,0 | 100,0 | 0,0 |
| 16 | 280,0 | 1,0 | 100,0 | 0,0 | 40,0 | 700,0 | 1,0 | 100,0 | 0,0 |
| 17 | 280,5 | 1,0 | 40,0 | 60,0 | 41,0 | 700,5 | 1,0 | 88,0 | 12,0 |
| 18 | 290,0 | 1,0 | 40,0 | 60,0 | 42,0 | 710,0 | 1,0 | 88,0 | 12,0 |
| 19 | 320,0 | 1,0 | 100,0 | 0,0 | 43,0 | 740,0 | 1,0 | 100,0 | 0,0 |
| 20 | 350,0 | 1,0 | 100,0 | 0,0 | 44,0 | 770,0 | 1,0 | 100,0 | 0,0 |
| 21 | 350,5 | 1,0 | 50,0 | 50,0 | 45,0 | 770,5 | 1,0 | 90,0 | 10,0 |

TABLE 3-continued

| Step | Time | Flow | % A | % B | Step | Time | Flow | %A | % B |
|---|---|---|---|---|---|---|---|---|---|
| 22 | 360,0 | 1,0 | 50,0 | 50,0 | 46,0 | 780,0 | 1,0 | 90,0 | 10,0 |
| 23 | 390,0 | 1,0 | 100,0 | 0,0 | 47,0 | 810,0 | 1,0 | 100,0 | 0,0 |
| 24 | 420,0 | 1,0 | 100,0 | 0,0 | 48,0 | 850,0 | 1,0 | 100,0 | 0,0 |

TABLE 4

| Step | Time | Flow | % A | % B | Step | Time | Flow | %A | % B |
|---|---|---|---|---|---|---|---|---|---|
| 1 | 0 | 2 | 100 | 0 | 49 | 720 | 2 | 100 | 0 |
| 2 | 45 | 2 | 100 | 0 | 50 | 765 | 2 | 100 | 0 |
| 3 | 46 | 2 | 0 | 100 | 51 | 766 | 2 | 74 | 26 |
| 4 | 52 | 2 | 0 | 100 | 52 | 772 | 2 | 74 | 26 |
| 5 | 60 | 2 | 100 | 0 | 53 | 780 | 2 | 100 | 0 |
| 6 | 105 | 2 | 100 | 0 | 54 | 825 | 2 | 100 | 0 |
| 7 | 106 | 2 | 8 | 92 | 55 | 826 | 2 | 76 | 24 |
| 8 | 113 | 2 | 8 | 92 | 56 | 832 | 2 | 76 | 24 |
| 9 | 120 | 2 | 100 | 0 | 57 | 840 | 2 | 100 | 0 |
| 10 | 165 | 2 | 100 | 0 | 58 | 885 | 2 | 100 | 0 |
| 11 | 166 | 2 | 20 | 80 | 59 | 886 | 2 | 78 | 22 |
| 12 | 172 | 2 | 20 | 80 | 60 | 892 | 2 | 78 | 22 |
| 13 | 180 | 2 | 100 | 0 | 61 | 900 | 2 | 100 | 0 |
| 14 | 225 | 2 | 100 | 0 | 62 | 945 | 2 | 100 | 0 |
| 15 | 226 | 2 | 28 | 72 | 63 | 946 | 2 | 80 | 20 |
| 16 | 232 | 2 | 28 | 72 | 64 | 952 | 2 | 80 | 20 |
| 17 | 240 | 2 | 100 | 0 | 65 | 960 | 2 | 100 | 0 |
| 18 | 285 | 2 | 100 | 0 | 66 | 1005 | 2 | 100 | 0 |
| 19 | 286 | 2 | 34 | 66 | 67 | 1006 | 2 | 82 | 18 |
| 20 | 292 | 2 | 34 | 66 | 68 | 1012 | 2 | 82 | 18 |
| 21 | 300 | 2 | 100 | 0 | 69 | 1020 | 2 | 100 | 0 |
| 22 | 345 | 2 | 100 | 0 | 70 | 1065 | 2 | 100 | 0 |
| 23 | 348 | 2 | 42 | 58 | 71 | 1066 | 2 | 84 | 16 |
| 24 | 352 | 2 | 42 | 58 | 72 | 1072 | 2 | 84 | 16 |
| 25 | 360 | 2 | 100 | 0 | 73 | 1080 | 2 | 100 | 0 |
| 26 | 405 | 2 | 100 | 0 | 74 | 1125 | 2 | 100 | 0 |
| 27 | 406 | 2 | 50 | 50 | 75 | 1126 | 2 | 86 | 14 |
| 28 | 412 | 2 | 50 | 50 | 76 | 1132 | 2 | 86 | 14 |
| 29 | 420 | 2 | 100 | 0 | 77 | 1140 | 2 | 100 | 0 |
| 30 | 465 | 2 | 100 | 0 | 78 | 1185 | 2 | 100 | 0 |
| 31 | 466 | 2 | 54 | 46 | 79 | 1186 | 2 | 88 | 12 |
| 32 | 472 | 2 | 54 | 46 | 80 | 1192 | 2 | 88 | 12 |
| 33 | 480 | 2 | 100 | 0 | 81 | 1200 | 2 | 100 | 0 |
| 34 | 525 | 2 | 100 | 0 | 82 | 1245 | 2 | 100 | 0 |
| 35 | 526 | 2 | 58 | 42 | 83 | 1246 | 2 | 90 | 10 |
| 36 | 532 | 2 | 58 | 42 | 84 | 1252 | 2 | 90 | 10 |
| 37 | 540 | 2 | 100 | 0 | 85 | 1260 | 2 | 100 | 0 |
| 38 | 585 | 2 | 100 | 0 | 86 | 1305 | 2 | 100 | 0 |
| 39 | 586 | 2 | 62 | 38 | 87 | 1306 | 2 | 95 | 5 |
| 40 | 592 | 2 | 62 | 38 | 88 | 1312 | 2 | 95 | 5 |
| 41 | 600 | 2 | 100 | 0 | 89 | 1319 | 2 | 100 | 0 |
| 42 | 645 | 2 | 100 | 0 | 90 | 1364 | 2 | 100 | 0 |
| 43 | 646 | 2 | 66 | 34 | 91 | 1365 | 2 | 85 | 15 |
| 44 | 652 | 2 | 66 | 34 | 92 | 1371 | 2 | 85 | 15 |
| 45 | 660 | 2 | 100 | 0 | 93 | 1378 | 2 | 100 | 0 |
| 46 | 705 | 2 | 100 | 0 | 94 | 1425 | 2 | 100 | 0 |
| 47 | 706 | 2 | 70 | 30 | | | | | |
| 48 | 713 | 2 | 70 | 30 | | | | | |

TABLE 5

| Step | Time | Flow | % A | % B | Step | Time | Flow | %A | % B |
|---|---|---|---|---|---|---|---|---|---|
| 1 | 0 | 2 | 100 | 0 | 49 | 720 | 2 | 100 | 0 |
| 2 | 45 | 2 | 100 | 0 | 50 | 765 | 2 | 100 | 0 |
| 3 | 46 | 2 | 0 | 100 | 51 | 766 | 2 | 74 | 26 |
| 4 | 52 | 2 | 0 | 100 | 52 | 772 | 2 | 74 | 26 |
| 5 | 60 | 2 | 100 | 0 | 53 | 780 | 2 | 100 | 0 |
| 6 | 105 | 2 | 100 | 0 | 54 | 825 | 2 | 100 | 0 |
| 7 | 106 | 2 | 8 | 92 | 55 | 826 | 2 | 76 | 24 |
| 8 | 113 | 2 | 8 | 92 | 56 | 832 | 2 | 76 | 24 |
| 9 | 120 | 2 | 100 | 0 | 57 | 840 | 2 | 100 | 0 |
| 10 | 165 | 2 | 100 | 0 | 58 | 885 | 2 | 100 | 0 |
| 11 | 166 | 2 | 20 | 80 | 59 | 886 | 2 | 78 | 22 |
| 12 | 172 | 2 | 20 | 80 | 60 | 892 | 2 | 78 | 22 |
| 13 | 180 | 2 | 100 | 0 | 61 | 900 | 2 | 100 | 0 |
| 14 | 225 | 2 | 100 | 0 | 62 | 945 | 2 | 100 | 0 |
| 15 | 226 | 2 | 28 | 72 | 63 | 946 | 2 | 80 | 20 |
| 16 | 232 | 2 | 28 | 72 | 64 | 952 | 2 | 80 | 20 |
| 17 | 240 | 2 | 100 | 0 | 65 | 960 | 2 | 100 | 0 |
| 18 | 285 | 2 | 100 | 0 | 66 | 1005 | 2 | 100 | 0 |
| 19 | 286 | 2 | 34 | 66 | 67 | 1006 | 2 | 82 | 18 |
| 20 | 292 | 2 | 34 | 66 | 68 | 1012 | 2 | 82 | 18 |
| 21 | 300 | 2 | 100 | 0 | 69 | 1020 | 2 | 100 | 0 |
| 22 | 345 | 2 | 100 | 0 | 70 | 1065 | 2 | 100 | 0 |
| 23 | 348 | 2 | 42 | 58 | 71 | 1066 | 2 | 84 | 16 |
| 24 | 352 | 2 | 42 | 58 | 72 | 1072 | 2 | 84 | 16 |
| 25 | 360 | 2 | 100 | 0 | 73 | 1080 | 2 | 100 | 0 |
| 26 | 405 | 2 | 100 | 0 | 74 | 1125 | 2 | 100 | 0 |
| 27 | 406 | 2 | 50 | 50 | 75 | 1126 | 2 | 86 | 14 |
| 28 | 412 | 2 | 50 | 50 | 76 | 1132 | 2 | 86 | 14 |
| 29 | 420 | 2 | 100 | 0 | 77 | 1140 | 2 | 100 | 0 |
| 30 | 465 | 2 | 100 | 0 | 78 | 1185 | 2 | 100 | 0 |
| 31 | 466 | 2 | 54 | 46 | 79 | 1186 | 2 | 88 | 12 |
| 32 | 472 | 2 | 54 | 46 | 80 | 1192 | 2 | 88 | 12 |
| 33 | 480 | 2 | 100 | 0 | 81 | 1200 | 2 | 100 | 0 |
| 34 | 525 | 2 | 100 | 0 | 82 | 1245 | 2 | 100 | 0 |
| 35 | 526 | 2 | 58 | 42 | 83 | 1246 | 2 | 90 | 10 |
| 36 | 532 | 2 | 58 | 42 | 84 | 1252 | 2 | 90 | 10 |
| 37 | 540 | 2 | 100 | 0 | 85 | 1260 | 2 | 100 | 0 |
| 38 | 585 | 2 | 100 | 0 | 86 | 1305 | 2 | 100 | 0 |
| 39 | 586 | 2 | 62 | 38 | 87 | 1306 | 2 | 95 | 5 |
| 40 | 592 | 2 | 62 | 38 | 88 | 1312 | 2 | 95 | 5 |
| 41 | 600 | 2 | 100 | 0 | 89 | 1319 | 2 | 100 | 0 |
| 42 | 645 | 2 | 100 | 0 | 90 | 1364 | 2 | 100 | 0 |
| 43 | 646 | 2 | 66 | 34 | 91 | 1365 | 2 | 85 | 15 |
| 44 | 652 | 2 | 66 | 34 | 92 | 1371 | 2 | 85 | 15 |
| 45 | 660 | 2 | 100 | 0 | 93 | 1378 | 2 | 100 | 0 |
| 46 | 705 | 2 | 100 | 0 | 94 | 1425 | 2 | 100 | 0 |
| 47 | 706 | 2 | 70 | 30 | | | | | |
| 48 | 713 | 2 | 70 | 30 | | | | | |

EXAMPLE 1

Production and Folding of Human and Murine $\beta_2$-microglobulin

This example describes the production in *E. coli* of both human $\beta_2$-microglobulin and murine $\beta_2$-microglobulin as $FX_a$ cleavable fusion proteins, and the purification of the recombinant human and murine $\beta_2$-microglobulin after $FX_a$ cleavage.

Plasmid clones containing the full length cDNAs encoding the human and the murine $\beta_2$-microglobulin proteins (generously provided by Dr. David N. Garboczi to Dr. Soren Buus) were used as templates in a Polymerase Chain Reaction (PCR) (Saiki et al., 1988) designed to produce cDNA fragments corresponding to the mature human (corresponding to amino acid residue $Ile_1$ $Met_{99}$) and the mature murine (corresponding to amino acid residue $Ile_1$ $Met_{99}$) $\beta_2$-microglobulin proteins, by use of the primers SEQ ID NO: 3 and SEQ ID NO: 4 (for the human $\beta_2$-microglobulin) and SEQ ID NO: 5 and SEQ ID NO: 6 (for the murine $\beta_2$-microglobulin). The amplified coding reading frames were at their 5=-ends, via the PCR-reaction, linked to nucleotide sequences, included in SEQ ID NO: 3 and 5, encoding the amino acid sequence SEQ ID NO: 37, which constitute a cleavage site for the bovine restriction protease $FX_a$ (Nagai and Thogersen, 1987). The amplified DNA fragments were subcloned into the *E. coli* expression vector $pT_7H_6$ (Christensen et al., 1991). The construction of the resulting plasmids $pT_7H_6FX$-h$\beta_2$m (expressing human $\beta_2$-microglobulin) and $pT_7H_6FX$-h$\beta_2$m (expressing murine $\beta_2$-microglobulin) is outlined in FIG. 2 and in FIG. 3 is shown the amino acid sequences of the expressed proteins (SEQ ID NO: 49 (human) and SEQ ID NO: 50 (murine)).

Human and murine $\beta_2$ microglobulin were produced by growing and expressing the plasmids pT$_7$H$_6$FX-h$\beta_2$m and -m$\beta_2$m in *E. coli* BL21 cells in a medium scale (2×1 liter) as described by Studler and Moffat, J. Mol. Biol., 189: 113–130, 1986. Exponentially growing cultures at 37° C. were at OD$_{600}$ 0.8 infected with bacteriophage λCE6 at a multiplicity of approximately 5. Cultures were grown at 37° C. for another three hours before cells were harvested by centrifugation. Cells were lysed by osmotic shock and sonification and total cellular protein extracted into phenol (adjusted to pH 8 with Trisma base). Protein was precipitated from the phenol phase by addition of 2.5 volumes of ethanol and centrifugation. The protein pellet was dissolved in a buffer containing 6M guanidinium chloride, 50 mM Tris-HCl pH 8 and 0.1M dithioerythriol. Following gel filtration on Sephadex G-25 (Pharmacia, LKB, Sweden) into 8M Urea, 1M NaCl, 50 mM Tris-HCl ph8, 10 mM 2-mercaptoethanol and 3 mM methionine the crude protein preparation was applied to Ni$^{2+}$activated NTA-agarose columns for purification (Hochuli et al., 1988.) of the fusion proteins, MGSHHHHHHGSIEGR-human and murine $\beta_2$-microglobulin (wherein MGSHHHHHHGSIEGR is SEQ ID NO: 48) respectively and subsequently to undergo the cyclic folding procedure.

All buffers prepared for liquid chromatograpy were degassed under vacuum prior to addition of reductant and/or use.

Ni$^{2+}$ activated NTA-agarose matrix (Ni$^{2+}$NTA-agarose) is commercially available from Diagen GmbH, Germany. During the course of this work it was found, however, that this commercial product did not perform as well as expected. Our observations were, that the commercial Ni$^{2+}$NTS-agarose matrix was easily blocked when applying the denatured and reduced total protein extract, that the capacity for fusion protein was lower than expected, and that the matrix could only be regenerated successfully a few times over.

In order to improve the performance of the Ni$^{2+}$NTA-agarose it was decided to perform a carbodiimide coupling of the N-(5-amino-1-carboxypentyl)iminodiacetic acid metal ligand (synthesis route as described by Döbeli & Hochuli (EPO 0253 303)) to a more rigid agarose matrix (i.e. Sepharose CL-6B, Pharmacia, Sweden):

8 g. of N-(5-amino-1-carboxypentyl)iminodiacetic acid from the synthesis procedure in 50 ml was adjusted to pH 10 by addition of 29 g. of Na$_2$CO$_3$(10 H$_2$O) and added to a stirred suspension of activated Sepharose CL-6B in 1M Na$_2$CO$_3$. Reaction was allowed overnight.

The Sepharose CL-6B (initially 100 ml. suspension) was activated after removal of water by acetone with 7 g. of 1,1'-carbonyldiimidazol under stirring for 15 to 30 min. Upon activation the Sepharose CL-6B was washed with acetone followed by water and 1M Na$_2$CO$_3$. The NTA-agarose matrix was loaded into a column and "charged" with Ni$^{2+}$ by slowly passing through 5 column volumes of a 10% NiSO$_4$ solution. The amount of Ni$^{2+}$ on the NTA-agarose matrix, prepared by this procedure, has been determined to 14 μmoles per ml matrix. The Ni$^{2+}$NTA-agarose matrix was packed in a standard class column for liquid chromatograpy (internal diameter: 2.6 cm) to a volume of 40 ml. After charging the Ni$^{2+}$NTA-agarose column was washed with two column volumes of water, one column volume of 1M Tris-HCl pH 8 and two column volumes of loading buffer before application of the crude protein extract.

Upon application of the crude protein extracts on the Ni$^{2+}$NTA-agarose column, the fusion proteins, MGSHHHHHHGSIEGR-h$\beta_2$m and MGSHHHHHHGSIEGR-m$\beta_2$m (wherein MGSHHHHH-HGSIEGR is SEQ ID NO: 48) respectively, were purified from the majority of coil and λ phage proteins by washing with one column volume of the loading buffer followed by 6M guanidinium chloride, 50 mM Tris-HCl, 10 mM 2-mercaptoethanol, and 3 mM methionine until the optical density (OD) at 280 nm of the column eluates were stable.

The fusion proteins were refolded on the Ni$^{2+}$NTA-agarose column using a gradient manager profile as described in table 1 and 0.5M NaCl. 50 mN Tris-HCl pH 8, and 1.2 mM/0.4 mM reduced/oxidized glutathione as buffer A and 8M urea, 0.5M NaCl, 50 mM Tris-HCl pH 8, 3 mM methionine, and 6 mM reduced glutathione as buffer B. The reduced/oxidized glutathione solution was freshly prepared as a 200 times stock solution by addition of 9.9M H$_2$O$_2$ to a stirred solution of 0.2M reduced glutathione before addition to buffer A.

After completion of the cyclic folding procedure the h$\beta_2$m and m$\beta_2$m fusion proteins were eluted from the Ni$^{2+}$NTA-agarose columns with a buffer containing 0.5M NaCl, 50 mM Tris-HCl, 20 mM EDTA pH 8.

Fusion protein that were aggregated and precipitated on the Ni$^{2+}$NTA-agarose columns were eluted in buffer B. Approximately 75% of the fusion protein material was eluted by non-denaturing elution buffer (see FIG. 16, lanes 2 and 3).

As judged by non-reducing SDS PAGE analysis approximately 70% of the soluble h$\beta_2$m fusion protein material (corresponding to 40 mg of h$\beta_2$m fusion protein) appeared monomeric (see FIG. 15, lanes 5 and 3) whereas 25% of the m$\beta_2$m fusion protein appeared monomeric (corresponding to 20 mg of m$\beta_2$m fusion protein). The overall efficiency of the folding procedure are therefore approximately 50% for the h$\beta_2$m fusion protein and less than 20% for the m$\beta_2$m fusion protein.

Monomeric h$\beta_2$m and m$\beta_2$m fusion proteins were purified from dimer and higher order multimers by ion exchange chromatography on S-Sepharose (Pharmacia, Sweden): The fusion proteins eluted by the non denaturing elution buffer (approximately 70% of the fusion protein material) was gelfiltrated into a buffer containing 5 mM NaCl and 5 mM Tris-HCl pH 8 on Sephadex G-25 and diluted 1:1 with water before applied onto the S-Sepharose ion exchange columns. Fusion proteins were eluted over 5 column volumes with a liner gradient from 2.5 mM NaCl, 2.5 mM Tris-HCl pH 8 to 100 mM NaCl, 25 mM Tris-HCl pH 8. The monomeric h$\beta_2$m as well as m$\beta_2$m fusion proteins eluted in the very beginning of the gradient, whereas dimers and higher order multimers eluted later. Fractions containing the monomeric fusion proteins were diluted with water and reloaded onto the S-Sepharose columns and one-step eluted in 1M NaCl, 50 mM Tris-HCl pH 8.

The monomeric fusion proteins were cleaved with the restriction protease FX$_a$ overnight at room temperature in a weight to weight ration of approximately 200 to one.

After cleavage the recombinant b$\beta_2$m and m$\beta_2$m proteins were purified from the N terminal fusion tail, liberated from the cleaved fusion protein and FX$_a$ by ion exchange chromatography on Q-Sepharose columns (Pharmacia, Sweden): Upon gelfiltration on Sephadex G-25 into 5 mM NaCl, 5 mM Tris-HCl pH 8 and 1:1 dilution with water, recombinant h$\beta_2$m and m$\beta_2$m were eluted in a linear gradient (over 5 column volumes) from 2.5 mM NaCl, 2.5 mM Tris-HCl pH 8 to 100 mM NaCl, 25 mM Tris-HCl pH 8. Fractions containing the cleaved recombinant proteins were diluted with water and reloaded to the Q-Sepharose columns and one-step eluted in 1M NaCl, 50 mM Tris-HCl pH 8. Recombinant h$\beta_2$m and m$\beta_2$m proteins were gelfiltrated into freshly prepared 20 mM NH$_4$HCO$_3$ and lyophilized twice.

SDS-PAGE analysis of the production of recombinant human $\beta_2$-microglobulin is presented in FIG. 15.

The yield of fully processed recombinant human $\beta_2$-microglobulin produced by this procedure was 30 mg.

The yield of fully processed recombinant murine $\beta_2$-microglobulin produced by this procedure was 10 mg.

Comparison of recombinant human with purified natural human $\beta_2$-microglobulin $\beta_2$-microglobulin was kindly carried out by Dr. Soren Buus in two different assays:

1. It was found that Recombinant human $\beta_2$-microglobulin and natural human $\beta_2$-microglobulin reacted with both a monoclonal- and a monospecific antibody with identical affinity.
2. Recombinant human $\beta_2$-microglobulin and natural human $\beta_2$-microglobulin were in an binding inhibition experiment using radiolabelled ligands found to bind natural affinity purified heavy chain class I K$^d$ molecules with an identical affinity.

Recombinant murine $\beta_2$-microglobulin was found to bind natural class I heavy chain molecules with an affinity 5 times lower than the $\beta_2$-microglobulin. This result is in good agreement with previous results from the literature using natural material.

EXAMPLE 2

Production and folding of Human Growth Hormone (Somatotropin)

This example describes the production in *E. coli* of human growth hormone (hGH) as a FX$_a$ cleavable fusion protein, and the purification of the recombinant hGH after FX$_a$ cleavage.

A plasmid clone containing the cDNA encoding the hGH (generously provided by Dr. Henrik Dalboge (Dalboge et al., 1987) were used as template in a Polymerase Chain Reaction (PCR) (Saiki et al., 1988), using the primers SEQ ID NO: 7 and SEQ ID NO: 8, designed to produce a cDNA fragment corresponding to the mature hGH (corresponding to amino acid residue Phe$_1$ to Phe$_{191}$) protein. The amplified coding reading frame was at the 5'-end, via the PCR-reaction, linked to a nucleotide sequence, included in SEQ ID NO: 7, encoding the amino acid sequence SEQ ID NO: 37 which constitute a cleavage site for the bovine restriction protease FX$_a$ (Nagai and Thogersen, 1987). The amplified DNA fragment was subcloned into the *E. coli* expression vector pT$_7$H$_6$ (Christensen et al., 1991). The construction of the resulting plasmid pT$_7$H$_6$FX-hGH (expressing human Growth Hormone) is outlined in FIG. 4 and in FIG. 5 is shown the amino acid sequence of the expressed protein (SEQ ID NO: 51).

Recombinant human Growth Hormone was produced by growing and expressing the plasmid pT$_7$H$_6$FX-hGH in *E. coli* BL21 cells in a medium scale (2×1 liter) as described by Studier and Moffat, J. Mol. Biol., 189: 113–130, 1986. Exponentially growing cultures at 37° C. were at OD$_{600}$ 0.8 infected with bacteriophage λCE6 at a multiplicity of approximately 5. Cultures were grown at 37° C. for another three hours before cells were harvested by centrifugation. Cells were lysed by osmotic shock and sonification and total cellular protein extracted into phenol (adjusted to pH 8 with Trisma base). Protein was precipitated from the phenol phase by addition of 22.5 volumes of ethanol and centrifugation. The protein pellet was dissolved in a buffer containing 6M guanidinium chloride, 50 mM Tris-HCl pH 8 and 50 mM dithioerythriol. Following gel filtration on Sephadex G-25 (Pharmacia, LKB, Sweden) into 8M Urea, 1M NaCl, 50 mM Tris HCl pH 8, 5 mM 2-mercaptoethanol and 1 mM methionine the crude protein preparation was applied to a Ni$^{2+}$ activated NTA-agarose column (Ni$^{2+}$NTA-agarose) for purification (Hochuli et al., 1988) of the fusion protein, MGSHHHHHHGSIEGR-hGH (wherein MGSHHHHHHG-SIEGR is SEQ ID NO: 48) and subsequently to undergo the cyclic folding procedure.

Preparation and "charging" of the Ni$^{2+}$NTA-agarose column is described under Example 1.

All buffers prepared for liquid chromatography were degassed under vacuum prior to addition of reductant and/or use.

Upon application of the crude protein extract on the Ni$^{2+}$NTA-agarose column, the fusion protein, MGSHHHHHHGSIEGR-hGH (wherein MGSHHHHHHG-SIEGR is SEQ ID NO: 48) was purified from the majority of *E. coli* and λ phage proteins by washing with one column volume of the loading buffer followed by 6M guanidinium chloride, 50 mM Tris-HCl, 5 mM 2 mercaptoethanol, and 1 mM methionine until the optical density (OD) at 280 nm of the eluate was stable.

The fusion protein was refolded on the Ni$^{2+}$NTA-agarose columns using a gradient manager profile as described in table 2 and 0.5M NaCl 50 mM Tris-HCl pH 8, and 1.0 mM/0.1 mM reduced/oxidized glutathione as buffer A and 8M urea, 0.5M NaCl, 50 mM Tris-HCl pH 8, 1 mM methionine, and 5 mM reduced glutathione as buffer B. The reduced/oxidized glutathione solution was freshly prepared as a 200 times stock solution by addition of 9.9M H$_2$)$_2$ to a stirred solution of 0.2M reduced glutathione before addition to buffer A.

After completion of the cyclic folding procedure the hGH fusion protein was eluted form the Ni$^{2+}$NTA-agarose column with a buffer containing 0.5M NaCl, 50 mM Tris-HCl, 20 mM EDTA pH 8. Fusion protein that was aggregated and precipitated on the Ni$^{2+}$NTA-agarose column was eluted in buffer B.

Approximately 80% of the fusion protein material was eluted by the non-denaturing elution buffer (see FIG. 16, lanes 2 and 3). As judged by non-reducing SDS PAGE analysis 90% of the soluble fusion protein material (corresponding to approximately 70 mg of fusion protein) appeared monomeric (see FIG. 16, land 2) yielding an overall efficiency of the folding procedure of approximately 70%.

Monomeric hGH fusion protein was purified from dimer and higher order multimers by ion exchange chromatography on Q-Sepharose (Pharmacia, Sweden): After gelfiltration into a buffer containing 25 mM NaCl and 25 mM Tris-HCl pH 8 on Sephadex G-25 the fusion protein material, eluted by the non-denaturing buffer, was applied onto a Q-Sepharose ion exchange column. Fusion protein was eluted over 5 column volumes with a linear gradient from 25 mM NaCl, 25 mM Tris-HCl pH 8 to 200 mM NaCl, 50 mM Tris-HCl pH 8. The monomeric hGH fusion protein eluted in the beginning of the gradient, whereas dimers and higher order multimers eluted later. Fractions containing the pure monomeric fusion protein was added NiSO$_4$ and iminodiacetic acid (IDA, adjusted pH 8 with NaOH) to 1 mM and cleaved with the restriction protease $FX_a$ for 5 hours at 37° C. in a weight to weight ration of approximately 100 to one. $FX_a$ was inhibited after cleavage by addition of Benzamidine hydrochloride to 1 mM.

After cleavage the recombinant hGH protein was isolated from uncleaved fusion protein and the liberated fusion tail, upon gelfiltration on Sephadex G-25 into 8M Urea, 50 mM Tris-HCl pH 8, to remove $Ni^{2+}$IDA and Benzamidine, by passage through a small $Ni^{2+}$NTA-agarose column followed inline by a small $Nd^3$NTA agarose column and subsequently a non $Ni^{2+}$activated NTA-agarose column to ensure complete removal of $FX_a$ and of $Ni^{2+}$ and $Nd^{3+}$, respectively. Recombinant hGH was purified from a minor fraction of recombinant breakdown product by ion exchange chromatography on Q-Sepharose: hGH was eluted in a linear gradient (over 5 column volumes) from 8M Urea, 50 mM Tris HCl pH 8 to 8M Urea, 250 mM NaCl, 25 mM Tris-HCl pH 8. Fractions containing the cleaved purified recombinant protein was gelfiltrated into freshly prepared 20 mM $NH_4HCO_3$ and lyophilized twice.

SDS-PAGE analysis of the production and folding of recombinant human growth hormone is presented in FIG. 16.

The yield of fully processed recombinant human growth hormone produced by this procedure was 10 mg.

The recombinant human growth hormone produced by this procedure co-migrated both in reducing and non-reducing SDS-PAGE and in non-denaturing PAGE analysis with biologically active recombinant human growth hormone generously provided by Novo-Nordisk A/S.

EXAMPLE 3

Production and folding of human $\alpha_2$MRAP

The plasmid used for expression in *E. coli* BL21 cells of the human $\alpha_2$-Macroglobulin Receptor Associated Protein ($\alpha_2$-MRAP), pT7H6FX-$\alpha_2$MRAP and the conditions used for production of the fusion protein has previously been described by us in Nykjar et al., J. Biol. Chem. 267: 14543–14546, 1992. The primers SEQ ID NO: 9 and SEQ ID NO: 10 were used in the PCR employed for multiplying the $\alpha_2$MRAP encoding DNA.

Crude protein extract precipitated from the phenol phase of the protein extraction of cells from 2 liters of culture of MGSHHHHHHGSIEGR-$\alpha_2$MRAP (wherein MGSHHHH-HHGSIEGR is SEQ ID NO: 48) expressing *E. coli* BL21 cells was dissolved in a buffer containing 6M guanidinium chloride, 50 mM Tris-HCl pH 8 and 50 mM dithioerythriol. Following gel filtration on Sephadex G-25 (Pharmacia, Sweden) into 8M Urea, 0.5M NaCl, 50 mM Tris-HCl pH 8, and 1mM methionine the crude protein preparation was applied to a $Ni^{2+}$activated NTA-agarose matrix ($Ni^{2+}$NTA-agarose) for purification (Hochuli et al., 1988) of the fusion protein, MGSHHHHHHGSIEGR-$\alpha_2$MRAP (wherein MGSHHHHHHGSIEGR is SEQ ID NO: 48) and subsequently to undergo the cyclic folding process.

All buffers prepared for liquid chromatography were degassed under vacuum prior to addition of reductant and/or use.

Preparation and "charging" of the $Ni^{2+}$NTA-agarose column is described under Example 1.

Upon application of the crude protein extract on the $Ni^{2+}$NTA-agarose column, the fusion protein, MGSHHHH-HHGSIEGR $\alpha_2$MRAP (wherein MGSHHHHHHGSIEGR is SEQ ID NO: 48) was purified from the majority of *E. coli* and λ phage proteins by washing with one column volume of the loading buffer followed by 6M guanidinium chloride, 50 mM Tris-HCl, and 1 mM methionine until the optical density (OD) at 280 nm of the eluate was stable.

The fusion protein was refolded on the $Ni^{2+}$NTA-agarose column using a gradient manager profile as described in table 3 and 0.5M NaCl, 50 mM Tris-HCl pH 8, 2 mM $CaCl_3$ and 1 mM 2-mercaptoethanol as buffer A and 6M guanidinium chloride, 50 mM Tris-HCl pH 8, 2 mM $CaCl_2$ and 1 mM 2-mercaptoethanol as buffer B.

After completion of the cyclic folding procedure the $\alpha_2$MRAP fusion protein was eluted from the $Ni^{2+}$NTA agarose column with a buffer containing 0.5M NaCl, 50 mM Tris-HCl, 20 mM EDTA pH 8.

Virtually no fusion protein was found to be aggregated or precipitated on the $Ni^{2+}$NTA-agarose column. The estimated yield of $\alpha_2$MRAP fusion protein was 60 mg and the efficiency of the folding procedure was close to 95%.

The fusion protein MGSHHHHHHGSIEGR-$\alpha_2$MRAP (wherein MGSHHHHHHGSIEGR is SEQ ID NO: 48) was cleaved with the bovine restriction protease $FX_a$ overnight at room temperature in a weight to weight ration of 200:1 in the elution buffer. Upon gelfiltration on Sephadex G-25 into 100 mM NaCl, 25 mM Tris-HCl pH 8, the protein solution was passed through a $Ni^{2+}$NTA agarose column thereby removing uncleaved fusion protein and the liberated fusion N-terminal tail originating from cleaved fusion proteins. Finally the protein solution was diluted 1:4 with water and the $\alpha_2$MRAP protein purified from $FX_a$ by ion exchange chromatography on Q Sepharose (Pharmacia, Sweden). The Q-Sepharose column was eluted with a linear gradient over 6 column volumes from 25 mM NaCl, 25 mM Tris-HCl pH 8 to 250 mM NaCl, 25 MM Tris-HCl pH 8. The $\alpha_2$MRAP protein eluted in the very beginning of the linear gradient whereas $FX_a$ eluted later.

The yield of $\alpha_2$MRAP protein produced and refolded by this procedure was 40 mg.

The ligand binding characteristics (i.e. binding to the $\alpha_2$-Macroglobulin Receptor and interference with the binding of human Urokinase Plasminogen Activator—Plasminogen Activator inhibitor type-T complex to the $\alpha_2$-M Receptor) has, according to Dr. Nykjar, been found identical to the ligand binding characteristics of the purified natural protein.

EXAMPLE 4

Production and folding of domains and domain-clusters from the $\alpha_2$-M Receptor The human $\alpha_2$-Macroglobulin Receptor/Low Density Lipoprotein Receptor-Related Protein ($\alpha_2$MR) is a 600 kDa endocytotic membrane receptor. $\alpha_2$-MR is synthesized as a 4524 amino acid single chain precursor protein. The precursor is processed into a 85 kDa transmembrane β-chain and a 500 kDa α-chain, non-covalently bound to the extracellular domain of the β-chain. The $\alpha_2$-MR is known to bind $Ca^{2+}$ in a structure dependent manner (i.e. the reduced protein does not bind $Ca^{2+}$) and is believed to be multifunctional in the sense that $\alpha_2$-MR binds ligands of different classes.

The entire amino acid sequence of the α-chain can be represented by clusters of three types of repeats also found in other membrane bound receptors and in various plasma proteins:

A: this type of repeat spans approximately 40 amino acid residues and is characterised by the sequential appearance of the six cysteinyl residues contained in the repeat. Some authors have named this repeat complement-type domain.

B: This type of repeat also spans approximately 40 amino acid residues and is characterised by the sequential appearance of the six cysteinyl residues contained in the repeat. In the literature this repeat has been named EGF-type domains.

C: This type of repeat spans approximately 55 amino acid residues and is characterised by the presence of the consensus sequence SEQ ID NO: 39.

This example describes the production in *E. coli* of a number of domains and domain-clusters derived from the $\alpha_2$-MR protein as $FX_a$ cleavable fusion proteins and the purification, in vitro folding, and the $FX_a$ cleavage and processing of these recombinant proteins.

A plasmid clone containing the full length cDNA encoding the human $\alpha_2$-MR protein (generously provided by Dr. Joachim Herz; Herz et al., EMBO J., 7:4119–4127, 1988) was used as template in a series of Polymerase Chain Reactions (PCR) designed to produce cDNA fragments corresponding to a number of polypeptides representing domains and domain-clusters derived from the $\alpha_2$-MR protein:

1: Contains two domains of the A-type, corresponding to amino acid residues 20 to 109 in the $\alpha_2$-MR protein. The primers SEQ ID NO: 11 and SEQ ID NO: 12 were used in the PCR.

2: Contains two domains of the A-type followed by two type-B domains, corresponding to amino acid residues 20 to 190 in the $\alpha_2$-MR protein. The primers SEQ ID NO: 11 and SEQ ID NO: 13 were used in the PCR.

3: Identical to #2 followed by a region containing YWTD repeats, corresponding to amino acid residues 20 to 521. The primers SEQ ID NO: 11 and SEQ ID NO: 14 were used in the PCR.

4: Contains one type B domain, followed by 8 type-A domains and finally two type-B domains, corresponding to amino acid residues 803 to 1265 in the $\alpha_2$ MR protein. The primers SEQ ID NO: 15 and SEQ ID NO: 16 were used in the PCR.

5: Contains only the 8 type-A domains also present in #4, corresponding to amino acid residues 849 to 1184 in the $\alpha_2$-MR protein. The primers SEQ ID NO: 17 and SEQ ID NO: 18 were used in the PCR.

6: Contains the two C terminal type-B domains from #4, followed by 8 YWTD repeats and one type-B domain, corresponding to amino acid residues 1184 to 1502 in the $\alpha_2$-MR protein. The primers SEQ ID NO: 19 and SEQ ID NO: 20 were used in the PCR.

7: Contains the whole region included in constructs #4 to #6, corresponding to amino acid residues 803 t 1582 in the $\alpha_2$-MR protein. The primers SEQ ID NO: 15 and SEQ ID NO: 20 were used in the PCR.

8: Contains 10 type-A domains, corresponding to amino acid residues 2520 to 2941 in the $\alpha_2$-MR protein. The primers SEQ ID NO: 21 and SEQ ID NO: 22 were used in the PCR.

9: Contains 11 type-A domains, corresponding to amino acid residues 3331 to 3778 in the $\alpha_2$-MR protein. The primers SEQ ID NO: 23 and SEQ ID NO: 24 were used in the PCR.

The amplified nucleotide sequences encoding the domains and domain-clusters were at their 5'-end, via the PCR-reaction, linked to nucleotide sequences (included in SEQ ID NO: 11, 15, 17, 19, 21 and 23) encoding the amino acid sequence SEQ ID NO: 37 which constitutes a cleavage site for the bovine restriction protease $FX_a$ (Nagai and Thøgersen, Methods in Enzymology, 152:461–481, 1987). The amplified DNA fragments were either subcloned into the *E. coli* expression vector pT$_7$H$_6$ (Christensen et al., FEBS Letters, 281:181–184, 1991) or the expression plasmid pLcIIMLCH$_6$, which is modified from pLcIIMLC (Nagai et al., Nature, 332:284–286, 1988) by the insertion of an oligonucleotide encoding six histidinyl residues C-terminal of the myosin light chain fragment. The construction of the resulting plasmids pT$_7$H$_6$FX-#1 to #3 and pLcIIMLCH$_6$FX-#4 to #9 is outlined in FIGS. 6–8 and in FIG. 9 is shown the amino acid sequence of the expressed protein (SEQ ID NO: 52).

The domains and domain-clusters subcloned in the pT$_7$H$_6$FX series were grown and expressed in *E. coli* BL21 cells in a medium scale (2 liter) as described by Studier, and Moffat, J. Mol. Biol., 189:113–130, 1986. Exponentially growing cultures at 37 C. were at OD$_{600}$ 0.8 infected with bacteriophage λCE6 at a multiplicity of approximately 5. Cultures were grown at 37° C. for another three hours before cells were harvested by centrifugation. Cells were lysed by osmotic shock and sonification and total cellular protein extracted into phenol (adjusted to pH 8 with Trisma base).

The domain clusters subcloned in the pLcIIMLCH$_6$ series were grown and expressed in *E. coli* QY13 cells as described in Nagai and Thøgersen, Methods in Enzymology, 152:461–481, 1987. Exponentially growing cultures (4 liter) at 30° C. were at OD$_{600}$ 1.0 transferred to 42° C. for 15 min. This heat shock induces synthesis of the fusion proteins. The cultures were further incubated at 37° C. for three to four hours before cells were harvested by centrifugation. Cells were lysed by osmotic shock and sonification and total cellular protein extracted into phenol (adjusted to pH 8 with Trisma base).

Crude protein was precipitated from the phenol phase by addition of 2.5 volumes of ethanol and centrifugation. The protein pellet was dissolved in a buffer containing 6M guanidinium chloride, 50 mM Tris-HCl pH 8 and 0.1M dithioerythriol. Following gel filtration on Sephadex G-25 (Pharmacia, Sweden) into 8M Urea, 1M NaCl, 50 nM Tris HCl pH 8, 10 mM 2-mercaptoethanol and 2 mM methionine the crude protein preparations were applied to a Ni$^{2+}$ activated NTA-agarose columns for purification (Hochuli et al., 1988) of the fusion proteins and subsequently to undergo the cyclic folding procedure.

All buffers prepared for liquid chromatography were degassed under vacuum prior to addition or reductant and/or use.

Preparation and "charging" of the Ni$^{2+}$NTA-agarose column is described under Example 1.

Upon application of the crude protein extracts on the Ni$^{2+}$NTA-agarose column, the fusion proteins were purified from the majority of *E. coli* and λ phage proteins by washing with one column volume of the loading buffer followed by 6M guanidinium chloride, 50 mM Tris-HCl, 10 mM 2 mercaptoethanol, and 2 mM methionine until the optical density (OD) at 280 nm of the eluate was stable.

Each of the fusion proteins were refolded on the Ni$^{2+}$ NTA-agarose column using a gradient manager profile as described in table 4 and 0.5 M NaCl, 50 mM Tris-HCl pH 8, 2 mM CaCl$_2$, 0.33 mM methionine, and 2.0 mM/0.2 mM reduced/oxidized glutathione as buffer A and 4M urea, 0.5M NaCl, 50 mM Tris-HCl pH 8, 2 mM CaCl$_2$, 2 mM methionine, and 3 mM reduced glutathione as buffer B. The reduced/oxidized glutathione solution was freshly prepared as a 100 times stock solution by addition of 9.9M H$_2$O$_2$ to a stirred solution of 0.2M reduced glutathione before addition to buffer A.

After completion of the cyclic folding procedure the fusion proteins representing domains and domain-clusters derived from the $\alpha_2$-MR protein were eluted from the $Ni^{2+}$NTA-agarose column with a buffer containing 0.5M NaCl, 50 mM Tris-HCl, 5 mM EDTA pH 8. Fusion proteins that were aggregated and precipitated on the $Ni^{2+}$NTA-agarose column were eluted in buffer B.

Approximately 75% of the fusion protein material expressed from the plasmids $pT_7H_6FX$-#1 and #2, representing the N-terminal two and four cysteine-rich domains of the $\alpha_2$-MR protein were eluted from the $Ni^{2+}$NTA-agarose column by the non-denaturing buffer. The majority of this fusion protein material appeared as nonomers as judged by non-reducing SDS-PAGE analysis. The yields of monomeric fusion protein #1 and #2 were estimated to be approximately 50 mg.

Approximately 50% of the fusion protein material expressed from all other expression plasmids representing domain-clusters derived from the $\alpha_2$-MR protein was eluted from the $Ni^{2+}$NTA-agarose column by the non denaturing buffer. Between 30% (fusion proteins #5 and #7) and 65% (fusion protein #1) of these fusion proteins appeared as nonomers as judged by non-reducing SDS-PAGE analysis (see FIG. 17, lanes 9 and 10).

Each fusion protein eluted by the non-denaturing elution buffer was cleaved with the restriction protease $FX_a$ overnight at room temperature in an estimated weight to weight ratio of 100 to one.

Upon gelfiltration on Sephadex G-25 into 100 mM NaCl, 25 mM Tris-HCl pH 8, the protein solution was passed through a $Ni^{2+}$NTA-agarose column thereby removing uncleaved fusion protein and the liberated N-terminal fusion tail originating from the cleaved fusion proteins. $FX_a$ was removed from the solution by passing the recombinant protein solutions through a small column of SBTI-agarose (Soy Bean Trypsin Inhibitor immobilized on Sepharose CL-6B (Pharmacia, Sweden)).

Figure 17:
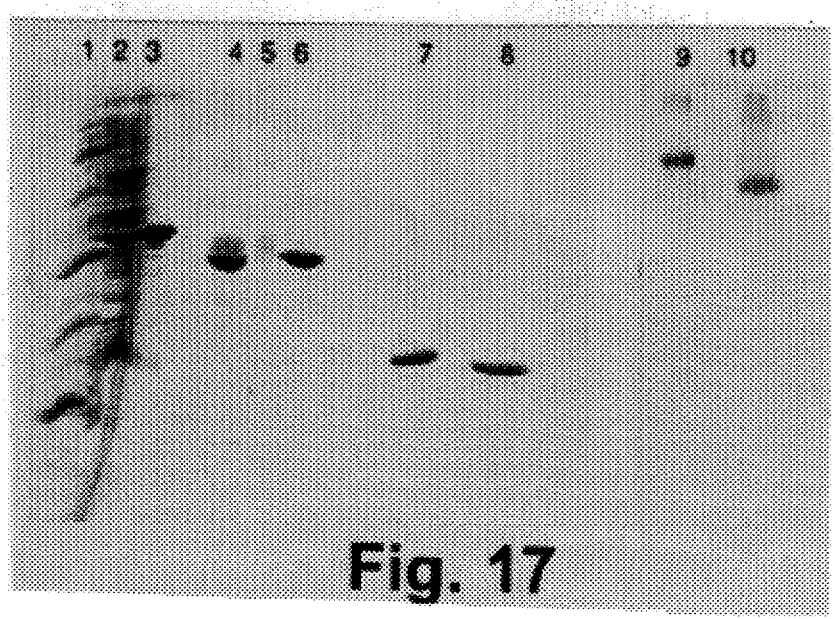

SDS-PAGE analysis of the refolded, soluble fusion protein product #4 is presented in FIG. 17, lanes 9 and 10, showing reduced and unreduced samples, respectively. The mobility increase observed for the unreduced sample reflects the compactness of the polypeptide due to the presence of 33 disulphide bridges.

Each of the recombinant proteins was found to bind $Ca^{2+}$ in a structure dependent manner.

It was found by Dr. Søron Moestrup that a monoclonal antibody, A2MRα-5 derived from the natural human $\alpha_2$-MR, bound the recombinant proteins expressed by the constructs #4, #6, and #7 whereas a monospecific antibody, A2MRα-3 derived also from natural $\alpha_2$-MR, was found to bind the recombinant protein expressed by construct #8. The binding specificity of both antibodies is structure dependent (i.e. the antibodies neither react with reduced $\alpha_2$-MR nor with reduced recombinant protein).

EXAMPLE 5

Production and folding of bovine coagulation Factor $X_a$ ($FX_a$)

This example describes the production in *E. coli* of one fragment derived from bovine $FX_a$ as a $FX_a$ cleavable fusion protein and the purification, in vitro folding, and the processing of the recombinant protein.

The cDNA encoding bovine FX was cloned by specific amplification in a Polymerase Chain Reaction (PCR) of the nucleotide sequences encoding bovine FX from amino acid residues $Ser_{82}$ to $Trp_{404}$ (SEQ ID NO: 2, residues 82–484) (FXΔγ, amino acid numbering relates to the full coding reading frame) using 1st strand oligo-dT primed cDNA synthesized from total bovine liver RNA as template. Primers used in the PCR were SEQ ID NO: 25 and SEQ ID NO: 26. RNA extraction and cDNA synthesis were performed using standard procedures.

The amplified reading frame encoding FXΔγ was at the 5'-end, via the PCR-reaction, linked to nucleotide sequences encoding the amino acid sequence SEQ ID NO: 37 which constitute a cleavage site for the bovine restriction protease $FX_a$ (Nagai, and Thøgersen. Methods in Enzymology, 152:461–481, 1987). The amplified DNA fragments was cloned into the *E. coli* expression vector pLcIIMLCH$_6$, which is modified from pLcIIMLC (Nagai et al., Nature, 332:284–286, 1988) by the insertion of an oligonucleotide encoding six histidinyl residues C-terminal of the myosin light chain fragment. The construction of the resulting plasmid pLcIIMLCH$_6$FX-FXΔγ is outlined in FIG. 10 and in FIG. 11 is shown the amino acid sequence of the expressed protein (SEQ ID NO: 53).

The pLcIIMLCH$_6$-FXΔγ plasmid was grown and expressed in *E. coli* QY13 cells as described in Nagai and Thøgersen (Methods in Enzymology, 152:461–481, 1987). Exponentially growing cultures at 30° C. were at $OD_{600}$ 1.0 incubated at 42° C. for 15 min. This heat shock induces synthesis of the fusion proteins. The cultures are further incubated at 37° C. for three to four hours before cells are harvested by centrifugation. Cells were lysed by osmotic shock and sonification and total cellular protein extracted into phenol (adjusted to pH 8 with Trisma base).

Crude protein was precipitated from the phenol phase by addition of 2.5 volumes of ethanol and centrifugation. The protein pellet was dissolved in a buffer containing 6M guanidinium chloride, 50 mM Tris-Hcl pH 8 and 0.1M dithioerythriol. Following gel filtration on Sephadex G-25 (Pharmacia, LKB, Sweden) into 8M Urea, 1M NaCl, 50 mM Tris-Hcl pH 8, 10 mM 2-mercaptoethanol the crude protein preparation was applied to a $Ni^{2+}$ activated NTA-agarose matrix for purification (Hochuli et al., 1988.) of the FXΔγ fusion protein and subsequently to undergo the cyclic folding procedure.

All buffers prepared for liquid chromatography were degassed under vacuum prior to addition of reductant and/or use.

Preparation and "charging" of the $Ni^{2+}$NTA-agarose column is described under Example 1.

Upon application of the crude protein extracts on the $Ni^{2+}$NTA-agarose column, the fusion proteins were purified from the majority of *E. coli* and λ phage proteins by washing with one column volume of the loading buffer followed by 6M guanidinium chloride, 50 mM Tris-HCl, and 10 mM 2-mercaptoethanol until the optical density (OD) at 280 nm of the eluate was stable.

The fusion protein was refolded on the $Ni^{2+}$NTA-agarose column using a gradient manager profile as described in table 5 and 0.5M NaCl, 50 mM Tris HCl pH 8, 2 mM $CaCl_2$, and 2.0 mM/0.2 mM reduced/oxidized glutathione as buffer A and 8M urea, 0.5M NaCl, 50 mN Tris-HCl pH 8, 2 mM $CaCl_2$, and 3 mM reduced glutathione as buffer B. The reduced/oxidized glutathione solution was freshly prepared as a 100 times stock solution by addition of 9.9M $H_2O_2$ to a stirred solution of 0.2M reduced glutothione before addition to buffer A.

After completion of the cyclic folding procedure the FXΔγ fusion protein was eluted from the $Ni^{2+}$NTA-agarose column with a buffer containing 0.5M NaCl, 50 mM Tris-HCl, 5 mM EDTA pH 8. Fusion protein that was aggregated and precipitated on the Ni$^{2+}$NTA-agarose column was eluted in buffer B.

Approximately 33% of the FXΔγ fusion protein material was eluted from the Ni$^{2+}$NTA-agarose column by the non-denaturing buffer. The amount of FXΔγ fusion protein was estimated to 15 mg. Only about one third of this fusion protein material appeared as nonomers as judged by non-reducing SDS-PAGE analysis corresponding to an overall efficiency of the folding procedure of approximately 10%.

FXΔγ fusion protein in non-denaturing buffer was activated by passing the recombinant protein solution through a small column of trypsin-agarose (trypsin immobilized on Sepharose CL-6B (Pharmacia, Sweden)).

The activated recombinant FXΔγ fusion protein was assayed for protocolytic activity and substrate specificity profile using standard procedures with chromogenic substrates. The activity and substrate specificity profile was indistinguishable from that obtained for natural bovine $FX_a$.

EXAMPLE 6

Production and folding of kringle domains 1 and 4 from human plasminogen

This example describes the production in *E. coli* of the lysine binding kringle domains 1 and 4 from human plasminogen (K1 and K4, respectively) as $KX_a$ cleavable fusion proteins and the purification and in vitro folding of the K1- and K4-fusion proteins.

A plasmid clone containing the full length cDNA encoding human plasminogen cloned into the general cloning vector pUC18 (generously provided by Dr. Earl Davie, Seattle, U.S.A.) was used as template in a Polymerase Chain Reaction (PCR) designed to produce cDNA fragments corresponding to K1 (corresponding to amino acid residues $Ser_{81}$ to $Glu_{162}$ in so-called Glu-plasminogen) and K4 (corresponding to amino acid residues $Val_{354}$ to $Ala_{439}$ in so-called Glu-plasminogen). The primers SEQ ID NO: 27 and SEQ ID NO: 28 were used in the PCR producing K1 and the primers SEQ ID NO: 29 and SEQ ID NO: 30 were used in the PCR producing K4.

The amplified reading frames encoding K1 and K4 were at their 5'-ends, via the PCR-reaction, linked to nucleotide sequences, included in SEQ ID NO: 27 and SEQ ID NO: 29, encoding the amino acid sequence SEQ ID NO: 37 which constitutes a cleavage site for the bovine restriction protease $FX_a$ (Nagai and Thøgersen. Methods in Enzymology, 152:161–181, 1987). The amplified K1 DNA fragment was cloned into the *E. coli* expression vector pLcIIMLCH$_6$, which is modified from pLcIIMLC (Nagai et al., Nature, 332:284–286, 1988) by the insertion of an oligonucleotide encoding six histidinyl residues C-terminal of the myosin light chain fragment. The construction of the resulting plasmid pLcIIMLCH$_6$FX-K1 is outlined in FIG. 12. The amplified K4 DNA fragment was cloned into the *E. coli* expression vector pLcIIH$_6$, which is modified from pLcII (Nagai and Thøgersen. Methods in Enzymology, 152:461–481, 1987) by the insertion of an oligonucleotide encoding six histidinyl residues C-terminal of the cII fragment. The construction of the resulting plasmid pLcIIH$_6$FX-K4 is outlined in FIG. 13 and in FIG. 14 is shown the amino acid sequence of human "Glu" plasminogen (SEQ ID NO: 54).

Both the pLcIIMLCH$_6$-K1 plasmid and the pLcIIH$_6$FX-K4 plasmid were grown and expressed in *E. coli* QY13 cells as described in Nagai and Thøgersen. Methods in Enzymology, 152:461–481, 1987. Exponentially growing cultures at 30° C. were at OD$_{600}$ 1.0 transferred to 42° C. for 15 min. This heat shock induced synthesis of the fusion proteins. The cultures were further incubated at 37° C. for three to four hours before cells were harvested by centrifugation. Cells were lysed by osmotic shock and sonification and total cellular protein extracted into phenol (adjusted to pH 8 with Trisma base).

Crude protein was precipitated from the phenol phase by addition of 2.5 volumes of ethanol and centrifugation. The protein pellet was dissolved in a buffer containing 6M guanidinium chloride, 50 mM Tris-HCl pH 8 and 0.1M dithioerythriol. Following gel filtration on Sephadex G-25 (Pharmacia, Sweden) into 8M Urea, 1M NaCl, 50 mM Tris-HCl pH 8, 10 mM 2-mercaptoethanol, and 2 mM methionine the crude protein preparation was applied to a Ni$^{2+}$ activated NTA—agarose matrix for purification (Hochuli et al., 1988.) of the K1- and K-4-fusion proteins and subsequently to undergo the cyclic folding procedure.

All buffers prepared for liquid chromatography were degassed under vacuum prior to addition of reductant and/or use.

Preparation and "charging" of the Ni$^{2+}$NTA-agarose column is described under Example 1.

Upon application of the crude protein extracts on the Ni$^{2+}$NTA-agarose column, the fusion proteins were purified from the majority of *E. coli* and λ phage proteins by washing with one column volume of the loading buffer followed by 6M guanidinium chloride, 50 mM Tris-HCl, 10 mM 2-mercaptoethanol, and 2 mM methionine until the optical density (OD) at 280 nm of the column eluate was stable.

The fusion protein was refolded on the Ni$^{2+}$NTA-agarose column using a gradient manager profile as described in table 4 with 0.5M NaCl, 50 mM Tris-HCl pH 8, 10 mM 6 aminohexanoic acid (ε-aminocapronic acid, ε-ACA), 0.33 mM methionine, and 2.0 mM/0.2 reduced/oxidized glutathione as buffer A and 4M Urea, 0.5M NaCl, 50 mM Tris-HCl pH 8, 10 mM ε-ACA, 2 mM methionine, and 3 mM reduced glutathione as buffer B. The reduced/oxidized glutathione solution was freshly prepared as a 100 times stock solution by addition of 9.9M H$_2$O$_2$ to a stirred solution of 0.2M reduced glutathione before addition to buffer A.

After completion of the cyclic folding procedure each of the K1 and K4 fusion proteins were eluted from the Ni$^{2+}$ NTA-agarose column with a buffer containing 0.5M NaCl, 50 mM Tris-HCl, 5 mM EDTA pH 8. Fusion proteins that were aggregated and precipitated on the Ni$^{2+}$NTA-agarose column were eluted in buffer B.

Virtually all of the K1- and K4-fusion protein material was eluted from the Ni$^{2+}$NTA-agarose columns by the non-denaturing buffer. The estimated yields of K1-fusion protein and K4-fusion protein were approximately 60 mg. Virtually all of the K1-fusion protein as well as the K4-fusion protein appeared as nonomers as judged by non-reducing SDS-PAGE analysis corresponding to an efficiency of the folding procedure above 90%.

SDS-PAGE analysis of the production of recombinant plasminogen kringles 1 and 4 is presented in FIG. 17.

The K1-fusion protein and the K4-fusion protein were further purified by affinity chromatography on lysine-Sepharose CL-6B (Pharmacia, Sweden). The fusion proteins were eluted from the affinity columns by a buffer containing 0.5M NaCl, 50 mM Tris-HCl pH 8, 10 mM ε-ACA.

Binding to lysine-Sepharose is normally accepted as an indication of correct folding of lysine binding kringle domains.

The three dimensional structures of recombinant K1 and K4 protein domains, produced by this cyclic folding procedure and which have been fully processed by liberation from the N-terminal fusion tail and subsequently purified by ion exchange chromatography, have been confirmed by X-ray diffraction (performed by D. Robert Huber) and two dimensional NMR analysis (performed by stud. scient. Peter Reinholdt and Dr. Flemming Poulsen).

The general yield of fully processed recombinant K1 and K4 protein domains by this procedure is 5 mg/liter culture.

EXAMPLE 7

Production in *E. coli* and refolding of recombinant fragments derived from human $\alpha_2$-Macroglubolin and chicken Ovostatin This example describes the production in *E. coli* of the receptor-binding domain of human $\alpha_2$-Macroglobulin ($\alpha_2$-MRBDv) as a $FX_a$ cleavable fusion protein, and the purification of the recombinant $\alpha_2$-MRBDv after $FX_a$ cleavage.

The 462 bp DNA fragment encoding the $\alpha_2$-Macroglobulin reading frame from amino acid residues $Val_{1299}$ to $Ala_{1451}$ ($\alpha_2$-MRDv) was amplified in a Polymerase Chain Reaction (PCR), essentially following the protocol of Salki et al., (1988). pA2M (generously provided by Dr. T. Kristensen) containing the full length cDNA of human $\alpha_2$-Macroglobulin was used as template, and the oligonucleotides SEQ ID NO: 31 and SEQ ID NO: 32 as primers. The amplified coding reading frame was at the 5'-end, via the PCR-reaction, linked to a nucleotide sequence, included in SEQ ID NO: 7, encoding the amino acid sequence SEQ ID NO: 37 which constitute a cleavage site for the bovine restriction protease $FX_a$ (Nagai and Thøgersen, 1987). The amplified DNA fragment was subcloned into the *E. coli* expression vector $pT_7H_6$ (Christensen et al., 1991). The construction of the resulting plasmid $pT_7H_6FX$-$\alpha_2$MRDv (expressing human $\alpha_2$-MRDv) is outlined in FIG. 18 and the amino acid sequence of the expressed protein is shown in FIG. 19 (SEQ ID NO: 55).

Recombinant human $\alpha_2$-MRDv was produced by growing and expressing the plasmid $pT_7H_6FX$-$\alpha_2$MRDv in *E. coli* BL21 cells in a medium scale (2×1 liter) as described by Studier and Moffat, J. Mol. Biol., 189:113–130, 1986. Exponentially growing cultures at 37° C. were at $OD_{600}$ 0.8 infected with bacteriophage λCE6 at a multiplicity of approximately 5. Cultures were grown at 37° C. for another three hours before cells were harvested by centrifugation. Cells were lysed by osmotic shock and sonification and total cellular protein extracted into phenol (adjusted to pH 8 with Trisma base). Protein was precipitated from the phenol phase by addition of 2.5 volumes of ethanol and centrifugation. The protein pellet was dissolved in a buffer containing 6M guanidinium chloride, 50 mM Tris-HCl pH 8 and 50 mM dithioerythriol. Following gel filtration on Sephadex G-25 (Pharmacia, LKB, Sweden) into 8M Urea, 1M NaCl, 50 mM Tris-HCl pH 8, and 10 mM 2-mercaptocthanol the crude protein preparation was applied to a $Ni^{2+}$ activated NTA-agarose column ($Ni^{2+}$NTA-agarose) for purification (Hochuli et al., 1988) of the fusion protein, MGSHHHHHHGSIEGR-$\alpha_2$MRDv (wherein MGSHHHH-HHGSIEGR is SEQ ID NO: 48) and subsequently to undergo the cyclic folding procedure.

Preparation and "charging" of the $Ni^{2+}$NTA-agarose column is described under Example 1.

All buffers prepared for liquid chromatography were degassed under vacuum prior to addition of reductant and/or use.

Upon application of the crude protein extract on the $Ni^{2+}$NTA-agarose column, the fusion protein, MGSHHHHHHGSIEGR-$\alpha_2$MRDv (wherein MGSHHHH-HHGSIEGR is SEQ ID NO: 48) was purified from the majority of *E. coli* and λ phage proteins by washing with one column volume of the loading buffer followed by 6M guanidinium chloride, 50 mM Tris-HCl, and 10 mM 2-mercaptochthanol, until the optical density (OD) at 280 nm of the eluate was stable.

The fusion protein was refolded on the $Ni^{2+}$NTA-agarose column using a gradient manager profile as described in table 4 and 0.5M NaCl, 50 mM Tris-HCl pH 8, and 2.0 mM/0.2 mM reduced/oxidized glutathione as buffer A and 8M urea, 0.5M NaCl, 50 mM Tris-HCl pH 8, and 5 mM reduced glutathione as buffer B. The reduced/oxidized glutathione solution was freshly prepared as a 200 times stock solution by addition of 9.9M $H_2O_2$ to a stirred solution of 0.2M reduced glutathione before addition to buffer A.

After completion of the cyclic folding procedure the $\alpha_2$MRDv fusion protein was eluted from the $Ni^{2+}$NTA-agarose column with a buffer containing 0.5M NaCl, 50 mM Tris-HCl, 20 mM EDTA pH 8. Fusion protein that was aggregated and precipitated on the $Ni^{2+}$NTA-agarose column was eluted in buffer B.

Approximately 50% of the fusion protein material was eluted in the aqueous elution buffer. Half of this fusion protein material appeared monomeric and folded as judged by non-reducing SDS-PAGE analysis.

Recombinant $\alpha_2$MRDv protein was liberated from the N-terminal fusion tail by cleavage with the restriction protease $FX_a$ at room temperature in a weight to weight ratio of approximately 50 to one for four hours. After cleavage the $\alpha_2$MRDv protein was isolated from uncleaved fusion protein, the liberated fusion tail, and $FX_a$, by gelfiltration on Sephadex G-25 into 10 nM NaCl, 50 mM Tris-HCl pH 8, followed by ion exchange chromatography on Q-Sepharose: $\alpha_2$MRDv was eluted in a linear gradient (over 10 column volumes) from 10 mM NaCl, 10 mM Tris-HCl pH 8 to 500 mM NaCl, 10 mM Tris-HCl pH 8. The $\alpha_2$MRDv protein eluted at 150 mM NaCl.

The recombinant $\alpha_2$-MRDv domain binds to the $\alpha_2$-M receptor with a similar affinity for the receptor as exhibited by the complete $\alpha_2$-Macroglobulin molecule (referring to the estimated $K_D$ in one ligand-one receptor binding (Moestrup and Gliemann 1991). Binding analysis was performed by Dr. Søren K. Moestrup and stud. scient. Kåre Lehamnn).

EXAMPLE 8

Production in *E. coli* and refolding of recombinant fragments derived from the trout virus VHS envelope glycoprotein G Expression and in vitro refolding of recombinant fragments derived from the envelope glycoprotein G from the trout virus VHS in *E. coli* as $FX_a$ cleavable fusion proteins was performed using general strategies and methods analogous to those outlined in the general description of the "cyclic refolding procedure" and given in Examples 1 through 6.

EXAMPLE 9

Production in *E. coli* and refolding of recombinant human Tetranectin and recombinant fragments derived from human Tetranectin Tetranectin is a tetrameric protein consisting of four identical and non-covalently linked single chain subunits of 181 amino acid residues (17 kDa). Each subunit contains three disulphide bridges and binds $Ca^{2+}$. Tetranectin is found in plasma and associated with extracellular matrix. Tetranectin binds specifically to plasminogen kringle 4. This binding can specifically be titrated by lysine or ω-amino acids.

The cDNA encoding the reading frame corresponding to the mature tetranectin single chain subunit was cloned by specific amplification in a Polymerase Chain Reaction (PCR) (Saiki et al., 1988) of the nucleotide sequences from amino acid residue $Glu_1$ to $Val_{181}$ using 1st strand oligo-dT primed cDNA synthesized from total human placental RNA as template. Primers used in the PCR were SEQ ID NO: 33 and SEQ ID NO: 34. RNA extraction and cDNA synthesis were performed using standard procedures.

The amplified reading frame encoding the monomer subunit of tetranectin was at the 5'-end, via the PCR-reaction, linked to nucleotide sequences encoding the amino acid sequence SEQ ID NO: 37 which constitute a cleavage site for the bovine restriction protease $FX_a$ (Nagai, and Thøgersen, 1987). A glycine residue was, due to the specific design of the 5'-PCR primer (SEQ ID NO: 33), inserted between the C-terminal arginine residue of the $FX_a$ cleavage site (SEQ ID NO: 37) and the tetranectin $Glu_1$-residue. The amplified DNA fragment was subcloned into the E. coli expression vector $pT_7H_6$ (Christensen et al., 1991). The construction of the resulting plasmid $pT_7H_6$FX-TETN (expressing the tetranectin monomer) is outlined in FIG. 20 and the amino acid sequence of the expressed protein is shown in FIG. 21 (SEQ ID NO: 56).

To prepare the tetranectin monomer, the plasmid $pT_7H_6$FX-TETN was grown in medium scale (4×1 liter; 2×TY medium, 5 mM $MgSO_4$ and 100 μg ampicillin) in E. coli BL21 cells, as described by Studier and Moffat, J. Mol. Biol., 189:113–130, 1986. Exponentially growing cultures at 37° C. were at $OD_{600}$ 0.8 infected with bacteriophage λCE6 at a multiplicity of approximately 5. Cultures were grown at 37° C. for another three hours and the cells harvested by centrifugation. Cells were resuspended in 150 ml of 0.5M NaCl, 10 mM Tris HCl pH 8, and 1 mM EDTA pH 8. Phenol (100 ml adjusted to pH 8) was added and the mixture sonicated to extract the total protein. Protein was precipitated from the phenol phase by 2.5 volumes of ethanol and centrifugation.

The protein pellet was dissolved in a buffer containing 6M guanidinium chloride, 50 mM Tris-HCl pH 0 and 0.1M dithioerythriol. Following gel filtration on Sephadex G-25 (Pharmacia, LKB, Sweden) into 8M Urea, 1M NaCl, 50 mM Tris-HCl pH 8 and 10 mM 2-mercaptoethanol, the crude protein preparation was applied to a $Ni^{2+}$ activated NTA-agarose column ($Ni^{2+}$NTA-agarose, 75 ml pre-washed with 8M urea, 1M NaCl, 50 mM Tris-HCl, pH 8, and 10 mM 2-mercaptoethanol) for purification (Hochuli et al., 1988) of the fusion protein, MGSHHHHHHGSIEGR-TETN (wherein MGSHHHHHHGSIEGR is SEQ ID NO: 48).

Preparation and "charging" of the $Ni^{2+}$NTA-agarose column is described under example 1.

All buffers prepared for liquid chromatography were degassed under vacuum prior to addition of reductant and/or use.

The column was washed with 200 ml of 8M urea, 1M NaCl, 50 mM Tris-HCl pH 8, and 10 mM 2-mercaptoethanol (Buffer I) and 100 ml 6M guanidinium chloride, 50 mM Tris-HCl pH 8 and 10 mM 2-mercaptoethanol (Buffer II). The MGSHHHHHHGSIEGR-TETN fusion protein was eluted with Buffer II containing 10 mM EDTA pH 8 and the elute was gel filtered on Sephadex G25 using Buffer I as eluant.

The eluted protein was then refolded. The fusion protein MGSHHHHHHGSIEGR-TETN (wherein MGSHHHHH-HGSIEGR is SEQ ID NO: 48) was mixed with 100 ml $Ni^{2+}$NTA-agarose. The resin containing bound protein was packed into a 5 cm diameter column and washed with Buffer I supplemented with $CaCl_2$ to 2 mM. The fusion protein was refolded on the $Ni^{2+}$NTA-agarose column at 11°–12° C. using a gradient manager profile as described in table 4 and 0.5M NaCl, 50 mM Tris-HCl pH 8, 2 mM $CaCl_2$ and 2.0 mM/0.2 mM reduced/oxidized glutathione as buffer A and 8M urea, 1M NaCl, 50 mM Tris-HCl pH 8, 2 mM $CaCl_2$ and 3 mM reduced glutathione as buffer B. The reduced/oxidized glutathione solution was freshly prepared as a 200 times stock solution by addition of 9.9M $H_2O_2$ to a stirred solution of 0.2M reduced glutathione before addition to buffer A.

After completion of the cyclic folding procedure the tetranectin fusion protein was eluted from the $Ni^{2+}$NTA-agarose column with a buffer containing 0.5M NaCl, 50 mM Tris-HCl, 25 mM EDTA pH 8. The tetranectin fusion protein was cleaved with $FX_a$ at 4° C. overnight in a molar ratio of 1:300. After $FX_a$ cleavage the protein sample was concentrated 10 fold by ultrafiltration on a YM10 membrane (Amicon). Recombinant tetranectin was, after ten times dilution of the protein sample with 2 mM $CaCl_2$, isolated by ion-exchange chromatography on Q-Sepharose (Pharmacia, Sweden) in a linear gradient over 10 column volumes from 10 mM Tris-HCl pH 8, 2 mM $CaCl_2$ to 10 mM Tris-HCl pH 8, 2 mM $CaCl_2$, and 0.5M NaCl.

Recombinant tetranectin produced by this procedure was analyzed by Dr. Inge Clemmensen Rigohospitalet, Copenhagen. Dr. Clemmensen found that the recombinant tetranectin with respect to binding to plasminogen kringle 4 and expression of antigenic sites behaved identically to naturally isolated human tetranectin.

Preliminary experiments comparing the efficiency of refolding, using the "cyclic refolding procedure", of recombinant Tetranectin fusion protein bound to the $Ni^{2+}$NTA-agarose column versus recombinant Tetranectin contained in a dialysis bag indicate a significantly improved yield of soluble monomer from the solution refolding strategy. However, if either product of the cycling procedures is subjected to disulphide re-shuffling in solution in the presence of 5 mM $CaCl_2$ virtually all of the polypeptide material is converted to the correctly folded Tetranectin tetramer.

Denatured and reduced recombinant authentic Tetranectin contained in a dialysis bag, was refolded over 15 cyclic exposure to buffer B (6M Urea, 100 mM NaCl, 50 mM Tris-HCl pH=8, 2 mM/0.2 mM reduced/oxidized glutathione, 2 mM $CaCl_2$ and 0.5 mM methionine) and buffer A (100 mM NaCl, 50 mM Tris-HCl pH 8, 2 mM/0.2 mM reduced/oxidized glutathione, 2 mM $CaCl_2$, and 0.5 mM methionine).

EXAMPLE 10

Production and folding of a diabody expressed intracellularly in E. coli: Mab 32 diabody directed against tumour necrosis factor.

Diabodies (described in Holliger et al., 1993) are artificial bivalent and bispecific antibody fragments.

This example describes the production in E. coli of a diabody directed against tumour necrosis factor alpha (TNF-α), derived from the mouse monoclonal antibody Mab 32 (Rathjen et al., 1991, 1992; Australian Patent Appl. 7,576; EP-A-486,526).

A phagemid clone, pCANTAB5-myc-Mab32-5, containing Mab32 encoded in the diabody format (PCT/GB93/

02492) was generously provided by Dr. G. Winter, Cambridge Antibody Technology (CAT) Ltd., Cambridge, UK. pCANTAB5-myc-Mab32-5 DNA was used as template in a Polymerase Chain Reaction (PCR) (Saiki et al., 1988), using the primers SEQ ID NO: 35 and SEQ ID NO: 36, designed to produce a cDNA fragment corresponding to the complete artificial diabody. The amplified coding reading frame was at the 5'-end, via the PCR-reaction, linked to a nucleotide sequence, included in SEQ ID NO: 35, encoding the amino acid sequence SEQ ID NO: 37 which constitutes a cleavage site for the bovine restriction protease $FX_a$ (Nagai and Thøgersen, 1987). The amplified DNA fragment was subcloned into the *E. coli* expression vector $pT_7H_6$ (Christensen et al., 1991). The construction of the resulting plasmid $pT_7H_6FX$-DB32 (expressing the Mab32 diabody) is outlined in FIG. 22 and the amino acid sequence of the expressed protein is shown in FIG. 23 (SEQ ID NO: 57).

To prepare the diabody fragment, the plasmid $pT_7H_6FX$-DB32 was grown in medium scale (4×1 liter; 2×TY medium, 5 mM $MgSO_4$ and 100 μg ampicillin) in *E. coli* BL21 cells, as described by Studier and Moffat, J. Mol. Biol., 189:113 130, 1986. Exponentially growing cultures at 37° C. were at $OD_{600}$ 0.8 infected with bacteriophage λCE6 at a multiplicity of approximately 5. Forty minutes after infection, rifampicin was added (0.2 g in 2 ml methanol per liter media). Cultures were grown at 37° C. for another three hours and the cells harvested by centrifugation. Cells were resuspended in 150 ml of 0.5M NaCl, 10 mM Tris-HCl, pH 8, and 1 mM EDTA pH 8. Phenol (100 ml adjusted to pH 8) was added and the mixture sonicated to extract the total protein. Protein was precipitated from the phenol phase by 2.5 volumes of ethanol and centrifugation.

The protein pellet was dissolved in a buffer containing 6M guanidinium chloride, 50 mM Tris-HCl pH 8 and 0.1M dithioerythriol. Following gel filtration on Sephadex G-25 (Pharmacia, LKB, Sweden) into 8M Urea, 1M NaCl, 50 mM Tris-HCl pH 8 and 10 mM 2-mercaptoethanol, the crude protein preparation was applied to a $Ni^{2+}$ activated NTA-agarose column ($Ni^{2+}$NTA-agarose, 75 ml pre-washed with 8M urea, 1M NaCl, 50 mM Tris-HCl pH 8, and 10 mM 2-mercaptoethanol) for purification (Hochuli et al., 1988) of the fusion protein, MGSHHHHHHGSIEGR-DB32 (wherein MGSHHHHHHGSIEGR is SEQ ID NO: 48).

Preparation and "charging" of the $Ni^{2+}$NTA-agarose column is described under example 1.

All buffers prepared for liquid chromatography were degassed under vacuum prior to addition of reductant and/or use.

The column was washed with 200 ml of 0M urea, 1M NaCl, 50 mM Tris-HCl pH 8, and 10 mM 2-mercaptoethanol (Buffer I) and 100 ml 6M guanidinium chloride, 50 mM Tris HCl pH 8 and 10 mM 2-mercaptoethanol (Buffer II). The MGSHHHHHHGSIEGR-DB32 fusion protein was eluted with Buffer II containing 10 mM EDTA pH 8 and the elute was gel filtered on Sephadex G25 using Buffer I as eluant.

The protein eluted was then refolded. The fusion protein MGSHHHHHHGSIEGR-DB32 (wherein MGSHHHHHH-GSIEGR is SEQ ID NO: 48) was mixed with 100 ml $Ni^{2+}$NTA-agarose. The resin containing bound protein was packed into a 5 cm diameter column and washed with Buffer I. The fusion protein was refolded on the $Ni^{2+}$NTA-agarose column at 11°–12° C. using a gradient manager profile was descried in table 4 and 0.5M NaCl, 50 mM Tris-HCl pH 8, and 2.0 mM/0.2 mM reduced/oxidized glutathione as buffer A and 8M urea, 1M NaCl, 50 mM Tris-HCl pH 8, and 3 mM reduced glutathione as buffer B. The reduced/oxidized glutathione solution was freshly prepared as a 200 times stock solution by addition of 9.9M $H_2O_2$ to a stirred solution of 0.2M reduced glutathione before addition to buffer A.

After completion of the cyclic folding procedure the DB32 fusion protein was eluted from the $Ni^{2+}$NTA-agarose column with a buffer containing 0.5M NaCl, 50 mM Tris-HCl, 25 mM EDTA pH 8 and adjusted to 5 mM GSH, 0.5 mM GSSG and incubated for 12 to 15 hours at 20° C. The fusion protein was then concentrated 50 fold by ultrafiltration using YM10 membranes and clarified by centrifugation.

The DB32 fusion protein dimer was purified by gel filtration using a Superose 12 column (Pharmacia, Sweden) with PBS as eluant.

The overall yield of correctly folded DB32 fusion protein from this procedure was 4 mg per liter.

An analysis by non-reducing SDS-PAGE from different stages of the purification is shown in FIG. 26.

The MGSHHHHHHGSIEGR (SEQ ID NO: 48) N-terminal fusion peptide was cleaved off the DB32 protein by cleavage with the restriction protease $FX_a$ (molar ratio 1:5 $FX_a$:DB32 fusion protein) at 37° C. for 20 hours. This is shown as the appearance of a lower molecular weight band just below the uncleaved fusion protein in FIG. 26.

The refolded DB32 protein was analyzed by Cambridge Antibody Technology Ltd. (CAT). DB32 was found to bind specifically to TNF-α and to compete with the Mab32 whole antibody for binding to TNF-α. Furthermore both DB32 and Mab32 were competed in binding to TNA-α by sheep anti-301 antiserum, which had been raised by immunizing sheep with a peptide encoding the first 18 amino acids of human TNF-α and comprised at least part of the epitope recognised by the murine Mab32.

EXAMPLE 11

Production and refolding of human psoriasin in *E. coli*.

Psoriasin is a single domain $Ca^{2+}$-binding protein of 100 amino acid residues (11.5 kDa). Psoriasin contains a single disulphide bridge. The protein which is believed to be a member of the S100 Protein family is highly up-regulated in psoriatic skin and in primary human keratinocytes undergoing abnormal differentiation.

The plasmid $pT_7H_6FX$-PS.4 (kindly provided by Dr. P. Madsen, Institute of Medical Biochemistry, University of Aarhus, Denmark) has previously been described by Hoffmann et al., (1994). The nucleotide sequence encoding the psoriasin protein from $Ser_2$ to $Gln_{101}$ is in the 5'-end linked to the nucleotide sequence encoding the amino acid sequence MGSHHHHHHGSIEGR (SEQ ID NO: 48). A map of $pT_7H_6FX$-PS.4 is given in FIG. 24 and the amino acid sequence of human psoriasin is listed in FIG. 25 (SEQ ID NO: 58).

Recombinant human psoriasin was grown and expressed from the plasmid $pT_7H_6FX$-PS.4 in *E. coli* BL21 cells and total cellular protein extracted as described (Hoffmann et al., 1994). Ethanol precipitated total protein was dissolved in a buffer containing 6M guanidinium chloride, 50 mM Tris-HCl pH 8 and 50 mM dithioerythriol. Following gel filtration on Sephadex G-25 (Pharmacia, LKB, Sweden) into 8M Urea, 0.5M NaCl, 50 mM Tris-HCl pH 8 and 5 mM 2-mercaptoethanol the crude protein preparation was applied to a $Ni^{2+}$ activated NTA agarose column ($Ni^{2+}$NTA-agarose) for purification (Hochuli et al., 1988) of the fusion protein, MGSHHHHHHGSIEGR-psoriasin (wherein MCSHHHHHHCSIECR is SEQ ID NO: 48) and subsequently to undergo the cyclic folding procedure.

Preparation and "charging" of the Ni$^{2+}$NTA-agarose column is described under Example 1.

All buffers prepared for liquid chromatography were degassed under vacuum prior to addition of reductant and/or use.

Upon application of the crude protein extract on the Ni$^{2+}$NTA-agarose column, the fusion protein, MGSHHHHHHGSIEGR-psoriasin (wherein MGSHHHH-HHGSIEGR is SEQ ID NO: 48) was purified from the majority of E. coli and λ phage proteins by washing with one column volume of the loading buffer followed by 6M guanidinium chloride, 50 mM Tris-HCl, and 5 mM 2-mercaptoethanol until the optical density (OD) at 280 nm of the eluate was stable.

The fusion protein was refolded on the Ni$^{2+}$NTA-agarose column using a gradient manager profile as described in table 4 and 0.5M NaCl, 50 mM Tris HCl pH 8, 2 mM CaCl$_2$ and 1.0 mM/0.1 mM reduced/oxidized glutathione as buffer A and 8M urea, 0.5M NaCl, 50 mM Tris-HCl pH 8, 2 mM CaCl$_2$ and 5 mM reduced glutathione as buffer B. The reduced/oxidized glutathione solution was freshly prepared as a 200 times stock solution by addition of 9.9M H$_2$O$_2$ to a stirred solution of 0.2M reduced glutathione before addition to buffer A.

After completion of the cyclic folding procedure the psoriasin fusion protein was eluted from the Ni$^{2+}$NTA-agarose column with a buffer containing 0.5M NaCl, 50 mM Tris-HCl, 10 mM EDTA pH 8. Fusion protein that was aggregated and precipitated on the Ni$^{2+}$NTA-agarose column was eluted in buffer B.

Approximately 95% of the fusion protein material was eluted by the non-denaturing elution buffer. As judged by non-reducing SDS-PAGE analysis 75% of the soluble fusion protein material appeared to be monomeric yielding an overall efficiency of the folding procedure of approximately 70%. The efficiency of the previously described refolding procedure for production of recombinant human peoriasin (Hoffman et al., 1994) was estimated to be less than 25%.

The psoriasin fusion protein was cleaved with FX$_a$ in a molar ratio of 100:1 for 48 hrs at room temperature. After gelfiltration into a buffer containing 20 mM Na-acetate pH 5 and 20 mM NaCl on Sephadex G-25 the protein sample was applied onto an S-Sepharose ion exchange column (Pharmacia). Monomeric recombinant psoriasin was eluted over 5 column volumes with a linear gradient from 20 mM Na acetate pH 5, 20 mM NaCl to 0.5M NaCl. Monomeric psoriasin eluted at 150 mM NaCl. Dimeric and higher order multimers of psoriasin together with uncleaved fusion protein eluted later in the gradient. Fractions containing the cleaved purified recombinant protein were gelfiltrated on Sephadex G25 into a buffer containing 150 mM NaCl, 10 mM Tris-HCl pH 7.4 and stored at 4° C.

EXAMPLE 12

Evaluation procedure for suitability testing of thiol compounds for use as reducing agents in cyclic refolding and determination of optimal levels of denaturants and disulphide reshuffling agents for optimization of cyclic refolding procedures.

In order to improve the yield of correctly folded protein obtainable from cyclic refolding the number of productive cycles should be maximized (see SUMMARY OF THE INVENTION). Productive cycles are characterized by steps of denaturation where misfolded protein, en route to dead-end aggregate conformational states, is salvaged into unfolded conformational states while most of the already correctly folded protein remains in conformational states able to snap back into the refolded state during the refolding step of the cycle.

A number of disulphide bridge containing proteins, like $\beta_2$-microglobulin, are known to refold with high efficiency (>95%) when subjected to high levels of denaturing agents as long as their disulphide bridges remain intact.

This example describes how to evaluate suitability of a thiol compound for use in cyclic refolding on the basis of its ability to discriminate correct from incorrect disulphide bridges and how to optimize levels of denaturing agent and/or reducing agent to be used in the denaturation steps in order to maximize the number of productive cycles. As model systems we chose a mixture of mono-, di- and multimeric forms of purified recombinant human $\beta_2$-microglobulin. Our specific aim was to analyze the stability of different topological forms of human $\beta_2$-microglobulin against reduction by five different reducing agents at various concentrations of denaturing agent.

Human $\beta_2$-micorglobulin (produced as described in Example 13) in 6M guanidinium chloride, 50 mM Tris-HCl and 10 mM 2-mercaptoethanol pH 8 was gelfiltrated into non-denaturing buffer (50 mM Tris-HCl, 0.5M NaCl pH 8). Only a fraction of the protein in the sample was soluble in the non-denaturing buffer. After 48 hours exposure to air, the protein solution appeared unclear. Non-reducing SDS-PAGE analysis showed that most of the protein had been oxidized into multimeric forms and only a small fraction was oxidized and monomeric (FIG. 27, lane 1).

The protein solution was aliquoted into a number of tubes and varying amounts of urea added while keeping the concentration of protein and salt at a constant level.

Reducing agent, either glutathione, cysteine ethyl ester, N-acetyl-L-cysteine, mercaptosuccinic acid or 2-mercaptoethanol was added to the ensemble of protein samples with varying urea concentrations. Each reducing agents was added to a final concentration of 4 mM. The protein samples were incubated at room temperature for 10 min and then free thiol groups were blocked by addition of iodoacetic acid to a final concentration of 12 mM. Finally, the protein samples were analyzed by non-reducing SDS-PAGE (FIGS. 17–32). The compositions of the test-samples used in the non-reducing SDS-PAGE as well as the results are given below in the following tables; in the rows indicating the ability of the chosen reducing agent to reduce disulphide bridges the marking "+++" indicates good ability, "" indicates intermediate ability, "+" indicates weak ability, whereas no marking indicates that no measurable effect could be observed.

| Composition of samples used in SDS-PAGE of FIG. 27 | | | | | | | | | | | |
|---|---|---|---|---|---|---|---|---|---|---|---|
| Test no. | 1 | 2 | 3 | 4 | 5 | 6 | 7 | 8 | 9 | 10 | 11 |
| μl protein solution | 36 | 36 | 36 | 36 | 36 | 36 | 36 | 36 | 36 | 36 | 36 |
| μl Buffer A | 160 | 160 | 140 | 120 | 100 | 80 | 70 | 60 | 50 | 40 | 20 |
| μl Buffer B | 0 | 0 | 20 | 40 | 60 | 80 | 90 | 100 | 110 | 120 | 140 |
| μl GSH | 0 | 4 | 4 | 4 | 4 | 4 | 4 | 4 | 4 | 4 | 4 |

Composition of samples used in SDS-PAGE of FIG. 27

| Test no. | 1 | 2 | 3 | 4 | 5 | 6 | 7 | 8 | 9 | 10 | 11 |
|---|---|---|---|---|---|---|---|---|---|---|---|
| M urea | 0 | 0 | 1 | 2 | 3 | 4 | 4.5 | 5 | 5.5 | 6 | 7 |
| Ability to reduce wrong disulphide bridges | | | I | I | II | II | III | III | III | III | III |
| Ability to reduce correct disulphide bridges | | | | | | | | | | + | +++ |

Buffer A: 50 mM Tris.HCl pH 8, 0.5 M NACl
Buffer B: 10 M urea, 50 mM Tris.HCl pH 8, 0.5 M NaCl
GSII: 0.2 M Gluthatione
Protein solution: 2 mg/ml h$\beta_2$m, 50 mM Tris.HCl pH 8, 0.5 M NaCl

Composition of samples used in SDS-PAGE of FIG. 28

| Test no. | 1 | 2 | 3 | 4 | 5 | 6 | 7 | 8 | 9 |
|---|---|---|---|---|---|---|---|---|---|
| μl protein solution | 36 | 36 | 36 | 36 | 36 | 36 | 36 | 36 | 36 |
| μl Buffer A | 160 | 160 | 140 | 120 | 100 | 80 | 60 | 40 | 20 |
| μl Buffer B | 0 | 0 | 20 | 40 | 60 | 80 | 100 | 120 | 140 |
| μl CE | 0 | 4 | 4 | 4 | 4 | 4 | 4 | 4 | 4 |
| M urea | 0 | 0 | 1 | 2 | 3 | 4 | 5 | 6 | 7 |
| Ability to reduce wrong disulphide bridges | | ++ | ++ | ++ | +++ | +++ | +++ | +++ | +++ |
| Ability to reduce correct disulphide bridges | | | | | | | ++ | +++ | +++ |

Buffer A: 50 mM Tris.HCl pH 8, 0.5 M NaCl
Buffer B: 10 M urea, 50 mM Tris.HCl pH 8, 0.5 M NaCl
CE: 0.2 M L-cysteine ethyl ester
Protein solution: 2 mg/ml h$\beta_2$m, 50 mM Tris.HCl pH 8, 0.5 M NaCl

Composition of samples used in SDS-PAGE of FIG. 29

| Test no. | 1 | 2 | 3 | 4 | 5 | 6 | 7 | 8 | 9 |
|---|---|---|---|---|---|---|---|---|---|
| μl protein solution | 36 | 36 | 36 | 36 | 36 | 36 | 36 | 36 | 36 |
| μl Buffer A | 160 | 160 | 140 | 120 | 100 | 80 | 60 | 40 | 20 |
| μl Buffer B | 0 | 0 | 20 | 40 | 60 | 80 | 100 | 120 | 140 |
| μl ME | 0 | 4 | 4 | 4 | 4 | 4 | 4 | 4 | 4 |
| M urea | 0 | 0 | 1 | 2 | 3 | 4 | 5 | 6 | 7 |
| Ability to reduce wrong disulphide bridges | | ++ | ++ | ++ | +++ | +++ | +++ | +++ | +++ |
| Ability to reduce correct disulphide bridges | | | | | | + | ++ | +++ | +++ |

Buffer A: 50 mM Tris.HCl pH 8, 0.5 M NaCl
Buffer B: 10 M urea, 50 mM Tris.HCl pH 8, 0.5 M NaCl
ME: 0.2 M 2-mercaptoethanol
Protein solution: 2 mg/ml h$\beta_2$m, 50 mM Tris.HCl pH 8, 0.5 M NaCl

Composition of samples used in SDS-PAGE of FIG. 30

| Test no. | 1 | 2 | 3 | 4 | 5 | 6 | 7 | 8 | 9 |
|---|---|---|---|---|---|---|---|---|---|
| μl protein solution | 36 | 36 | 36 | 36 | 36 | 36 | 36 | 36 | 36 |
| μl Buffer A | 160 | 160 | 140 | 120 | 100 | 80 | 60 | 40 | 20 |
| μl Buffer B | 0 | 0 | 20 | 40 | 60 | 80 | 100 | 120 | 140 |

| Composition of samples used in SDS-PAGE of FIG. 30 | | | | | | | | | |
|---|---|---|---|---|---|---|---|---|---|
| Test no. | 1 | 2 | 3 | 4 | 5 | 6 | 7 | 8 | 9 |
| µl MSA | 0 | 4 | 4 | 4 | 4 | 4 | 4 | 4 | 4 |
| M urea | 0 | 0 | 1 | 2 | 3 | 4 | 5 | 6 | 7 |
| Ability to reduce wrong disulphide bridges | | ++ | ++ | ++ | ++ | ++ | +++ | +++ | +++ |
| Ability to reduce correct disulphide bridges | | | | | | | ++ | +++ | +++ |

Buffer A: 50 mM Tris.HCl pH 8, 0.5 M NaCl
Buffer B: 10 M urea, 50 mM Tris.HCl pH 8, 0.5 M NaCl
MSA: 0.2 M Mercaptosuccinic acid
Protein solution: 2 mg/ml h$\beta_2$m, 50 mM Tris.HCl pH 8, 0.5 M NaCl

| Composition of samples used in SDS-PAGE of FIG. 31 | | | | | | | | | |
|---|---|---|---|---|---|---|---|---|---|
| Test no. | 1 | 2 | 3 | 4 | 5 | 6 | 7 | 8 | 9 |
| µl protein solution | 36 | 36 | 36 | 36 | 36 | 36 | 36 | 36 | 36 |
| µl Buffer A | 160 | 160 | 140 | 120 | 100 | 80 | 60 | 40 | 20 |
| µl Buffer B | 0 | 0 | 20 | 40 | 60 | 80 | 100 | 120 | 140 |
| µl AC | 0 | 4 | 4 | 4 | 4 | 4 | 4 | 4 | 4 |
| M urea | 0 | 0 | 1 | 2 | 3 | 4 | 5 | 6 | 7 |
| Ability to reduce wrong disulphide bridges | | + | ++ | ++ | +++ | +++ | +++ | +++ | +++ |
| Ability to reduce correct disulphide bridges | | | | | | + | ++ | +++ | +++ | +++ |

Buffer A: 50 mM Tris.HCl pH 8, 0.5 M NaCl
Buffer B: 10 M urea, 50 mM Tris.HCl pH 8, 0.5 M NaCl
AC: 0.2 M N-acetyl-L-cysteine
Protein solution: 2 mg/ml h$\beta_2$m, 50 mM Tris.HCl pH 8, 0.5 M NaCl The different topological forms of $\beta_1$-m may be separated by non-reducing SDS-PAGE gel electrophoresis. The fastest migrating band represents the oxidized monomeric form. This band is immediately followed by the reduced $\beta_2$-m with a slightly slower migration rate, whereas the multimeric forms of the protein are migrating much slower in the gel.

In this analysis we are probing for the ability of each of the five reducing agents tested, to reduce the disulphide bridges of multimeric forms of $\beta_2$-microglobulin without significantly reducing the correctly formed disulphide bridge of the monomeric oxidized form.

The results from the analyses (FIGS. 27–32) are, in summary, as follows: N-acetyl-L-cysteine and mercaptosuccinic acid are, under the conditions used, essentially unable to discriminate correct and incorrect disulphide bridges. Glutathione, cysteine ethyl ester and 2-mercaptoethanol are all capable of—within 10 min and within individual characteristic ranges of urea concentrations significantly reducing disulphide bridges of multimeric forms while most of the oxidised monomeric $\beta_2$-m remains in the oxidised form. Glutothione has clearly the capacity of selectively reducing incorrect disulphide bridges at higher concentrations of urea compared to cysteine ethyl ester and 2-mercaptoethanol and therefore glutathione among the selection of thiols tested would be the reducing agent of choice for cyclic refolding of human $\beta_2$-microglobulin. As a consequence of these experiments the concentration of urea in the reducing buffer B for the refolding procedure used in Example 13 was lowered from 8M (Example 1) to 6M, which led to an improvement of overall refolding yield of human $\beta_2$-microglobulin from 53% to 87%.

EXAMPLE 13

Refolding of purified human $\beta_2$-microglobulin: Comparative analysis of three refolding procedures The following set of experiments were undertaken to obtain comparable quantitative data to evaluate the importance of cycling for refolding yield versus simple refolding procedures involving a stepwise or a gradual one-pass transition from strongly denaturing and reducing conditions to non-denaturing and non-reducing conditions.

Purified refolded recombinant human $\beta_2$-microglobulin fusion protein, obtained as described in EXAMPLE 1, was reduced and denatured to obtain starting materials devoid of impurities, such as proteolytic breakdown products or minor fractions of fusion protein damaged by irreversible oxidation or other chemical derivatization.

In a first step the optimization procedure described in EXAMPLE 12 was used to modify the conditions for cyclic refolding described in EXAMPLE 1 to increase the number of productive cycles. The optimized refolding protocol was identical to that described in EXAMPLE 1, as were buffers and other experimental parameters, except that the Buffer B in the present experiments was 6M urea, 50 mM Tris-HCl pH 8, 0.5M NaCl, 4 mM glutathione.

Three batches of pure fusion protein were refolded while attached to $Ni^{++}$-loaded NTA-agarose as described in EXAMPLE 1, using the present Buffer B composition. One batch was submitted to buffer cycling as described in EXAMPLE 1, for batch two and three cycling was replaced by a monotonous linear buffer gradient (100% B to 0% B over 24 hours) and a step gradient (100% B to 0% B in one step, followed by 0% B buffer for 24 hours), respectively. In each refolding experiment all of the polypeptide material was recovered as described in EXAMPLE 1 as a soluble fraction elutable under non-denaturing conditions and a remaining insoluble fraction elutable only under denaturing and reducing conditions. The yields of correctly folded fusion protein were then measured by quantitative densitometric analysis (Optical scanner HW and CS 370 Densitometric Analysis SW package from Hoeffer Scientific, CA, U.S.A.) of Coomassie stained SDS-PAGE gels on which suitably diluted measured aliquots of soluble and insoluble fractions had been separated under reducing or non-reducing conditions, as required to allow separation of correctly disulphide-bridged monomer from soluble polymers in soluble fractions. Where required to obtain reliable densitometric data both for intense and faint bands in a gel lane several sample dilutions were scanned and analysed to obtain re-scaled data sets.

EXPERIMENTAL DETAILS AND RESULTS

Purified Denatured and Reduced Fusion Protein

A batch of human $\beta_2$-microglobulin fusion protein was refolded as described in EXAMPLE 1. 96% of the fusion protein was recovered in the soluble fraction (FIG. 32, lanes 2–5). 56% of this soluble fraction was in the monomeric and disulphide-bridged form. Hence, the overall refolding efficiency obtained was 53%. Monomeric fusion protein was purified from multimers by ion exchange chromatography on S-Sepharose (Pharmacia, Sweden): The soluble fraction obtained after refolding was gel filtered on Sephadex G-25 (Pharmacia, Sweden) into a buffer containing 5 mM NaCl and 5 mM Tris-HCl pH 8, diluted to double volume with water and then applied to the S-Sepharose column, which was then eluted using a gradient (5 column volumes from 2.5 mM Tris-HCl pH 8, 2.5 mM NaCl to 25 mM Tris-HCl pH 8, 100 mM NaCl). The monomeric correctly folded fusion protein purified to >95% purity (FIG. 32, lanes 6 and 7) was then made 6M in guanidinium hydrochloride and 0.1M in DTE, gel filtrated into a buffer containing 8M urea, 50 mM Tris-HCl pH 8, 1M NaCl and 10 mM 2-mercaptoethanol and then divided into aliquots to be used as starting material for the refolding experiments described below.

Cyclic Refolding of Purified Fusion Protein

An aliquot of denatured reduced fusion protein was applied to a $Ni^{++}$loaded NTA column which was then washed with one column volume of a buffer containing 6M guanidinium hydrochloride, 50 mM Tris-HCl pH 8 and 10 mM 2 -mercaptoethanol.

The fusion protein was then subjected to buffer cycling according to the scheme shown in Table 1 using Buffer A: 50 mM Tris-HCl pH 8, 0.5M NaCl and 3.2 mM/0.4 mM reduced/oxidized glutathione and Buffer B: 50 mM Tris-HCl pH 8, 0.5M NaCl, 6M urea and 4 mM reduced glutathione. After completion of buffer cycling the fusion protein was recovered quantitatively in a soluble form by elution of the column with a buffer containing 50 mM Tris-HCl pH 8, 0.5M NaCl and 20 mN EDTA. 87% was obtained in the correct monomeric disulphide-bridged form (FIG. 32 lanes 8 and 9).

Refolding of Purified Fusion Protein by Linear Gradient

An aliquot of denatured reduced fusion protein was applied to a $Ni^{++}$-loaded NTA column which was then washed with one column volume of a buffer containing 6M guanidinium hydrochloride, 50 mM Tris-HCl pH 8 and 10 mM 2-mercaptoethanol followed by 1 column volume of a buffer containing 50 mM Tris-HCl pH 8, 0.5M NaCl, 6M urea and 4 mM reduced glutathione.

A 24 hour linear gradient from 100% B to 100% A was then applied at 2 ml/min, using Buffer A: 50 mM Tris-HCl pH 8, 0.5M NaCl and 3.2 mM/0.4 mM reduced/oxidized glutathione and Buffer B: 50 mM Tris-HCl pH 8, 0.5M NaCl, 6M urea and 4 mM reduced glutathione. After completion of the gradient the soluble fraction of fusion protein was eluted in a buffer containing 50 mM Tris-HCl pH 8, 0.5M NaCl and 20 mM EDTA. The remaining insoluble fraction was extracted from the column in a buffer containing 50 mM Tris-HCl pH 8, 1M NaCl, 8M urea, 10 mM 2-mercaptoethanol and 20 mM EDTA.

48% of the fusion protein was recovered in the soluble fraction and 60% of the soluble fraction was recovered in the correct monomeric disulphide-bridged form. The overall efficiency of folding obtained was therefore 29% (FIG. 33, lanes 5–7).

Refolding of Purified Fusion Protein by Buffer Step

An aliquot of denatured reduced fusion protein was applied to a $Ni^{++}$-loaded NTA column which was then washed with one column volume of a buffer containing 6M guanidinium hydrochloride, 50 mM Tris-HCl pH 8 and 10 mM 2-mercaptoethanol.

Buffer containing 50 mM Tris-HCl pH 8, 0.5M NaCl and 3.2 mM/0.4 mM reduced/oxidized glutathione was then applied to the column at 2 ml/min for 24 hours before recovering the soluble fraction of fusion protein in a buffer containing 50 mM Tris-HCl pH 8, 0.5M NaCl and 20 mM EDTA. The remaining insoluble fraction was extracted from column in a buffer containing 50 mM Tris-HCl pH 8, 1M NaCl, 8M urea, 10 mM 2-mercaptoethanol and 20 mM EDTA.

34% of the fusion protein was recovered in the soluble fraction and 28% of the soluble fraction was recovered in the correct monomeric disulphide-bridged form. The overall efficiency of folding was therefore 9.5%, (FIG. 33, lanes 1–3).

Conclusions

In summary, using human $\beta_2$-microglobulin as a model protein, it may be concluded that (a) straightforward buffer optimization and improved purification of fusion protein prior to cyclic refolding increased refolding yield significantly (from 53% to 87%) and (b) progressive denaturation—renaturation cycling is superior to single-pass refolding under otherwise comparable experimental conditions by a very large factor (87% versus 29% or 9.5% yields).

REFERENCES

Christensen, J. H., Hansen, P. K., Lillelund, O., and Thøgersen, H. C. (1991). Sequence-specific binding of the N-terminal three-finger fragment of Xenopus transcription factor IIIA to the internal control region of a 5S RNA gene. *FEBS Letters*, 295:181–184.

Dalbøge, H., Dahl, H. -H., M., Pedersen, J., Hansen, J., W., and T., Kristensen (1987). A Novel Enzymatic Method for Production of Authentic hGH From an *Eschericia coli* Produced hGh-Precursor. *Bio/Technology*, 5:161–164.

Datar, R., V., Cartwright, T., and C. -G. Rosen (1993). Process Economics of Animal Cell and Bacterial Fermentations: A Case Study Analysis of Tissue Plasminogen Activator. *Bio/Technology*, 11:349–357.

Hers, J., Hanmann, U., Rogne, S., Myklebost, O., Gausepohl, H., and Stanley, K. K. (1988), Surface location and high affinity for calcium of a 500 kd liver membrane protein closely related to the LDL-receptor suggest a physiological role as lipoprotein receptor. *EMBO J.*, 7:4119–4137.

Hoffmann, H. J., Olsen, E., Etzerodt, M., Madsen, P., Thøgersen, H. C., Kruse, T., and Celis J. E. (1994). Psoriasin Binds Calcium and Is Differentially Regulated With Respect to Other Members of the S100 Protein Family. *J. Dermatol. Invest.* in press.

Hochuli, E., W. Bannwarth, H. Döbeli, R. Gentz, and D. Stüber. 1988. Genetic approach to facilitate purification of recombinant proteins with a novel metal chelate adsorbent. *Bio/Technology*, 6:1321–1325.

Holliger., P., Prospero, T., and G. Winter (1993). "Diabodies": Small bivalent and bispecific antibody fragments. *Proc. Natl. Acad. Sci. U.S.A.* 90:6444–6448.

Maniatis, T., E. F. Fritsch, and J. Sambrook. 1982. *Molecular cloning*. Cold Spring Harbor Labroatory, Cold Spring Harbor, N.Y.

Nagai, K., and H. C. Thøgersen. 1987. Synthesis and Sequence-Specific Proteolysis of Hybrid Proteins Produced in *Escherichia coli*. *Methods in Enzymology*, 152:461–481.

Nagai, K., Nakaseko, Y., Nasmyth, K., and Rhodes, D. (1988). Zinc-finger motifs expressed in *E. coli* and folded in vitro direct specific binding to DNA. *Nature*, 332:284–286.

Nykjær A., Petersen C. M., Møller B., Jensen P. H., Moestrup S. K., Holtet T. L., Etzerodt M., Thøgersen H. C., Munch M., Andreasen P. A., and Gliemann J. (1992). Purified $\alpha_2$-Macroglobulin Receptor/LDL Receptor-related Protein Binds Urokinase-Plasminogen Activator Inhibitor Type-1 Complex. *J. Biol. Chem.* 267:14543–14546.

Rathjen, D. et al. (1991), *Mol. Immunol.* 28, p29.

Rathjen, D. et al. (1992), *Brit. J. Cancer* 65, 852–856.

Saiki, R. K., Gelfant, D. H., Stoffel, S., Scharf, S. J., Higuchi, R., Horn, G. T., Mullis, K. B., and Erlich, H. A. (1988). Primer-directed enzymatic amplification of DNA with a thermostable DNA polymerase. *Science* 239:487–491.

Studier, F. W. and Moffat, B. A. 1986. Use of Bacteriophage T7 RNA Polymerase to Direct Selective High level Expression of Cloned Genes. *J. Mol. Biol.*, 189:113–130.

The Regents of the University of California. Enterokinase—cleavable linker sequence. EP 035384.

---

We claim:

1. A method for generating a processed ensemble of polypeptide molecules, in which processed ensemble the conformational states represented contain a substantial fraction of polypeptide molecules in one particular folded conformation, from an initial ensemble of polypeptide molecules which have the same amino acid sequence as the processed ensemble of polypeptide molecules, in which initial ensemble the conformation states represented contain a substantial fraction of polypeptide molecules in unfolded or misfolded conformations, the method comprising subjecting the initial ensemble of polypeptide molecules to a series of at least three successive cycles, each of which comprises a sequence of 1) at least one denaturing step comprising conditions exerting a denaturing or unfolding influence on the polypeptide molecules of the ensemble so as to denature or unfold a fraction of the polypeptides in the ensemble, followed by, 2) at least one renaturing step comprising conditions having a renaturing influence on the polypeptide molecules having conformations resulting from the preceding step so as to renature a fraction of the denatured or or unfolded polypeptides in the ensemble, the series of at least three successive cycles being performed under conditions where in at least one denaturing step in the series a smaller proportion of the polypeptides in the ensemble is denatured or unfolded than in an earlier denaturing step in the series so that the processed ensemble of the polypeptide molecules has a higher fraction of polypeptide molecules in the particular folded conformation than a) the initial ensemble, and b) an initial ensemble which has been subjected to one of the cycles only.

2. A method according to claim 1, wherein the substantial fraction of polypeptide molecules in one particular folded conformation constitutes at least 5% (w/w) of the initial ensemble of polypeptide molecules.

3. A method according to claim 2, wherein the polypeptide molecules of the processed ensemble comprise cysteine-containing molecules, and the processed ensemble comprises a substantial fraction of polypeptide molecules in one particular uniform conformation which, in addition have substantially identical disulphide bridging topology.

4. A method according to claim 1, wherein the polypeptide molecules are molecules which have an amino acid sequence identical to that of an authentic polypeptide, or are molecules which comprise an amino acid sequence corresponding to that of an authentic polypeptide joined to one or two additional polypeptide segments.

5. A method according to claim 1, wherein the series comprises at least 8 and at most 2000 cycles.

6. A method according to claim 1, wherein the duration of each denaturing step is at least 1 millisecond and at most 1 hour, and the duration of each renaturing step is at least 1 second and at most 12 hours.

7. A method according to claim 6, wherein the denaturing conditions of each individual denaturing step are kept substantially constant for a period of time, and the renaturing conditions of each individual renaturing step are kept substantially constant for a period of time, the periods of time during which conditions are kept substantially constant being separated by transition periods during which the conditions are changed.

8. A method according to claim 7, in which the transition period between steps for which conditions are kept substantially constant has a duration between 0.1 second and 12 hours.

9. A method according to claim 8, wherein the period of time for which the denaturing conditions of the denaturing step are kept substantially constant has a duration of between 1 and 10 minutes, and the period of time for which the renaturing conditions of the renaturing step are kept substantially constant has a duration of between 1 and 45 minutes.

10. A method according to claim 1, wherein the polypeptide molecules are in contact with a liquid phase during the denaturing and renaturing steps, the liquid phase being an aqueous phase or an organic phase.

11. A method according to claim 10, wherein the polypeptide molecules are substantially confined to an environment which allows changing or exchanging the liquid phase substantially without entraining the polypeptide molecules.

12. A method according to claim 11, wherein the polypeptides are confined to a dialysis device or a liquid two-phase system.

13. A method according to claim 11, wherein the polypeptide molecules are bound to a solid or semisolid carrier.

14. A method according to claim 1, wherein the polypeptide molecules comprise a polypeptide segment which is a substrate for preferential cleavage by a cleaving agent at a specific peptide bond.

15. A method according to claim 14, wherein polypeptide segment is one which is a substrate for cleavage at a specific peptide bond by a cleaving agent selected from the group consisting of cyanogen bromide, hydroxylamine, iodosobenzoic acid, N-bromosuccinimide, and an enzyme.

16. A method according to claim 1, wherein the polypeptide molecules comprise a polypeptide segment which is in vitro-convertible into a derivatized polypeptide segment which is a substrate for preferential cleavage by a cleaving agent at a specific peptide bond.

17. A method according to claim 16, wherein the in vitro-convertible polypeptide segment is convertible into a derivatized polypeptide segment which is selectively recognized by the bovine coagulation factor $X_a$.

18. A method according to claim 7, wherein the change of conditions during the transition period is accomplished by changing the chemical composition of a liquid phase with which the polypeptide molecules are in contact.

19. A method according to claim 18, wherein denaturing of the polypeptide molecules is accomplished by contacting the polypeptide molecules with a liquid phase in which at least one denaturing compound is dissolved, and wherein renaturing of the polypeptide molecules is accomplished by contacting the polypeptide molecules with a liquid phase which either contains at least one dissolved denaturing compound in such a concentration that the contact with the liquid phase will tend to renature rather than denature the ensemble of polypeptide molecules in their respective conformational states resulting from the preceding step, or contains no denaturing compound.

20. A method according to claim 19, wherein the denaturing compound is selected from urea, guanidine-HCl, and di-$C_{1-6}$alkylformamide.

21. A method according to claim 3, wherein the polypeptide molecules are in contact with a liquid phase during the denaturing step and the renaturing step, the liquid phase being an aqueous phase or an organic phase and wherein the liquid phase used in at least one of the denaturing steps and/or in at least one of the renaturing steps contains at least one disulphide-reshuffling system, X.

22. A method according to claim 21, wherein the at least one disulphide-reshuffling system X is one which is capable of reducing or reshuffling incorrectly formed disulphide bridges under conditions with respect to concentration of the denaturing agent at which unfolded or misfolded proteins are denatured and at which there is substantially no reduction or reshuffling or correctly formed disulphide bridges.

23. A method according to claim 21, wherein the presence of the disulphide reshuffling system X in at least one step results in a ratio between the relative amount of reduced/reshuffled initially incorrectly formed disulphide bridges and the relative amount of reduced/reshuffled initially correctly formed disulphide bridges of at least 1.05.

24. A method according to claim 22 wherein the disulphide-reshuffling system contains glutathione, 2-mercaptoethanol or thiocholine, each of which in admixture with its corresponding symmetrical disulphide.

25. A method according to claim 21, wherein substantially all cysteine residues in the polypeptide molecules have been converted to mixed disulphide products of either glutathione, thiocholine, mercaptoethanol or mercaptoacetic acid, during at least one of the cycles.

26. A method according to claim 10, wherein the polarity of the liquid phase used in the renaturing of the polypeptide molecules has been modified by the addition of a salt, a polymer, a hydrofluoro compound or a combination thereof.

27. A method according to claim 1, wherein the denaturing and renaturing of the polypeptide molecules is accomplished by direct changes in physical parameters to which the polypeptide molecules are exposed or by changes in physical parameters which enhance or moderate the denaturing and renaturing conditions.

28. A method according to claim 14, wherein the polypeptide segment which directs preferential cleavage is selected from the group consisting of SEQ ID No: 43, SEQ ID NO: 44, SEQ ID NO: 45, and SEQ ID NO: 46, is linked N-terminally to the authentic polypeptide, and is selectively recognized by the bovine coagulation factor $X_a$, and wherein the chemical changes in the liquid phase are accomplished by changing between a denaturing solution B comprising at least one denaturing compound and a renaturing solution A.

29. A method according to claim 27, wherein the denaturing or unfolding influence is one or more denaturing compounds and the concentration of said compounds is adjusted after each cycle.

30. A method according to claim 1 in which the polypeptide molecules of the ensemble have a length of at least 25 amino acid residues and at most 5000 amino acid residues.

31. A method according to claim 1, wherein the polypeptides of the initial ensemble are artificial polypeptides produced in prokaryotic cells by means of recombinant DNA-techniques.

32. A method according to claim 13, wherein the solid or semisolid carrier is selected from the group consisting of a filter surface; a hollow fibre; a beaded chromatographic medium which is selected from an agarose gel, a polyacrylamide gel, a fibrous cellulose matrix, an HPLC matrix, and an FPLC matrix; a substance having molecules of such a size that the molecules with the polypeptide molecules bound thereto, when dissolved or dispersed in a liquid phase, can be retained by means of a filter; a substance capable of forming micelles or participating in the formation of micelles under the conditions in which the method is performed, allowing the liquid phase to be changed or exchanged substantially without entraining the micelles; and a water-soluble polymer.

33. A method according to claim 15, wherein the enzyme is selected from the group consisting of bovine coagulation factor $X_a$ and bovine enterokinase.

34. A method according to claim 27, wherein the physical parameters are temperature or pressure.

35. The method according to claim 34, wherein the polypeptide molecules are in contact with a liquid phase during the denaturing and renaturing steps, the liquid phase being an aqueous phase or an organic phase.

36. A method according to claim 1, wherein the series comprises at least 5 cycles.

37. A method according to claim 4, wherein the amino acid sequence corresponding to that of an authentic polypeptide is joined to the additional polypeptide segment or segments via a cleavable junction or similar or dissimilar cleavable junctions.

38. A method according to claim 13, wherein the polypeptide molecules are non-covalently adsorbed to the carrier through a moiety having affinity to a component of the carrier.

39. A method according to claim 38, wherein the moiety has an amino acid sequence identical to SEQ ID NO: 47, the carrier comprising a Nitrilotriacetic Acid derivative (NTA) charged with $Ni^{++}$ ions.

40. A method according to claim 14, wherein the polypeptide segment which directs preferential cleavage is a sequence which is selectively recognized by the bovine coagulation factor $X_a$.

41. A method according to claim 17, wherein the in vitro-convertible polypeptide segment has an amino acid sequence selected from the group consisting of SEQ ID NO: 43, SEQ ID NO: 44, SEQ ID NO: 45 and SEQ ID NO: 46.

42. A method according to claim 41, wherein the polypeptide molecules comprise a polypeptide segment with either a) the amino acid sequence SEQ ID NO: 43 or SEQ ID NO: 44, which is converted into a derivatized polypeptide, which is selectively recognized by bovine coagulation factor $X_a$, by reacting the cysteine residue of SEQ ID NO: 43 or SEQ ID NO: 44 with N-(2-mercaptoethyl) morpholyl-2-thiopyridyl disulphide or mercaptothioacetate-2-thiopyridyl disulphide, or b) with the amino acid sequence SEQ ID NO: 45 or SEQ ID NO: 46, which is converted into a derivatized polypeptide, which is selectively recognized by bovine coagulation factor $X_a$, by oxidation of the thioether moiety in the methionine side group of SEQ ID NO: 45 or SEQ ID NO: 46 to a sulphoxide or sulphone derivative.

43. A method according to claim 40, wherein the polypeptide segment selected from the group consisting of SEQ ID NO: 38, SEQ ID NO: 40, SEQ ID NO: 41 and SEQ ID NO: 42 is linked N-terminally to the authentic polypeptide.

44. A method according to claim 40, wherein the polypeptide segment selected from the group consisting of SEQ ID NO: 43, SEQ ID NO: 44, SEQ ID NO: 45 and SEQ ID NO: 46 is linked N-terminally to the authentic polypeptide.

45. A method according to claim 18, wherein the denaturing of the polypeptide molecules is achieved or enhanced by decreasing or increasing the pH of the liquid phase.

46. A method according to claim 24, wherein the conversion of the cysteine residues to mixed disulphide products is accomplished by reacting the fully denatured and fully reduced ensemble of polypeptide molecules with an excess of a reagent which is a high-energy mixed disulphide compound.

47. A method according to claim 46, wherein the high-energy mixed disulphide compound is aliphatic-aromatic.

48. A method according to claim 46, wherein the high-energy mixed disulphide compound has the general formula:

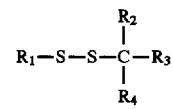

wherein $R_1$ is 2-pyridyl, and $R_2$, $R_3$ and $R_4$ are hydrogen or an optionally substituted lower aromatic or aliphatic hydrocarbon group.

49. A method according to claim 47, wherein the high-energy mixed disulphide compound is selected from the group consisting of glutathionyl-2-thiopyridyl disulphide, 2-thiocholyl-2-thiopyridyl disulphide, 2-mercaptoethanol-2-thiopyridyl disulphide and mercaptoacetate-2-thiopyridyl disulphide.

50. A method according to claim 28, wherein the concentration of one or more denaturing compounds in denaturing solution B is decremented after each cycle.

51. A method according to claim 27, wherein the concentration of one or more denaturing compounds in denaturing solution B is kept constant in each cycle.

52. A method according to claim 5, wherein the series comprises at least 10 and at most 1000 cycles.

53. A method according to claim 52, wherein the series comprises at least 25 cycles and at most 500 cycles.

54. A method according to claim 53, wherein the series comprises at most 200 cycles.

55. A method according to claim 54, wherein the series comprises at most 100 cycles.

56. A method according to claim 55, wherein the series comprises at most 50 cycles.

57. A method according to claim 38, wherein the moiety having affinity to a component of the carrier is a biotin group or an analogue thereof bound to an amino acid moiety of the polypeptide, the carrier having avidin, streptavidin or analogues thereof attached thereto.

58. A method according to claim 40, wherein the polypeptide segment has an amino acid sequence selected from the group consisting of SEQ ID NO: 38, SEQ ID NO: 40, SEQ ID NO: 41 and SEQ ID NO: 42.

59. A method according to claim 20, wherein the di-$C_{1-6}$-alkyl-formamide is dimethylformamide or di-$C_{1-6}$-alkylsulphone.

60. A method according to claim 26, wherein the hydrofluoro compound is trifluoroethanol.

* * * * *

SEQUENCE LISTING ( 1 ) GENERAL INFORMATION:

( i i i ) NUMBER OF SEQUENCES: 58

( 2 ) INFORMATION FOR SEQ ID NO: 1:

( i ) SEQUENCE CHARACTERISTICS:
        ( A ) LENGTH: 1554 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: YES ( i i i ) ANTI-SENSE: NO ( v i ) ORIGINAL SOURCE:
        ( A ) ORGANISM: Bos taurus ( i x ) FEATURE:
        ( A ) NAME/KEY: CDS
        ( B ) LOCATION: 76..1551

( x i ) SEQUENCE DESCRIPTION: SEQ ID NO: 1:

```
AGCCTGGGCG  AGCGGACCTT  GCCCTGGAGG  CCTGTTGCGG  CAGGGACTCA  CGGCTGTCCT      60

CGGAAGGGCC  CCACC ATG GCG GGC CTG CTG CAT CTC GTT CTG CTC AGC ACC         111
            Met Ala Gly Leu Leu His Leu Val Leu Leu Ser Thr
              1               5                  10

GCC CTG GGC GGC CTC CTG CGG CCG GCG GGG AGC GTG TTC CTG CCC CGG           159
Ala Leu Gly Gly Leu Leu Arg Pro Ala Gly Ser Val Phe Leu Pro Arg
         15                  20                  25

GAC CAG GCC CAC CGT GTC CTG CAG AGA GCC CGC AGG GCC AAC TCA TTC           207
Asp Gln Ala His Arg Val Leu Gln Arg Ala Arg Arg Ala Asn Ser Phe
     30                  35                  40

TTG GAG GAG GTG AAG CAG GGA AAC CTG GAG CGA GAG TGC CTG GAG GAG           255
Leu Glu Glu Val Lys Gln Gly Asn Leu Glu Arg Glu Cys Leu Glu Glu
 45                  50                  55                  60
```

| | | | | | | | | | | | | | | | | |
|---|---|---|---|---|---|---|---|---|---|---|---|---|---|---|---|---|
| GCC | TGC | TCA | CTA | GAG | GAG | GCC | CGC | GAG | GTC | TTC | GAG | GAC | GCA | GAG | CAG | 303 |
| Ala | Cys | Ser | Leu | Glu 65 | Glu | Ala | Arg | Glu | Val 70 | Phe | Glu | Asp | Ala | Glu 75 | Gln | |
| ACG | GAT | GAA | TTC | TGG | AGT | AAA | TAC | AAA | GAT | GGA | GAC | CAG | TGT | GAA | GGC | 351 |
| Thr | Asp | Glu | Phe 80 | Trp | Ser | Lys | Tyr | Lys 85 | Asp | Gly | Asp | Gln | Cys 90 | Glu | Gly | |
| CAC | CCG | TGC | CTG | AAT | CAG | GGC | CAC | TGT | AAA | GAC | GGC | ATC | GGA | GAC | TAC | 399 |
| His | Pro | Cys 95 | Leu | Asn | Gln | Gly | His 100 | Cys | Lys | Asp | Gly | Ile 105 | Gly | Asp | Tyr | |
| ACC | TGC | ACC | TGT | GCG | GAA | GGG | TTT | GAA | GGC | AAA | AAC | TGC | GAG | TTC | TCC | 447 |
| Thr | Cys | Thr 110 | Cys | Ala | Glu | Gly 115 | Phe | Glu | Gly | Lys | Asn 120 | Cys | Glu | Phe | Ser | |
| ACG | CGT | GAG | ATC | TGC | AGC | CTG | GAC | AAT | GGA | GGC | TGC | GAC | CAG | TTC | TGC | 495 |
| Thr 125 | Arg | Glu | Ile | Cys | Ser 130 | Leu | Asp | Asn | Gly | Gly 135 | Cys | Asp | Gln | Phe | Cys 140 | |
| AGG | GAG | GAG | CGC | AGC | GAG | GTG | CGG | TGC | TCC | TGC | GCG | CAC | GGC | TAC | GTG | 543 |
| Arg | Glu | Glu | Arg | Ser 145 | Glu | Val | Arg | Cys | Ser 150 | Cys | Ala | His | Gly | Tyr 155 | Val | |
| CTG | GGC | GAC | GAC | AGC | AAG | TCC | TGC | GTG | TCC | ACA | GAG | CGC | TTC | CCC | TGT | 591 |
| Leu | Gly | Asp | Asp 160 | Ser | Lys | Ser | Cys | Val 165 | Ser | Thr | Glu | Arg | Phe 170 | Pro | Cys | |
| GGG | AAG | TTC | ACG | CAG | GGA | CGC | AGC | CGG | CGG | TGG | GCC | ATC | CAC | ACC | AGC | 639 |
| Gly | Lys | Phe 175 | Thr | Gln | Gly | Arg | Ser 180 | Arg | Arg | Trp | Ala | Ile 185 | His | Thr | Ser | |
| GAG | GAC | GCG | CTT | GAC | GCC | AGC | GAG | CTG | GAG | CAC | TAC | GAC | CCT | GCA | GAC | 687 |
| Glu | Asp 190 | Ala | Leu | Asp | Ala | Ser 195 | Glu | Leu | Glu | His | Tyr 200 | Asp | Pro | Ala | Asp | |
| CTG | AGC | CCC | ACA | GAG | AGC | TCC | TTG | GAC | CTG | CTG | GGC | CTC | AAC | AGG | ACC | 735 |
| Leu 205 | Ser | Pro | Thr | Glu | Ser 210 | Ser | Leu | Asp | Leu | Leu 215 | Gly | Leu | Asn | Arg | Thr 220 | |
| GAG | CCC | AGC | GCC | GGG | GAG | GAC | GGC | AGC | CAG | GTG | GTC | CGG | ATA | GTG | GGC | 783 |
| Glu | Pro | Ser | Ala | Gly 225 | Glu | Asp | Gly | Ser | Gln 230 | Val | Val | Arg | Ile | Val 235 | Gly | |
| GGC | AGG | GAC | TGC | GCG | GAG | GGC | GAG | TGC | CCA | TGG | CAG | GCT | CTG | CTG | GTC | 831 |
| Gly | Arg | Asp | Cys 240 | Ala | Glu | Gly | Glu | Cys 245 | Pro | Trp | Gln | Ala | Leu 250 | Leu | Val | |
| AAC | GAA | GAG | AAC | GAG | GGA | TTC | TGC | GGG | GGC | ACC | ATC | CTG | AAC | GAG | TTC | 879 |
| Asn | Glu | Glu 255 | Asn | Glu | Gly | Phe | Cys 260 | Gly | Gly | Thr | Ile | Leu 265 | Asn | Glu | Phe | |
| TAC | GTC | CTC | ACG | GCT | GCC | CAC | TGC | CTG | CAC | CAG | GCC | AAG | AGG | TTC | ACG | 927 |
| Tyr | Val 270 | Leu | Thr | Ala | Ala | His 275 | Cys | Leu | His | Gln | Ala 280 | Lys | Arg | Phe | Thr | |
| GTG | AGG | GTC | GGC | GAC | CGG | AAC | ACA | GAG | CAG | GAG | GAG | GGC | AAC | GAG | ATG | 975 |
| Val 285 | Arg | Val | Gly | Asp | Arg 290 | Asn | Thr | Glu | Gln | Glu 295 | Glu | Gly | Asn | Glu | Met 300 | |
| GCA | CAC | GAG | GTG | GAG | ATG | ACT | GTG | AAG | CAC | AGC | CGC | TTT | GTC | AAG | GAG | 1023 |
| Ala | His | Glu | Val | Glu 305 | Met | Thr | Val | Lys | His 310 | Ser | Arg | Phe | Val | Lys 315 | Glu | |
| ACC | TAC | GAC | TTC | GAC | ATC | GCG | GTG | CTG | AGG | CTC | AAG | ACG | CCC | ATC | CGG | 1071 |
| Thr | Tyr | Asp | Phe | Asp 320 | Ile | Ala | Val | Leu | Arg 325 | Leu | Lys | Thr | Pro | Ile 330 | Arg | |
| TTC | CGC | CGG | AAC | GTG | GCG | CCC | GCC | TGC | CTG | CCC | GAG | AAG | GAC | TGG | GCG | 1119 |
| Phe | Arg | Arg | Asn 335 | Val | Ala | Pro | Ala | Cys 340 | Leu | Pro | Glu | Lys | Asp 345 | Trp | Ala | |
| GAG | GCC | ACG | CTG | ATG | ACC | CAG | AAG | ACG | GGC | ATC | GTC | AGC | GGC | TTC | GGG | 1167 |
| Glu | Ala | Thr 350 | Leu | Met | Thr | Gln | Lys 355 | Thr | Gly | Ile | Val | Ser 360 | Gly | Phe | Gly | |
| CGC | ACG | CAC | GAG | AAG | GGC | CGC | CTG | TCG | TCC | ACG | CTC | AAG | ATG | CTG | GAG | 1215 |
| Arg | Thr | His 365 | Glu | Lys | Gly | Arg | Leu 370 | Ser | Ser | Thr | Leu | Lys 375 | Met | Leu | Glu 380 | |

```
GTG  CCC  TAC  GTG  GAC  CGC  AGC  ACC  TGT  AAG  CTG  TCC  AGC  AGC  TTC  ACC    1263
Val  Pro  Tyr  Val  Asp  Arg  Ser  Thr  Cys  Lys  Leu  Ser  Ser  Ser  Phe  Thr
               385                      390                      395

ATT  ACG  CCC  AAC  ATG  TTC  TGC  GCC  GGC  TAC  GAC  ACC  CAG  CCC  GAG  GAC    1311
Ile  Thr  Pro  Asn  Met  Phe  Cys  Ala  Gly  Tyr  Asp  Thr  Gln  Pro  Glu  Asp
                    400                      405                      410

GCC  TGC  CAG  GGC  GAC  AGT  GGC  GGC  CCC  CAC  GTC  ACC  CGC  TTC  AAG  GAC    1359
Ala  Cys  Gln  Gly  Asp  Ser  Gly  Gly  Pro  His  Val  Thr  Arg  Phe  Lys  Asp
          415                      420                      425

ACC  TAC  TTC  GTC  ACA  GGC  ATC  GTC  AGC  TGG  GGA  GAA  GGG  TGC  GCG  CGC    1407
Thr  Tyr  Phe  Val  Thr  Gly  Ile  Val  Ser  Trp  Gly  Glu  Gly  Cys  Ala  Arg
               430                      435                      440

AAG  GGC  AAG  TTC  GGC  GTC  TAC  ACC  AAG  GTC  TCC  AAC  TTC  CTC  AAG  TGG    1455
Lys  Gly  Lys  Phe  Gly  Val  Tyr  Thr  Lys  Val  Ser  Asn  Phe  Leu  Lys  Trp
445                      450                      455                      460

ATC  GAC  AAG  ATC  ATG  AAG  GCC  AGG  GCA  GGG  GCC  GCG  GGC  AGC  CGC  GGC    1503
Ile  Asp  Lys  Ile  Met  Lys  Ala  Arg  Ala  Gly  Ala  Ala  Gly  Ser  Arg  Gly
                    465                      470                      475

CAC  AGT  GAA  GCC  CCT  GCC  ACC  TGG  ACG  GTC  CCG  CCG  CCC  CTC  CCC  CTC    1551
His  Ser  Glu  Ala  Pro  Ala  Thr  Trp  Thr  Val  Pro  Pro  Pro  Leu  Pro  Leu
               480                      485                      490

TAA                                                                                1554
```

( 2 ) INFORMATION FOR SEQ ID NO: 2:

( i ) SEQUENCE CHARACTERISTICS:
        ( A ) LENGTH: 492 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO: 2:

```
Met  Ala  Gly  Leu  Leu  His  Leu  Val  Leu  Leu  Ser  Thr  Ala  Leu  Gly  Gly
 1                   5                        10                       15

Leu  Leu  Arg  Pro  Ala  Gly  Ser  Val  Phe  Leu  Pro  Arg  Asp  Gln  Ala  His
               20                       25                       30

Arg  Val  Leu  Gln  Arg  Ala  Arg  Arg  Ala  Asn  Ser  Phe  Leu  Glu  Glu  Val
          35                       40                       45

Lys  Gln  Gly  Asn  Leu  Glu  Arg  Glu  Cys  Leu  Glu  Glu  Ala  Cys  Ser  Leu
     50                       55                       60

Glu  Glu  Ala  Arg  Glu  Val  Phe  Glu  Asp  Ala  Glu  Gln  Thr  Asp  Glu  Phe
65                       70                       75                       80

Trp  Ser  Lys  Tyr  Lys  Asp  Gly  Asp  Gln  Cys  Glu  Gly  His  Pro  Cys  Leu
                    85                       90                       95

Asn  Gln  Gly  His  Cys  Lys  Asp  Gly  Ile  Gly  Asp  Tyr  Thr  Cys  Thr  Cys
               100                      105                      110

Ala  Glu  Gly  Phe  Glu  Gly  Lys  Asn  Cys  Glu  Phe  Ser  Thr  Arg  Glu  Ile
          115                      120                      125

Cys  Ser  Leu  Asp  Asn  Gly  Gly  Cys  Asp  Gln  Phe  Cys  Arg  Glu  Glu  Arg
     130                      135                      140

Ser  Glu  Val  Arg  Cys  Ser  Cys  Ala  His  Gly  Tyr  Val  Leu  Gly  Asp  Asp
145                      150                      155                      160

Ser  Lys  Ser  Cys  Val  Ser  Thr  Glu  Arg  Phe  Pro  Cys  Gly  Lys  Phe  Thr
                    165                      170                      175

Gln  Gly  Arg  Ser  Arg  Arg  Trp  Ala  Ile  His  Thr  Ser  Glu  Asp  Ala  Leu
               180                      185                      190

Asp  Ala  Ser  Glu  Leu  Glu  His  Tyr  Asp  Pro  Ala  Asp  Leu  Ser  Pro  Thr
```

|     |     |     |     |     | 195 |     |     |     |     | 200 |     |     |     |     | 205 |     |     |
|-----|-----|-----|-----|-----|-----|-----|-----|-----|-----|-----|-----|-----|-----|-----|-----|-----|-----|

Glu Ser Ser Leu Asp Leu Leu Gly Leu Asn Arg Thr Glu Pro Ser Ala
210                         215                     220

Gly Glu Asp Gly Ser Gln Val Val Arg Ile Val Gly Gly Arg Asp Cys
225                 230                 235                 240

Ala Glu Gly Glu Cys Pro Trp Gln Ala Leu Leu Val Asn Glu Glu Asn
                245                 250                 255

Glu Gly Phe Cys Gly Gly Thr Ile Leu Asn Glu Phe Tyr Val Leu Thr
            260                 265                 270

Ala Ala His Cys Leu His Gln Ala Lys Arg Phe Thr Val Arg Val Gly
        275                 280                 285

Asp Arg Asn Thr Glu Gln Glu Gly Asn Glu Met Ala His Glu Val
    290                 295                 300

Glu Met Thr Val Lys His Ser Arg Phe Val Lys Glu Thr Tyr Asp Phe
305                 310                 315                 320

Asp Ile Ala Val Leu Arg Leu Lys Thr Pro Ile Arg Phe Arg Arg Asn
                325                 330                 335

Val Ala Pro Ala Cys Leu Pro Glu Lys Asp Trp Ala Glu Ala Thr Leu
            340                 345                 350

Met Thr Gln Lys Thr Gly Ile Val Ser Gly Phe Gly Arg Thr His Glu
        355                 360                 365

Lys Gly Arg Leu Ser Ser Thr Leu Lys Met Leu Glu Val Pro Tyr Val
    370                 375                 380

Asp Arg Ser Thr Cys Lys Leu Ser Ser Ser Phe Thr Ile Thr Pro Asn
385                 390                 395                 400

Met Phe Cys Ala Gly Tyr Asp Thr Gln Pro Glu Asp Ala Cys Gln Gly
            405                 410                 415

Asp Ser Gly Gly Pro His Val Thr Arg Phe Lys Asp Thr Tyr Phe Val
        420                 425                 430

Thr Gly Ile Val Ser Trp Gly Glu Gly Cys Ala Arg Lys Gly Lys Phe
    435                 440                 445

Gly Val Tyr Thr Lys Val Ser Asn Phe Leu Lys Trp Ile Asp Lys Ile
450                 455                 460

Met Lys Ala Arg Ala Gly Ala Ala Gly Ser Arg Gly His Ser Glu Ala
465                 470                 475                 480

Pro Ala Thr Trp Thr Val Pro Pro Pro Leu Pro Leu
            485                 490

(2) INFORMATION FOR SEQ ID NO: 3:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 3:

CGTCCTGGAT CCATCGAGGG TAGAATCCAG CGTACTCCAA AG     42

(2) INFORMATION FOR SEQ ID NO: 4:

(i) SEQUENCE CHARACTERISTICS:
        (A) LENGTH: 23 base pairs
        (B) TYPE: nucleic acid
        (C) STRANDEDNESS: single
        (D) TOPOLOGY: linear

```
        ( i i ) MOLECULE TYPE: DNA (synthetic)

( x i ) SEQUENCE DESCRIPTION: SEQ ID NO: 4:

GCGAAGCTTG ATCACATGTC TCG                                              23

( 2 ) INFORMATION FOR SEQ ID NO: 5:

( i ) SEQUENCE CHARACTERISTICS:
                ( A ) LENGTH: 44 base pairs
                ( B ) TYPE: nucleic acid
                ( C ) STRANDEDNESS: single
                ( D ) TOPOLOGY: linear ( i i ) MOLECULE TYPE: DNA (synthetic)

( x i ) SEQUENCE DESCRIPTION: SEQ ID NO: 5:

CGTCCTGGAT CCATCGAGGG TAGAATCCAG AAAACCCCTC AAAT                       44

( 2 ) INFORMATION FOR SEQ ID NO: 6:

( i ) SEQUENCE CHARACTERISTICS:
                ( A ) LENGTH: 22 base pairs
                ( B ) TYPE: nucleic acid
                ( C ) STRANDEDNESS: single
                ( D ) TOPOLOGY: linear ( i i ) MOLECULE TYPE: DNA (synthetic)

( x i ) SEQUENCE DESCRIPTION: SEQ ID NO: 6:

GCGAAGCTTA CATGTCTCGA TC                                               22

( 2 ) INFORMATION FOR SEQ ID NO: 7:

( i ) SEQUENCE CHARACTERISTICS:
                ( A ) LENGTH: 40 base pairs
                ( B ) TYPE: nucleic acid
                ( C ) STRANDEDNESS: single
                ( D ) TOPOLOGY: linear ( i i ) MOLECULE TYPE: DNA (synthetic)

( x i ) SEQUENCE DESCRIPTION: SEQ ID NO: 7:

CCTGGATCCA TCGAGGGTAG GTTCCCAACC ATTCCCTTAT                            40

( 2 ) INFORMATION FOR SEQ ID NO: 8:

( i ) SEQUENCE CHARACTERISTICS:
                ( A ) LENGTH: 26 base pairs
                ( B ) TYPE: nucleic acid
                ( C ) STRANDEDNESS: single
                ( D ) TOPOLOGY: linear ( i i ) MOLECULE TYPE: DNA (synthetic)

( x i ) SEQUENCE DESCRIPTION: SEQ ID NO: 8:

CCGAAGCTTA GAAGCCACAG CTGCCC                                           26

( 2 ) INFORMATION FOR SEQ ID NO: 9:

( i ) SEQUENCE CHARACTERISTICS:
                ( A ) LENGTH: 39 base pairs
                ( B ) TYPE: nucleic acid
                ( C ) STRANDEDNESS: single
                ( D ) TOPOLOGY: linear ( i i ) MOLECULE TYPE: DNA (synthetic)

( x i ) SEQUENCE DESCRIPTION: SEQ ID NO: 9:

CGTCCTGGAT CCATCGAGGG TAGGTACTCG CGGGAGAAG                             39
```

( 2 ) INFORMATION FOR SEQ ID NO: 10:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 10:

CGACCGAAGC TTCAGAGTTC GTTGTG                                    26

( 2 ) INFORMATION FOR SEQ ID NO: 11:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 11:

CGTCCTGGAT CCATCGAGGG TAGGGCTATC GACGCCCTA AG                 42

( 2 ) INFORMATION FOR SEQ ID NO: 12:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 12:

CGACCGAAGC TTATCGGCAG TGGGGCCCCT                                30

( 2 ) INFORMATION FOR SEQ ID NO: 13:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 13:

CGACCGAAGC TTAGGCCTTG CAGGAGCGG                                29

( 2 ) INFORMATION FOR SEQ ID NO: 14:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 14:

CGACCGAAGC TTACTTCTTG CATGACTTCC CG                           32

( 2 ) INFORMATION FOR SEQ ID NO: 15:

( i ) SEQUENCE CHARACTERISTICS:

5,739,281

(A) LENGTH: 42 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 15:

CGTCCTGGAT CCATCGAGGG TAGGGGCACC AACAAATGCC GG    42

(2) INFORMATION FOR SEQ ID NO: 16:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 16:

CGACCGAAGC TTAGTCCAGG CTGCGGCAG    29

(2) INFORMATION FOR SEQ ID NO: 17:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 17:

CGTCCTGGAT CCATCGAGGG TAGGGTGCCT CCACCCCAGT G    41

(2) INFORMATION FOR SEQ ID NO: 18:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 18:

CGACCGAAGC TTACTGGTCG CAGAGCTCG    29

(2) INFORMATION FOR SEQ ID NO: 19:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO: 19:

CCTTGATCAA TCGAGGGTAG GGGTGGTCAG TGCTCTCTGA ATAACG    46

(2) INFORMATION FOR SEQ ID NO: 20:

(i) SEQUENCE CHARACTERISTICS:
(A) LENGTH: 29 base pairs
(B) TYPE: nucleic acid
(C) STRANDEDNESS: single
(D) TOPOLOGY: linear ( i i ) MOLECULE TYPE: DNA (synthetic)

( x i ) SEQUENCE DESCRIPTION: SEQ ID NO: 20:

CGCAAGCTTA CTTAAACTCA TAGCAGGTG 29

( 2 ) INFORMATION FOR SEQ ID NO: 21:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 21:

CGTCCTGGAT CCATCGAGGG TAGGGCGGTG AATTCCTCTT GCCG 44

( 2 ) INFORMATION FOR SEQ ID NO: 22:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 22:

CGACCGAAGC TTAGATGTGG CAGCCACGCT 30

( 2 ) INFORMATION FOR SEQ ID NO: 23:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 23:

CGTCCTGGAT CCATCGAGGG TAGGGTGTCC AACTGCACGG CT 42

( 2 ) INFORMATION FOR SEQ ID NO: 24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 24:

CGACCGAAGC TTAGATGCTG CAGTCCTCCT 30

( 2 ) INFORMATION FOR SEQ ID NO: 25:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO: 25:

CGTCCTGGAT CCATCGAGGG TAGGAGTAAA TACAAAGATG GAGACCA 47

( 2 ) INFORMATION FOR SEQ ID NO: 26:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO: 26:

```
CGACCGAAGC TTACCAGGTG GCAGGGGCTT                                30
```

( 2 ) INFORMATION FOR SEQ ID NO: 27:

( i ) SEQUENCE CHARACTERISTICS:
    ( A ) LENGTH: 62 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO: 27:

```
CTGCCTGGAT CCATCGAGGG TAGGAAAGTG TATCTCTCAT CAGAGTGCAA GACTGGGAAT GG    62
```

( 2 ) INFORMATION FOR SEQ ID NO: 28:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO: 28:

```
CGACCGAAGC TTATTCACAC TCAAGAATGT CGC                            33
```

( 2 ) INFORMATION FOR SEQ ID NO: 29:

( i ) SEQUENCE CHARACTERISTICS:
    ( A ) LENGTH: 42 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO: 29:

```
CTGCCTGGAT CCATCGAGGG TAGGGTCCAG GACTGCTACC AT                  42
```

( 2 ) INFORMATION FOR SEQ ID NO: 30:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO: 30:

```
CGACCGAAGC TTACGCTTCT GTTCCTGAGC A                              31
```

( 2 ) INFORMATION FOR SEQ ID NO: 31:

( i ) SEQUENCE CHARACTERISTICS:

(A) LENGTH: 40 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 31:

CCTGGATCCA TCGAGGGTAG GGTCTACCTC CAGACATCCT  40

(2) INFORMATION FOR SEQ ID NO: 32:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 32:

CCGAAGCTTC AAGCATTTCC AAGATC  26

(2) INFORMATION FOR SEQ ID NO: 33:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 33:

CCTGGATCCA TCGAGGGTAG GGGCGAGCCA CCAACCCAG  39

(2) INFORMATION FOR SEQ ID NO: 34:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 34:

CCGAAGCTTA CACGATCCCG AACTG  25

(2) INFORMATION FOR SEQ ID NO: 35:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO: 35:

CCGAGATCTA TCGAGGGTAG GCAGGTCAAA CTGCAGCA  38

(2) INFORMATION FOR SEQ ID NO: 36:

(i) SEQUENCE CHARACTERISTICS:
        (A) LENGTH: 29 base pairs
        (B) TYPE: nucleic acid
        (C) STRANDEDNESS: single
        (D) TOPOLOGY: linear ( i i ) MOLECULE TYPE: DNA (synthetic)

( x i ) SEQUENCE DESCRIPTION: SEQ ID NO: 36:

GCCAAGCTTA ATTCAGATCC TCTTCTGAG                                    29

( 2 ) INFORMATION FOR SEQ ID NO: 37:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 37:

Gly Ser Ile Glu Gly Arg
1               5

( 2 ) INFORMATION FOR SEQ ID NO: 38:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 38:

Ile Glu Gly Arg
1

( 2 ) INFORMATION FOR SEQ ID NO: 39:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 39:

Tyr Trp Thr Asp
1

( 2 ) INFORMATION FOR SEQ ID NO: 40:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 40:

Ile Gln Gly Arg
1

( 2' ) INFORMATION FOR SEQ ID NO: 41:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 41:

Ala Glu Gly Arg
1

( 2 ) INFORMATION FOR SEQ ID NO: 42:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO: 42:

Ala Gln Gly Arg
1

( 2 ) INFORMATION FOR SEQ ID NO: 43:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO: 43:

Ile Cys Gly Arg
1

( 2 ) INFORMATION FOR SEQ ID NO: 44:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO: 44:

Ala Cys Gly Arg
1

( 2 ) INFORMATION FOR SEQ ID NO: 45:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO: 45:

Ile Met Gly Arg
1

( 2 ) INFORMATION FOR SEQ ID NO: 46:

( i ) SEQUENCE CHARACTERISTICS:
      ( A ) LENGTH: 4 amino acids
      ( B ) TYPE: amino acid
      ( C ) STRANDEDNESS:
      ( D ) TOPOLOGY: linear ( i i ) MOLECULE TYPE: peptide ( x i ) SEQUENCE DESCRIPTION: SEQ ID NO: 46:

Ala Met Gly Arg
1

( 2 ) INFORMATION FOR SEQ ID NO: 47:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 47:

His His His His His His
1                 5

( 2 ) INFORMATION FOR SEQ ID NO: 48:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 48:

Met Gly Ser His His His His His His Gly Ser Ile Glu Gly Arg
1               5                   10                  15

( 2 ) INFORMATION FOR SEQ ID NO: 49:

( i ) SEQUENCE CHARACTERISTICS:
        ( A ) LENGTH: 119 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO: 49:

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
                20                  25                  30

His Pro Ala Glu Asn Gly Lys Ser Asn Phe Leu Asn Cys Tyr Val Ser
            35                  40                  45

Gly Phe His Pro Ser Asp Ile Glu Val Asp Leu Leu Lys Asn Gly Glu
        50                  55                  60

Arg Ile Glu Lys Val Glu His Ser Asp Leu Ser Phe Ser Lys Asp Trp
65                  70                  75                  80

Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
            115

( 2 ) INFORMATION FOR SEQ ID NO: 50:

( i ) SEQUENCE CHARACTERISTICS:
        ( A ) LENGTH: 119 amino acids ( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO: 50:

| Met | Ala | Arg | Ser | Val | Thr | Leu | Val | Phe | Leu | Val | Leu | Val | Ser | Leu | Thr |
|---|---|---|---|---|---|---|---|---|---|---|---|---|---|---|---|
| 1 | | | | 5 | | | | | 10 | | | | | 15 | |

| Gly | Leu | Tyr | Ala | Ile | Gln | Lys | Thr | Pro | Gln | Ile | Gln | Val | Tyr | Ser | Arg |
|---|---|---|---|---|---|---|---|---|---|---|---|---|---|---|---|
| | | | 20 | | | | | 25 | | | | | 30 | | |

| His | Pro | Pro | Glu | Asn | Gly | Lys | Pro | Asn | Ile | Leu | Asn | Cys | Tyr | Val | Thr |
|---|---|---|---|---|---|---|---|---|---|---|---|---|---|---|---|
| | | 35 | | | | | 40 | | | | | 45 | | | |

| Gln | Phe | His | Pro | Pro | His | Ile | Glu | Ile | Gln | Met | Leu | Lys | Asn | Gly | Lys |
|---|---|---|---|---|---|---|---|---|---|---|---|---|---|---|---|
| | 50 | | | | | 55 | | | | | 60 | | | | |

| Lys | Ile | Pro | Lys | Val | Glu | Met | Ser | Asp | Met | Ser | Phe | Ser | Lys | Asp | Trp |
|---|---|---|---|---|---|---|---|---|---|---|---|---|---|---|---|
| 65 | | | | | 70 | | | | | 75 | | | | | 80 |

| Ser | Phe | Tyr | Ile | Leu | Ala | His | Thr | Glu | Phe | Thr | Pro | Thr | Glu | Thr | Asp |
|---|---|---|---|---|---|---|---|---|---|---|---|---|---|---|---|
| | | | | 85 | | | | | 90 | | | | | 95 | |

| Thr | Tyr | Ala | Cys | Arg | Val | Lys | His | Asp | Ser | Met | Ala | Glu | Pro | Lys | Thr |
|---|---|---|---|---|---|---|---|---|---|---|---|---|---|---|---|
| | | | 100 | | | | | 105 | | | | | 110 | | |

| Val | Tyr | Trp | Asp | Arg | Asp | Met |
|---|---|---|---|---|---|---|
| | | 115 | | | | |

( 2 ) INFORMATION FOR SEQ ID NO: 51:

( i ) SEQUENCE CHARACTERISTICS:
( A ) LENGTH: 217 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO: 51:

| Met | Ala | Thr | Gly | Ser | Arg | Thr | Ser | Leu | Leu | Leu | Ala | Phe | Gly | Leu | Leu |
|---|---|---|---|---|---|---|---|---|---|---|---|---|---|---|---|
| 1 | | | | 5 | | | | | 10 | | | | | 15 | |

| Cys | Leu | Pro | Trp | Leu | Gln | Glu | Gly | Ser | Ala | Phe | Pro | Thr | Ile | Pro | Leu |
|---|---|---|---|---|---|---|---|---|---|---|---|---|---|---|---|
| | | | 20 | | | | | 25 | | | | | 30 | | |

| Ser | Arg | Leu | Phe | Asp | Asn | Ala | Ser | Leu | Arg | Ala | His | Arg | Leu | His | Gln |
|---|---|---|---|---|---|---|---|---|---|---|---|---|---|---|---|
| | | 35 | | | | | 40 | | | | | 45 | | | |

| Leu | Ala | Phe | Asp | Thr | Tyr | Gln | Glu | Phe | Glu | Glu | Ala | Tyr | Ile | Pro | Lys |
|---|---|---|---|---|---|---|---|---|---|---|---|---|---|---|---|
| | 50 | | | | | 55 | | | | | 60 | | | | |

| Glu | Gln | Lys | Tyr | Ser | Phe | Leu | Gln | Asn | Pro | Gln | Thr | Ser | Leu | Cys | Phe |
|---|---|---|---|---|---|---|---|---|---|---|---|---|---|---|---|
| 65 | | | | | 70 | | | | | 75 | | | | | 80 |

| Ser | Glu | Ser | Ile | Pro | Thr | Pro | Ser | Asn | Arg | Glu | Glu | Thr | Gln | Gln | Lys |
|---|---|---|---|---|---|---|---|---|---|---|---|---|---|---|---|
| | | | | 85 | | | | | 90 | | | | | 95 | |

| Ser | Asn | Leu | Glu | Leu | Leu | Arg | Ile | Ser | Leu | Leu | Leu | Ile | Gln | Ser | Trp |
|---|---|---|---|---|---|---|---|---|---|---|---|---|---|---|---|
| | | | 100 | | | | | 105 | | | | | 110 | | |

| Leu | Glu | Pro | Val | Gln | Phe | Leu | Arg | Ser | Val | Phe | Ala | Asn | Ser | Leu | Val |
|---|---|---|---|---|---|---|---|---|---|---|---|---|---|---|---|
| | | 115 | | | | | 120 | | | | | 125 | | | |

| Tyr | Gly | Ala | Ser | Asp | Ser | Asn | Val | Tyr | Asp | Leu | Leu | Lys | Asp | Leu | Glu |
|---|---|---|---|---|---|---|---|---|---|---|---|---|---|---|---|
| | 130 | | | | | 135 | | | | | 140 | | | | |

| Glu | Gly | Ile | Gln | Thr | Leu | Met | Gly | Arg | Leu | Glu | Asp | Gly | Ser | Pro | Arg |
|---|---|---|---|---|---|---|---|---|---|---|---|---|---|---|---|
| 145 | | | | | 150 | | | | | 155 | | | | | 160 |

| Thr | Gly | Gln | Ile | Phe | Lys | Gln | Thr | Tyr | Ser | Lys | Phe | Asp | Thr | Asn | Ser |
|---|---|---|---|---|---|---|---|---|---|---|---|---|---|---|---|
| | | | | 165 | | | | | 170 | | | | | 175 | |

| His | Asn | Asp | Asp | Ala | Leu | Leu | Lys | Asn | Tyr | Gly | Leu | Leu | Tyr | Cys | Phe |
|---|---|---|---|---|---|---|---|---|---|---|---|---|---|---|---|
| | | | 180 | | | | | 185 | | | | | 190 | | |

```
Arg  Lys  Asp  Met  Asp  Lys  Val  Glu  Thr  Phe  Leu  Arg  Ile  Val  Gln  Cys
          195                 200                      205

Arg  Ser  Val  Glu  Gly  Ser  Cys  Gly  Phe
          210                 215
```

( 2 ) INFORMATION FOR SEQ ID NO: 52:

( i ) SEQUENCE CHARACTERISTICS:
( A ) LENGTH: 4544 amino acids
( B ) TYPE: amino acid
( C ) STRANDEDNESS:
( D ) TOPOLOGY: linear ( i i ) MOLECULE TYPE: protein ( x i ) SEQUENCE DESCRIPTION: SEQ ID NO: 52:

```
Met  Leu  Thr  Pro  Pro  Leu  Leu  Leu  Leu  Leu  Pro  Leu  Leu  Ser  Ala  Leu
 1                   5                    10                       15

Val  Ala  Ala  Ala  Ile  Asp  Ala  Pro  Lys  Thr  Cys  Ser  Pro  Lys  Gln  Phe
               20                  25                       30

Ala  Cys  Arg  Asp  Gln  Ile  Thr  Cys  Ile  Ser  Lys  Gly  Trp  Arg  Cys  Asp
          35                  40                  45

Gly  Glu  Arg  Asp  Cys  Pro  Asp  Gly  Ser  Asp  Glu  Ala  Pro  Glu  Ile  Cys
 50                       55                  60

Pro  Gln  Ser  Lys  Ala  Gln  Arg  Cys  Gln  Pro  Asn  Glu  His  Asn  Cys  Leu
 65                  70                       75                        80

Gly  Thr  Glu  Leu  Cys  Val  Pro  Met  Ser  Arg  Leu  Cys  Asn  Gly  Val  Gln
               85                       90                        95

Asp  Cys  Met  Asp  Gly  Ser  Asp  Glu  Gly  Pro  His  Cys  Arg  Glu  Leu  Gln
               100                 105                      110

Gly  Asn  Cys  Ser  Arg  Leu  Gly  Cys  Gln  His  His  Cys  Val  Pro  Thr  Leu
          115                 120                      125

Asp  Gly  Pro  Thr  Cys  Tyr  Cys  Asn  Ser  Ser  Phe  Gln  Leu  Gln  Ala  Asp
     130                 135                      140

Gly  Lys  Thr  Cys  Lys  Asp  Phe  Asp  Glu  Cys  Ser  Val  Tyr  Gly  Thr  Cys
145                      150                 155                       160

Ser  Gln  Leu  Cys  Thr  Asn  Thr  Asp  Gly  Ser  Phe  Ile  Cys  Gly  Cys  Val
               165                 170                       175

Glu  Gly  Tyr  Leu  Leu  Gln  Pro  Asp  Asn  Arg  Ser  Cys  Lys  Ala  Lys  Asn
               180                 185                      190

Glu  Pro  Val  Asp  Arg  Pro  Pro  Val  Leu  Leu  Ile  Ala  Asn  Ser  Gln  Asn
          195                 200                      205

Ile  Leu  Ala  Thr  Tyr  Leu  Ser  Gly  Ala  Gln  Val  Ser  Thr  Ile  Thr  Pro
     210                 215                      220

Thr  Ser  Thr  Arg  Gln  Thr  Thr  Ala  Met  Asp  Phe  Ser  Tyr  Ala  Asn  Glu
225                      230                 235                       240

Thr  Val  Cys  Trp  Val  His  Val  Gly  Asp  Ser  Ala  Ala  Gln  Thr  Gln  Leu
               245                 250                      255

Lys  Cys  Ala  Arg  Met  Pro  Gly  Leu  Lys  Gly  Phe  Val  Asp  Glu  His  Thr
               260                 265                      270

Ile  Asn  Ile  Ser  Leu  Ser  Leu  His  His  Val  Glu  Gln  Met  Ala  Ile  Asp
          275                 280                      285

Trp  Leu  Thr  Gly  Asn  Phe  Tyr  Phe  Val  Asp  Asp  Ile  Asp  Asp  Arg  Ile
     290                 295                      300

Phe  Val  Cys  Asn  Arg  Asn  Gly  Asp  Thr  Cys  Val  Thr  Leu  Leu  Asp  Leu
305                      310                 315                       320
```

```
Glu Leu Tyr Asn Pro Lys Gly Ile Ala Leu Asp Pro Ala Met Gly Lys
                325             330             335
Val Phe Phe Thr Asp Tyr Gly Gln Ile Pro Lys Val Glu Arg Cys Asp
            340             345             350
Met Asp Gly Gln Asn Arg Thr Lys Leu Val Asp Ser Lys Ile Val Phe
            355             360             365
Pro His Gly Ile Thr Leu Asp Leu Val Ser Arg Leu Val Tyr Trp Ala
    370             375             380
Asp Ala Tyr Leu Asp Tyr Ile Glu Val Val Asp Tyr Glu Gly Lys Gly
385             390             395             400
Arg Gln Thr Ile Ile Gln Gly Ile Leu Ile Glu His Leu Tyr Gly Leu
                405             410             415
Thr Val Phe Glu Asn Tyr Leu Tyr Ala Thr Asn Ser Asp Asn Ala Asn
            420             425             430
Ala Gln Gln Lys Thr Ser Val Ile Arg Val Asn Arg Phe Asn Ser Thr
        435             440             445
Glu Tyr Gln Val Val Thr Arg Val Asp Lys Gly Gly Ala Leu His Ile
    450             455             460
Tyr His Gln Arg Arg Gln Pro Arg Val Arg Ser His Ala Cys Glu Asn
465             470             475             480
Asp Gln Tyr Gly Lys Pro Gly Gly Cys Ser Asp Ile Cys Leu Leu Ala
            485             490             495
Asn Ser His Lys Ala Arg Thr Cys Arg Cys Arg Ser Gly Phe Ser Leu
            500             505             510
Gly Ser Asp Gly Lys Ser Cys Lys Lys Pro Glu His Glu Leu Phe Leu
        515             520             525
Val Tyr Gly Lys Gly Arg Pro Gly Ile Ile Arg Gly Met Asp Met Gly
    530             535             540
Ala Lys Val Pro Asp Glu His Met Ile Pro Ile Glu Asn Leu Met Asn
545             550             555             560
Pro Arg Ala Leu Asp Phe His Ala Glu Thr Gly Phe Ile Tyr Phe Ala
            565             570             575
Asp Thr Thr Ser Tyr Leu Ile Gly Arg Gln Lys Ile Asp Gly Thr Glu
            580             585             590
Arg Glu Thr Ile Leu Lys Asp Gly Ile His Asn Val Glu Gly Val Ala
        595             600             605
Val Asp Trp Met Gly Asp Asn Leu Tyr Trp Thr Asp Asp Gly Pro Lys
    610             615             620
Lys Thr Ile Ser Val Ala Arg Leu Glu Lys Ala Ala Gln Thr Arg Lys
625             630             635             640
Thr Leu Ile Glu Gly Lys Met Thr His Pro Arg Ala Ile Val Val Asp
            645             650             655
Pro Leu Asn Gly Trp Met Tyr Trp Thr Asp Trp Glu Glu Asp Pro Lys
            660             665             670
Asp Ser Arg Arg Gly Arg Leu Glu Arg Ala Trp Met Asp Gly Ser His
        675             680             685
Arg Asp Ile Phe Val Thr Ser Lys Thr Val Leu Trp Pro Asn Gly Leu
    690             695             700
Ser Leu Asp Ile Pro Ala Gly Arg Leu Tyr Trp Val Asp Ala Phe Tyr
705             710             715             720
Asp Arg Ile Glu Thr Ile Leu Leu Asn Gly Thr Asp Arg Lys Ile Val
            725             730             735
Tyr Glu Gly Pro Glu Leu Asn His Ala Phe Gly Leu Cys His His Gly
            740             745             750
```

```
Asn Tyr Leu Phe Trp Thr Glu Tyr Arg Ser Gly Ser Val Tyr Arg Leu
        755                 760                 765
Glu Arg Gly Val Gly Gly Ala Pro Pro Thr Val Thr Leu Leu Arg Ser
    770                 775                 780
Glu Arg Pro Pro Ile Phe Glu Ile Arg Met Tyr Asp Ala Gln Gln Gln
785                     790                 795                 800
Gln Val Gly Thr Asn Lys Cys Arg Val Asn Asn Gly Gly Cys Ser Ser
                805                 810                 815
Leu Cys Leu Ala Thr Pro Gly Ser Arg Gln Cys Ala Cys Ala Glu Asp
            820                 825                 830
Gln Val Leu Asp Ala Asp Gly Val Thr Cys Leu Ala Asn Pro Ser Tyr
        835                 840                 845
Val Pro Pro Pro Gln Cys Gln Pro Gly Glu Phe Ala Cys Ala Asn Ser
    850                 855                 860
Arg Cys Ile Gln Glu Arg Trp Lys Cys Asp Gly Asp Asn Asp Cys Leu
865                 870                 875                 880
Asp Asn Ser Asp Glu Ala Pro Ala Leu Cys His Gln His Thr Cys Pro
                885                 890                 895
Ser Asp Arg Phe Lys Cys Glu Asn Asn Arg Cys Ile Pro Asn Arg Trp
            900                 905                 910
Leu Cys Asp Gly Asp Asn Asp Cys Gly Asn Ser Glu Asp Glu Ser Asn
        915                 920                 925
Ala Thr Cys Ser Ala Arg Thr Cys Pro Pro Asn Gln Phe Ser Cys Ala
    930                 935                 940
Ser Gly Arg Cys Ile Pro Ile Ser Trp Thr Cys Asp Leu Asp Asp Asp
945                 950                 955                 960
Cys Gly Asp Arg Ser Asp Glu Ser Ala Ser Cys Ala Tyr Pro Thr Cys
                965                 970                 975
Phe Pro Leu Thr Gln Phe Thr Cys Asn Asn Gly Arg Cys Ile Asn Ile
            980                 985                 990
Asn Trp Arg Cys Asp Asn Asp Asn Asp Cys Gly Asp Asn Ser Asp Glu
        995                 1000                1005
Ala Gly Cys Ser His Ser Cys Ser Ser Thr Gln Phe Lys Cys Asn Ser
    1010                1015                1020
Gly Arg Cys Ile Pro Glu His Trp Thr Cys Asp Gly Asp Asn Asp Cys
1025                1030                1035                1040
Gly Asp Tyr Ser Asp Glu Thr His Ala Asn Cys Thr Asn Gln Ala Thr
                1045                1050                1055
Arg Pro Pro Gly Gly Cys His Thr Asp Glu Phe Gln Cys Arg Leu Asp
            1060                1065                1070
Gly Leu Cys Ile Pro Leu Arg Trp Arg Cys Asp Gly Asp Thr Asp Cys
        1075                1080                1085
Met Asp Ser Ser Asp Glu Lys Ser Cys Glu Gly Val Thr His Val Cys
    1090                1095                1100
Asp Pro Ser Val Lys Phe Gly Cys Lys Asp Ser Ala Arg Cys Ile Ser
1105                1110                1115                1120
Lys Ala Trp Val Cys Asp Gly Asp Asn Asp Cys Glu Asp Asn Ser Asp
                1125                1130                1135
Glu Glu Asn Cys Glu Ser Leu Ala Cys Arg Pro Pro Ser His Pro Cys
            1140                1145                1150
Ala Asn Asn Thr Ser Val Cys Leu Pro Pro Asp Lys Leu Cys Asp Gly
        1155                1160                1165
Asn Asp Asp Cys Gly Asp Gly Ser Asp Glu Gly Glu Leu Cys Asp Gln
```

-continued

```
                1170                    1175                    1180
Cys  Ser  Leu  Asn  Asn  Gly  Gly  Cys  Ser  His  Asn  Cys  Ser  Val  Ala  Pro
1185                    1190                    1195                    1200
Gly  Glu  Gly  Ile  Val  Cys  Ser  Cys  Pro  Leu  Gly  Met  Glu  Leu  Gly  Pro
                1205                    1210                    1215
Asp  Asn  His  Thr  Cys  Gln  Ile  Gln  Ser  Tyr  Cys  Ala  Lys  His  Leu  Lys
                1220                    1225                    1230
Cys  Ser  Gln  Lys  Cys  Asp  Gln  Asn  Lys  Phe  Ser  Val  Lys  Cys  Ser  Cys
                1235                    1240                    1245
Tyr  Glu  Gly  Trp  Val  Leu  Glu  Pro  Asp  Gly  Glu  Ser  Cys  Arg  Ser  Leu
                1250                    1255                    1260
Asp  Pro  Phe  Lys  Pro  Phe  Ile  Ile  Phe  Ser  Asn  Arg  His  Glu  Ile  Arg
1265                    1270                    1275                    1280
Arg  Ile  Asp  Leu  His  Lys  Gly  Asp  Tyr  Ser  Val  Leu  Val  Pro  Gly  Leu
                1285                    1290                    1295
Arg  Asn  Thr  Ile  Ala  Leu  Asp  Phe  His  Leu  Ser  Gln  Ser  Ala  Leu  Tyr
                1300                    1305                    1310
Trp  Thr  Asp  Val  Val  Glu  Asp  Lys  Ile  Tyr  Arg  Gly  Lys  Leu  Leu  Asp
                1315                    1320                    1325
Asn  Gly  Ala  Leu  Thr  Ser  Phe  Glu  Val  Val  Ile  Gln  Tyr  Gly  Leu  Ala
                1330                    1335                    1340
Thr  Pro  Glu  Gly  Leu  Ala  Val  Asp  Trp  Ile  Ala  Gly  Asn  Ile  Tyr  Trp
1345                    1350                    1355                    1360
Val  Glu  Ser  Asn  Leu  Asp  Gln  Ile  Glu  Val  Ala  Lys  Leu  Asp  Gly  Thr
                1365                    1370                    1375
Leu  Arg  Thr  Thr  Leu  Leu  Ala  Gly  Asp  Ile  Glu  His  Pro  Arg  Ala  Ile
                1380                    1385                    1390
Ala  Leu  Asp  Pro  Arg  Asp  Gly  Ile  Leu  Phe  Trp  Thr  Asp  Trp  Asp  Ala
                1395                    1400                    1405
Ser  Leu  Pro  Arg  Ile  Glu  Ala  Ala  Ser  Met  Ser  Gly  Ala  Gly  Arg  Arg
                1410                    1415                    1420
Thr  Val  His  Arg  Glu  Thr  Gly  Ser  Gly  Gly  Trp  Pro  Asn  Gly  Leu  Thr
1425                    1430                    1435                    1440
Val  Asp  Tyr  Leu  Glu  Lys  Arg  Ile  Leu  Trp  Ile  Asp  Ala  Arg  Ser  Asp
                1445                    1450                    1455
Ala  Ile  Tyr  Ser  Ala  Arg  Tyr  Asp  Gly  Ser  Gly  His  Met  Glu  Val  Leu
                1460                    1465                    1470
Arg  Gly  His  Glu  Phe  Leu  Ser  His  Pro  Phe  Ala  Val  Thr  Leu  Tyr  Gly
                1475                    1480                    1485
Gly  Glu  Val  Tyr  Trp  Thr  Asp  Trp  Arg  Thr  Asn  Thr  Leu  Ala  Lys  Ala
                1490                    1495                    1500
Asn  Lys  Trp  Thr  Gly  His  Asn  Val  Thr  Val  Val  Gln  Arg  Thr  Asn  Thr
1505                    1510                    1515                    1520
Gln  Pro  Phe  Asp  Leu  Gln  Val  Tyr  His  Pro  Ser  Arg  Gln  Pro  Met  Ala
                1525                    1530                    1535
Pro  Asn  Pro  Cys  Glu  Ala  Asn  Gly  Gly  Gln  Gly  Pro  Cys  Ser  His  Leu
                1540                    1545                    1550
Cys  Leu  Ile  Asn  Tyr  Asn  Arg  Thr  Val  Ser  Cys  Ala  Cys  Pro  His  Leu
                1555                    1560                    1565
Met  Lys  Leu  His  Lys  Asp  Asn  Thr  Thr  Cys  Tyr  Glu  Phe  Lys  Lys  Phe
1570                    1575                    1580
Leu  Leu  Tyr  Ala  Arg  Gln  Met  Glu  Ile  Arg  Gly  Val  Asp  Leu  Asp  Ala
1585                    1590                    1595                    1600
```

```
Pro Tyr Tyr Asn Tyr Ile Ile Ser Phe Thr Val Pro Asp Ile Asp Asn
            1605                1610                1615
Val Thr Val Leu Asp Tyr Asp Ala Arg Glu Gln Arg Val Tyr Trp Ser
        1620                1625                1630
Asp Val Arg Thr Gln Ala Ile Lys Arg Ala Phe Ile Asn Gly Thr Gly
            1635                1640                1645
Val Glu Thr Val Val Ser Ala Asp Leu Pro Asn Ala His Gly Leu Ala
        1650                1655                1660
Val Asp Trp Val Ser Arg Asn Leu Phe Trp Thr Ser Tyr Asp Thr Asn
1665                1670                1675                1680
Lys Lys Gln Ile Asn Val Ala Arg Leu Asp Gly Ser Phe Lys Asn Ala
            1685                1690                1695
Val Val Gln Gly Leu Glu Gln Pro His Gly Leu Val Val His Pro Leu
            1700                1705                1710
Arg Gly Lys Leu Tyr Trp Thr Asp Gly Asp Asn Ile Ser Met Ala Asn
            1715                1720                1725
Met Asp Gly Ser Asn Arg Thr Leu Leu Phe Ser Gly Gln Lys Gly Pro
        1730                1735                1740
Val Gly Leu Ala Ile Asp Phe Pro Glu Ser Lys Leu Tyr Trp Ile Ser
1745                1750                1755                1760
Ser Gly Asn His Thr Ile Asn Arg Cys Asn Leu Asp Gly Ser Gly Leu
            1765                1770                1775
Glu Val Ile Asp Ala Met Arg Ser Gln Leu Gly Lys Ala Thr Ala Leu
            1780                1785                1790
Ala Ile Met Gly Asp Lys Leu Trp Trp Ala Asp Gln Val Ser Glu Lys
            1795                1800                1805
Met Gly Thr Cys Ser Lys Ala Asp Gly Ser Gly Ser Val Val Leu Arg
        1810                1815                1820
Asn Ser Thr Thr Leu Val Met His Met Lys Val Tyr Asp Glu Ser Ile
1825                1830                1835                1840
Gln Leu Asp His Lys Gly Thr Asn Pro Cys Ser Val Asn Asn Gly Asp
            1845                1850                1855
Cys Ser Gln Leu Cys Leu Pro Thr Ser Glu Thr Thr Arg Ser Cys Met
            1860                1865                1870
Cys Thr Ala Gly Tyr Ser Leu Arg Ser Gly Gln Gln Ala Cys Glu Gly
        1875                1880                1885
Val Gly Ser Phe Leu Leu Tyr Ser Val His Glu Gly Ile Arg Gly Ile
        1890                1895                1900
Pro Leu Asp Pro Asn Asp Lys Ser Asp Ala Leu Val Pro Val Ser Gly
1905                1910                1915                1920
Thr Ser Leu Ala Val Gly Ile Asp Phe His Ala Glu Asn Asp Thr Ile
            1925                1930                1935
Tyr Trp Val Asp Met Gly Leu Ser Thr Ile Ser Arg Ala Lys Arg Asp
                1940                1945                1950
Gln Thr Trp Arg Glu Asp Val Val Thr Asn Gly Ile Gly Arg Val Glu
        1955                1960                1965
Gly Ile Ala Val Asp Trp Ile Ala Gly Asn Ile Tyr Trp Thr Asp Gln
    1970                1975                1980
Gly Phe Asp Val Ile Glu Val Ala Arg Leu Asn Gly Ser Phe Arg Tyr
1985                1990                1995                2000
Val Val Ile Ser Gln Gly Leu Asp Lys Pro Arg Ala Ile Thr Val His
            2005                2010                2015
Pro Glu Lys Gly Tyr Leu Phe Trp Thr Glu Trp Gly Gln Tyr Pro Arg
            2020                2025                2030
```

Ile Glu Arg Ser Arg Leu Asp Gly Thr Glu Arg Val Val Leu Val Asn
           2035                2040                2045

Val Ser Ile Ser Trp Pro Asn Gly Ile Ser Val Asp Tyr Gln Asp Gly
    2050                2055                2060

Lys Leu Tyr Trp Cys Asp Ala Arg Thr Asp Lys Ile Glu Arg Ile Asp
2065            2070                2075                2080

Leu Glu Thr Gly Glu Asn Arg Glu Val Val Leu Ser Ser Asn Asn Met
                2085                2090                2095

Asp Met Phe Ser Val Ser Val Phe Glu Asp Phe Ile Tyr Trp Ser Asp
            2100                2105                2110

Arg Thr His Ala Asn Gly Ser Ile Lys Arg Gly Ser Lys Asp Asn Ala
            2115                2120                2125

Thr Asp Ser Val Pro Leu Arg Thr Gly Ile Gly Val Gln Leu Lys Asp
            2130                2135                2140

Ile Lys Val Phe Asn Arg Asp Arg Gln Lys Gly Thr Asn Val Cys Ala
2145            2150                2155                2160

Val Ala Asn Gly Gly Cys Gln Gln Leu Cys Leu Tyr Arg Gly Arg Gly
                2165                2170                2175

Gln Arg Ala Cys Ala Cys Ala His Gly Met Leu Ala Glu Asp Gly Ala
            2180                2185                2190

Ser Cys Arg Glu Tyr Ala Gly Tyr Leu Leu Tyr Ser Glu Arg Thr Ile
            2195                2200                2205

Leu Lys Ser Ile His Leu Ser Asp Glu Arg Asn Leu Asn Ala Pro Val
            2210                2215                2220

Gln Pro Phe Glu Asp Pro Glu His Met Lys Asn Val Ile Ala Leu Ala
2225            2230                2235                2240

Phe Asp Tyr Arg Ala Gly Thr Ser Pro Gly Thr Pro Asn Arg Ile Phe
                2245                2250                2255

Phe Ser Asp Ile His Phe Gly Asn Ile Gln Gln Ile Asn Asp Asp Gly
            2260                2265                2270

Ser Arg Arg Ile Thr Ile Val Glu Asn Val Gly Ser Val Glu Gly Leu
            2275                2280                2285

Ala Tyr His Arg Gly Trp Asp Thr Leu Tyr Trp Thr Ser Tyr Thr Thr
            2290                2295                2300

Ser Thr Ile Thr Arg His Thr Val Asp Gln Thr Arg Pro Gly Ala Phe
2305            2310                2315                2320

Glu Arg Glu Thr Val Ile Thr Met Ser Gly Asp Asp His Pro Arg Ala
                2325                2330                2335

Phe Val Leu Asp Glu Cys Gln Asn Leu Met Phe Trp Thr Asn Trp Asn
            2340                2345                2350

Glu Gln His Pro Ser Ile Met Arg Ala Ala Leu Ser Gly Ala Asn Val
            2355                2360                2365

Leu Thr Leu Ile Glu Lys Asp Ile Arg Thr Pro Asn Gly Leu Ala Ile
    2370                2375                2380

Asp His Arg Ala Glu Lys Leu Tyr Phe Ser Asp Ala Thr Leu Asp Lys
2385            2390                2395                2400

Ile Glu Arg Cys Glu Tyr Asp Gly Ser His Arg Tyr Val Ile Leu Lys
                2405                2410                2415

Ser Glu Pro Val His Pro Phe Gly Leu Ala Val Tyr Gly Glu His Ile
            2420                2425                2430

Phe Trp Thr Asp Trp Val Arg Arg Ala Val Gln Arg Ala Asn Lys His
            2435                2440                2445

Val Gly Ser Asn Met Lys Leu Leu Arg Val Asp Ile Pro Gln Gln Pro

-continued

```
              2450                    2455                    2460
Met  Gly  Ile  Ile  Ala  Val  Ala  Asn  Asp  Thr  Asn  Ser  Cys  Glu  Leu  Ser
2465                    2470                    2475                    2480

Pro  Cys  Arg  Ile  Asn  Asn  Gly  Gly  Cys  Gln  Asp  Leu  Cys  Leu  Leu  Thr
                    2485                    2490                    2495

His  Gln  Gly  His  Val  Asn  Cys  Ser  Cys  Arg  Gly  Gly  Arg  Ile  Leu  Gln
               2500                    2505                    2510

Asp  Asp  Leu  Thr  Cys  Arg  Ala  Val  Asn  Ser  Ser  Cys  Arg  Ala  Gln  Asp
               2515                    2520                    2525

Glu  Phe  Glu  Cys  Ala  Asn  Gly  Glu  Cys  Ile  Asn  Phe  Ser  Leu  Thr  Cys
               2530                    2535                    2540

Asp  Gly  Val  Pro  His  Cys  Lys  Asp  Lys  Ser  Asp  Glu  Lys  Pro  Ser  Tyr
2545                    2550                    2555                    2560

Cys  Asn  Ser  Arg  Arg  Cys  Lys  Lys  Thr  Phe  Arg  Gln  Cys  Ser  Asn  Gly
                    2565                    2570                    2575

Arg  Cys  Val  Ser  Asn  Met  Leu  Trp  Cys  Asn  Gly  Ala  Asp  Asp  Cys  Gly
                    2580                    2585                    2590

Asp  Gly  Ser  Asp  Glu  Ile  Pro  Cys  Asn  Lys  Thr  Ala  Cys  Gly  Val  Gly
               2595                    2600                    2605

Glu  Phe  Arg  Cys  Arg  Asp  Gly  Thr  Cys  Ile  Gly  Asn  Ser  Ser  Arg  Cys
2610                    2615                    2620

Asn  Gln  Phe  Val  Asp  Cys  Glu  Asp  Ala  Ser  Asp  Glu  Met  Asn  Cys  Ser
2625                    2630                    2635                    2640

Ala  Thr  Asp  Cys  Ser  Ser  Tyr  Phe  Arg  Leu  Gly  Val  Lys  Gly  Val  Leu
                    2645                    2650                    2655

Phe  Gln  Pro  Cys  Glu  Arg  Thr  Ser  Leu  Cys  Tyr  Ala  Pro  Ser  Trp  Val
                    2660                    2665                    2670

Cys  Asp  Gly  Ala  Asn  Asp  Cys  Gly  Asp  Tyr  Ser  Asp  Glu  Arg  Asp  Cys
               2675                    2680                    2685

Pro  Gly  Val  Lys  Arg  Pro  Arg  Cys  Pro  Leu  Asn  Tyr  Phe  Ala  Cys  Pro
2690                    2695                    2700

Ser  Gly  Arg  Cys  Ile  Pro  Met  Ser  Trp  Thr  Cys  Asp  Lys  Glu  Asp  Asp
2705                    2710                    2715                    2720

Cys  Glu  His  Gly  Glu  Asp  Glu  Thr  His  Cys  Asn  Lys  Phe  Cys  Ser  Glu
               2725                    2730                    2735

Ala  Gln  Phe  Glu  Cys  Gln  Asn  His  Arg  Cys  Ile  Ser  Lys  Gln  Trp  Leu
                    2740                    2745                    2750

Cys  Asp  Gly  Ser  Asp  Asp  Cys  Gly  Asp  Gly  Ser  Asp  Glu  Ala  Ala  His
               2755                    2760                    2765

Cys  Glu  Gly  Lys  Thr  Cys  Gly  Pro  Ser  Ser  Phe  Ser  Cys  Pro  Gly  Thr
2770                    2775                    2780

His  Val  Cys  Val  Pro  Glu  Arg  Trp  Leu  Cys  Asp  Gly  Asp  Lys  Asp  Cys
2785                    2790                    2795                    2800

Ala  Asp  Gly  Ala  Asp  Glu  Ser  Ile  Ala  Ala  Gly  Cys  Leu  Tyr  Asn  Ser
                    2805                    2810                    2815

Thr  Cys  Asp  Asp  Arg  Glu  Phe  Met  Cys  Gln  Asn  Arg  Gln  Cys  Ile  Pro
                    2820                    2825                    2830

Lys  His  Phe  Val  Cys  Asp  His  Asp  Arg  Asp  Cys  Ala  Asp  Gly  Ser  Asp
                    2835                    2840                    2845

Glu  Ser  Pro  Glu  Cys  Glu  Tyr  Pro  Thr  Cys  Gly  Pro  Ser  Glu  Phe  Arg
               2850                    2855                    2860

Cys  Ala  Asn  Gly  Arg  Cys  Leu  Ser  Ser  Arg  Gln  Trp  Glu  Cys  Asp  Gly
2865                    2870                    2875                    2880
```

```
Glu Asn Asp Cys His Asp Gln Ser Asp Glu Ala Pro Lys Asn Pro His
            2885                2890                2895

Cys Thr Ser Pro Glu His Lys Cys Asn Ala Ser Ser Gln Phe Leu Cys
        2900                2905                2910

Ser Ser Gly Arg Cys Val Ala Glu Ala Leu Leu Cys Asn Gly Gln Asp
        2915                2920                2925

Asp Cys Gly Asp Ser Ser Asp Glu Arg Gly Cys His Ile Asn Glu Cys
        2930                2935                2940

Leu Ser Arg Lys Leu Ser Gly Cys Ser Gln Asp Cys Glu Asp Leu Lys
2945                2950                2955                2960

Ile Gly Phe Lys Cys Arg Cys Arg Pro Gly Phe Arg Leu Lys Asp Asp
            2965                2970                2975

Gly Arg Thr Cys Ala Asp Val Asp Glu Cys Ser Thr Thr Phe Pro Cys
        2980                2985                2990

Ser Gln Arg Cys Ile Asn Thr His Gly Ser Tyr Lys Cys Leu Cys Val
        2995                3000                3005

Glu Gly Tyr Ala Pro Arg Gly Gly Asp Pro His Ser Cys Lys Ala Val
        3010                3015                3020

Thr Asp Glu Glu Pro Phe Leu Ile Phe Ala Asn Arg Tyr Tyr Leu Arg
3025                3030                3035                3040

Lys Leu Asn Leu Asp Gly Ser Asn Tyr Thr Leu Leu Lys Gln Gly Leu
            3045                3050                3055

Asn Asn Ala Val Ala Leu Asp Phe Asp Tyr Arg Glu Gln Met Ile Tyr
            3060                3065                3070

Trp Thr Asp Val Thr Thr Gln Gly Ser Met Ile Arg Arg Met His Leu
        3075                3080                3085

Asn Gly Ser Asn Val Gln Val Leu His Arg Thr Gly Leu Ser Asn Pro
        3090                3095                3100

Asp Gly Leu Ala Val Asp Trp Val Gly Gly Asn Leu Tyr Trp Cys Asp
3105                3110                3115                3120

Lys Gly Arg Asp Thr Ile Glu Val Ser Lys Leu Asn Gly Ala Tyr Arg
            3125                3130                3135

Thr Val Leu Val Ser Ser Gly Leu Arg Glu Pro Arg Ala Leu Val Val
            3140                3145                3150

Asp Val Gln Asn Gly Tyr Leu Tyr Trp Thr Asp Trp Gly Asp His Ser
        3155                3160                3165

Leu Ile Gly Arg Ile Gly Met Asp Gly Ser Ser Arg Ser Val Ile Val
        3170                3175                3180

Asp Thr Lys Ile Thr Trp Pro Asn Gly Leu Thr Leu Asp Tyr Val Thr
3185                3190                3195                3200

Glu Arg Ile Tyr Trp Ala Asp Ala Arg Glu Asp Tyr Ile Glu Phe Ala
            3205                3210                3215

Ser Leu Asp Gly Ser Asn Arg His Val Val Leu Ser Gln Asp Ile Pro
        3220                3225                3230

His Ile Phe Ala Leu Thr Leu Phe Glu Asp Tyr Val Tyr Trp Thr Asp
        3235                3240                3245

Trp Glu Thr Lys Ser Ile Asn Arg Ala His Lys Thr Thr Gly Thr Asn
3250                3255                3260

Lys Thr Leu Leu Ile Ser Thr Leu His Arg Pro Met Asp Leu His Val
3265                3270                3275                3280

Phe His Ala Leu Arg Gln Pro Asp Val Pro Asn His Pro Cys Lys Val
            3285                3290                3295

Asn Asn Gly Gly Cys Ser Asn Leu Cys Leu Leu Ser Pro Gly Gly Gly
        3300                3305                3310
```

His Lys Cys Ala Cys Pro Thr Asn Phe Tyr Leu Gly Ser Asp Gly Arg
       3315              3320                  3325

Thr Cys Val Ser Asn Cys Thr Ala Ser Gln Phe Val Cys Lys Asn Asp
       3330              3335                  3340

Lys Cys Ile Pro Phe Trp Trp Lys Cys Asp Thr Glu Asp Asp Cys Gly
3345              3350              3355                  3360

Asp His Ser Asp Glu Pro Pro Asp Cys Pro Glu Phe Lys Cys Arg Pro
                3365              3370                  3375

Gly Gln Phe Gln Cys Ser Thr Gly Ile Cys Thr Asn Pro Ala Phe Ile
              3380              3385                  3390

Cys Asp Gly Asp Asn Asp Cys Gln Asp Asn Ser Asp Glu Ala Asn Cys
              3395              3400                  3405

Asp Ile His Val Cys Leu Pro Ser Gln Phe Lys Cys Thr Asn Thr Asn
              3410              3415                  3420

Arg Cys Ile Pro Gly Ile Phe Arg Cys Asn Gly Gln Asp Asn Cys Gly
3425              3430              3435                  3440

Asp Gly Glu Asp Glu Arg Asp Cys Pro Glu Val Thr Cys Ala Pro Asn
                3445              3450                  3455

Gln Phe Gln Cys Ser Ile Thr Lys Arg Cys Ile Pro Arg Val Trp Val
              3460              3465                  3470

Cys Asp Arg Asp Asn Asp Cys Val Asp Gly Ser Asp Glu Pro Ala Asn
              3475              3480                  3485

Cys Thr Gln Met Thr Cys Gly Val Asp Glu Phe Arg Cys Lys Asp Ser
              3490              3495                  3500

Gly Arg Cys Ile Pro Ala Arg Trp Lys Cys Asp Gly Glu Asp Asp Cys
3505              3510              3515                  3520

Gly Asp Gly Ser Asp Glu Pro Lys Glu Glu Cys Asp Glu Arg Thr Cys
              3525              3530                  3535

Glu Pro Tyr Gln Phe Arg Cys Lys Asn Asn Arg Cys Val Pro Gly Arg
              3540              3545                  3550

Trp Gln Cys Asp Tyr Asp Asn Asp Cys Gly Asp Asn Ser Asp Glu Glu
              3555              3560                  3565

Ser Cys Thr Pro Arg Pro Cys Ser Glu Ser Glu Phe Ser Cys Ala Asn
3570              3575              3580

Gly Arg Cys Ile Ala Gly Arg Trp Lys Cys Asp Gly Asp His Asp Cys
3585              3590              3595                  3600

Ala Asp Gly Ser Asp Glu Lys Asp Cys Thr Pro Arg Cys Asp Met Asp
              3605              3610                  3615

Gln Phe Gln Cys Lys Ser Gly His Cys Ile Pro Leu Arg Trp Arg Cys
              3620              3625                  3630

Asp Ala Asp Ala Asp Cys Met Asp Gly Ser Asp Glu Glu Ala Cys Gly
              3635              3640                  3645

Thr Gly Val Arg Thr Cys Pro Leu Asp Glu Phe Gln Cys Asn Asn Thr
       3650              3655                  3660

Leu Cys Lys Pro Leu Ala Trp Lys Cys Asp Gly Glu Asp Asp Cys Gly
3665              3670              3675                  3680

Asp Asn Ser Asp Glu Asn Pro Glu Glu Cys Ala Arg Phe Val Cys Pro
              3685              3690                  3695

Pro Asn Arg Pro Phe Arg Cys Lys Asn Asp Arg Val Cys Leu Trp Ile
              3700              3705                  3710

Gly Arg Gln Cys Asp Gly Thr Asp Asn Cys Gly Asp Gly Thr Asp Glu
              3715              3720                  3725

Glu Asp Cys Glu Pro Pro Thr Ala His Thr Thr His Cys Lys Asp Lys

-continued

```
                    3730                         3735                         3740
Lys  Glu  Phe  Leu  Cys  Arg  Asn  Gln  Arg  Cys  Leu  Ser  Ser  Ser  Leu  Arg
3745                         3750                         3755                    3760

Cys  Asn  Met  Phe  Asp  Asp  Cys  Gly  Asp  Gly  Ser  Asp  Glu  Glu  Asp  Cys
                    3765                         3770                         3775

Ser  Ile  Asp  Pro  Lys  Leu  Thr  Ser  Cys  Ala  Thr  Asn  Ala  Ser  Ile  Cys
                    3780                         3785                         3790

Gly  Asp  Glu  Ala  Arg  Cys  Val  Arg  Thr  Glu  Lys  Ala  Ala  Tyr  Cys  Ala
                    3795                         3800                    3805

Cys  Arg  Ser  Gly  Phe  His  Thr  Val  Pro  Gly  Gln  Pro  Gly  Cys  Gln  Asp
                    3810                         3815                    3820

Ile  Asn  Glu  Cys  Leu  Arg  Phe  Gly  Thr  Cys  Ser  Gln  Leu  Cys  Asn  Asn
3825                         3830                         3835                    3840

Thr  Lys  Gly  Gly  His  Leu  Cys  Ser  Cys  Ala  Arg  Asn  Phe  Met  Lys  Thr
                              3845                         3850                    3855

His  Asn  Thr  Cys  Lys  Ala  Glu  Gly  Ser  Glu  Tyr  Gln  Val  Leu  Tyr  Ile
                    3860                         3865                         3870

Ala  Asp  Asp  Asn  Glu  Ile  Arg  Ser  Leu  Phe  Pro  Gly  His  Pro  His  Ser
                    3875                         3880                         3885

Ala  Tyr  Glu  Gln  Ala  Phe  Gln  Gly  Asp  Glu  Ser  Val  Arg  Ile  Asp  Ala
                    3890                         3895                    3900

Met  Asp  Val  His  Val  Lys  Ala  Gly  Arg  Val  Tyr  Trp  Thr  Asn  Trp  His
3905                         3910                         3915                    3920

Thr  Gly  Thr  Ile  Ser  Tyr  Arg  Ser  Leu  Pro  Pro  Ala  Ala  Pro  Pro  Thr
                              3925                         3930                    3935

Thr  Ser  Asn  Arg  His  Arg  Arg  Gln  Ile  Asp  Arg  Gly  Val  Thr  His  Leu
                    3940                         3945                         3950

Asn  Ile  Ser  Gly  Leu  Lys  Met  Pro  Arg  Gly  Ile  Ala  Ile  Asp  Trp  Val
                    3955                         3960                    3965

Ala  Gly  Asn  Val  Tyr  Trp  Thr  Asp  Ser  Gly  Arg  Asp  Val  Ile  Glu  Val
                    3970                         3975                    3980

Ala  Gln  Met  Lys  Gly  Glu  Asn  Arg  Lys  Thr  Leu  Ile  Ser  Gly  Met  Ile
3985                         3990                         3995                    4000

Asp  Glu  Pro  His  Ala  Ile  Val  Val  Asp  Pro  Leu  Arg  Gly  Thr  Met  Tyr
                              4005                         4010                    4015

Trp  Ser  Asp  Trp  Gly  Asn  His  Pro  Lys  Ile  Glu  Thr  Ala  Ala  Met  Asp
                    4020                         4025                    4030

Gly  Thr  Leu  Arg  Glu  Thr  Leu  Val  Gln  Asp  Asn  Ile  Gln  Trp  Pro  Thr
                    4035                         4040                    4045

Gly  Leu  Ala  Val  Asp  Tyr  His  Asn  Glu  Arg  Leu  Tyr  Trp  Ala  Asp  Ala
                    4050                         4055                    4060

Lys  Leu  Ser  Val  Ile  Gly  Ser  Ile  Arg  Leu  Asn  Gly  Thr  Asp  Pro  Ile
4065                         4070                         4075                    4080

Val  Ala  Ala  Asp  Ser  Lys  Arg  Gly  Leu  Ser  His  Pro  Phe  Ser  Ile  Asp
                              4085                         4090                    4095

Val  Phe  Glu  Asp  Tyr  Ile  Tyr  Gly  Val  Thr  Tyr  Ile  Asn  Asn  Arg  Val
                    4100                         4105                         4110

Phe  Lys  Ile  His  Lys  Phe  Gly  His  Ser  Pro  Leu  Val  Asn  Leu  Thr  Gly
                    4115                         4120                         4125

Gly  Leu  Ser  His  Ala  Ser  Asp  Val  Val  Leu  Tyr  His  Gln  His  Lys  Gln
                    4130                         4135                         4140

Pro  Glu  Val  Thr  Asn  Pro  Cys  Asp  Arg  Lys  Lys  Cys  Glu  Trp  Leu  Cys
4145                         4150                         4155                    4160
```

-continued

Leu Leu Ser Pro Ser Gly Pro Val Cys Thr Cys Pro Asn Gly Lys Arg
                4165            4170                4175

Leu Asp Asn Gly Thr Cys Val Pro Val Pro Ser Pro Thr Pro Pro Pro
                4180            4185            4190

Asp Ala Pro Arg Pro Gly Thr Cys Asn Leu Gln Cys Phe Asn Gly Gly
                4195            4200            4205

Ser Cys Phe Leu Asn Ala Arg Arg Gln Pro Lys Cys Arg Cys Gln Pro
    4210            4215            4220

Arg Tyr Thr Gly Asp Lys Cys Glu Leu Asp Gln Cys Trp Glu His Cys
4225            4230            4235            4240

Arg Asn Gly Gly Thr Cys Ala Ala Ser Pro Ser Gly Met Pro Thr Cys
                4245            4250            4255

Arg Cys Pro Thr Gly Phe Thr Gly Pro Lys Cys Thr Gln Gln Val Cys
                4260            4265            4270

Ala Gly Tyr Cys Ala Asn Asn Ser Thr Cys Thr Val Asn Gln Gly Asn
                4275            4280            4285

Gln Pro Gln Cys Arg Cys Leu Pro Gly Phe Leu Gly Asp Arg Cys Gln
    4290            4295            4300

Tyr Arg Gln Cys Ser Gly Tyr Cys Glu Asn Phe Gly Thr Cys Gln Met
4305            4310            4315            4320

Ala Ala Asp Gly Ser Arg Gln Cys Arg Cys Thr Ala Tyr Phe Glu Gly
                4325            4330            4335

Ser Arg Cys Glu Val Asn Lys Cys Ser Arg Cys Leu Glu Gly Ala Cys
                4340            4345            4350

Val Val Asn Lys Gln Ser Gly Asp Val Thr Cys Asn Cys Thr Asp Gly
                4355            4360            4365

Arg Val Ala Pro Ser Cys Leu Thr Cys Val Gly His Cys Ser Asn Gly
                4370            4375            4380

Gly Ser Cys Thr Met Asn Ser Lys Met Met Pro Glu Cys Gln Cys Pro
4385            4390            4395            4400

Pro His Met Thr Gly Pro Arg Cys Glu Glu His Val Phe Ser Gln Gln
                4405            4410            4415

Gln Pro Gly His Ile Ala Ser Ile Leu Ile Pro Leu Leu Leu Leu Leu
                4420            4425            4430

Leu Leu Val Leu Val Ala Gly Val Val Phe Trp Tyr Lys Arg Arg Val
                4435            4440            4445

Gln Gly Ala Lys Gly Phe Gln His Gln Arg Met Thr Asn Gly Ala Met
                4450            4455            4460

Asn Val Glu Ile Gly Asn Pro Thr Tyr Lys Met Tyr Glu Gly Gly Glu
4465            4470            4475            4480

Pro Asp Asp Val Gly Gly Leu Leu Asp Ala Asp Phe Ala Leu Asp Pro
                4485            4490            4495

Asp Lys Pro Thr Asn Phe Thr Asn Pro Val Tyr Ala Thr Leu Tyr Met
                4500            4505            4510

Gly Gly His Gly Ser Arg His Ser Leu Ala Ser Thr Asp Glu Lys Arg
                4515            4520            4525

Glu Leu Leu Gly Arg Gly Pro Glu Asp Glu Ile Gly Asp Pro Leu Ala
    4530            4535            4540

( 2 ) INFORMATION FOR SEQ ID NO: 53:

( i ) SEQUENCE CHARACTERISTICS:
        ( A ) LENGTH: 487 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO: 53:

| Met | Ala | Gly | Leu | Leu | His | Leu | Val | Leu | Leu | Ser | Thr | Ala | Leu | Gly | Gly |
|---|---|---|---|---|---|---|---|---|---|---|---|---|---|---|---|
| 1 | | | | 5 | | | | | 10 | | | | | 15 | |

| Leu | Leu | Arg | Pro | Ala | Gly | Ser | Val | Phe | Leu | Pro | Arg | Asp | Gln | Ala | His |
|---|---|---|---|---|---|---|---|---|---|---|---|---|---|---|---|
| | | | 20 | | | | | 25 | | | | | 30 | | |

| Arg | Val | Leu | Gln | Arg | Ala | Arg | Arg | Ala | Asn | Ser | Phe | Leu | Glu | Glu | Val |
|---|---|---|---|---|---|---|---|---|---|---|---|---|---|---|---|
| | | 35 | | | | | 40 | | | | | 45 | | | |

| Lys | Gln | Gly | Asn | Leu | Glu | Arg | Glu | Cys | Leu | Glu | Glu | Ala | Cys | Ser | Leu |
|---|---|---|---|---|---|---|---|---|---|---|---|---|---|---|---|
| | 50 | | | | | 55 | | | | | 60 | | | | |

| Glu | Glu | Ala | Arg | Glu | Val | Phe | Glu | Asp | Ala | Glu | Gln | Thr | Asp | Glu | Phe |
|---|---|---|---|---|---|---|---|---|---|---|---|---|---|---|---|
| 65 | | | | | 70 | | | | | 75 | | | | | 80 |

| Trp | Ser | Lys | Tyr | Lys | Asp | Gly | Asp | Gln | Cys | Glu | Gly | His | Pro | Cys | Leu |
|---|---|---|---|---|---|---|---|---|---|---|---|---|---|---|---|
| | | | | 85 | | | | | 90 | | | | | 95 | |

| Asn | Gln | Gly | His | Cys | Lys | Asp | Gly | Ile | Gly | Asp | Tyr | Thr | Cys | Thr | Cys |
|---|---|---|---|---|---|---|---|---|---|---|---|---|---|---|---|
| | | | 100 | | | | | 105 | | | | | 110 | | |

| Ala | Glu | Gly | Phe | Glu | Gly | Lys | Asn | Cys | Glu | Phe | Ser | Thr | Arg | Glu | Ile |
|---|---|---|---|---|---|---|---|---|---|---|---|---|---|---|---|
| | | | 115 | | | | | 120 | | | | | 125 | | |

| Cys | Ser | Leu | Asp | Asn | Gly | Gly | Cys | Asp | Gln | Phe | Cys | Arg | Glu | Glu | Arg |
|---|---|---|---|---|---|---|---|---|---|---|---|---|---|---|---|
| | | 130 | | | | | 135 | | | | | 140 | | | |

| Ser | Glu | Val | Arg | Cys | Ser | Cys | Ala | His | Gly | Tyr | Val | Leu | Gly | Asp | Asp |
|---|---|---|---|---|---|---|---|---|---|---|---|---|---|---|---|
| 145 | | | | | 150 | | | | | 155 | | | | | 160 |

| Ser | Lys | Ser | Cys | Val | Ser | Thr | Glu | Arg | Phe | Pro | Cys | Gly | Lys | Phe | Thr |
|---|---|---|---|---|---|---|---|---|---|---|---|---|---|---|---|
| | | | | 165 | | | | | 170 | | | | | 175 | |

| Gln | Gly | Arg | Ser | Arg | Arg | Trp | Ala | Ile | His | Thr | Ser | Glu | Asp | Ala | Leu |
|---|---|---|---|---|---|---|---|---|---|---|---|---|---|---|---|
| | | | 180 | | | | | 185 | | | | | 190 | | |

| Asp | Ala | Ser | Glu | Leu | Glu | His | Tyr | Asp | Pro | Ala | Asp | Leu | Ser | Pro | Thr |
|---|---|---|---|---|---|---|---|---|---|---|---|---|---|---|---|
| | | 195 | | | | | 200 | | | | | 205 | | | |

| Glu | Ser | Ser | Leu | Asp | Leu | Leu | Gly | Leu | Asn | Arg | Thr | Glu | Pro | Ser | Ala |
|---|---|---|---|---|---|---|---|---|---|---|---|---|---|---|---|
| 210 | | | | | 215 | | | | | 220 | | | | | |

| Gly | Glu | Asp | Gly | Ser | Gln | Val | Val | Arg | Ile | Val | Gly | Gly | Arg | Asp | Cys |
|---|---|---|---|---|---|---|---|---|---|---|---|---|---|---|---|
| 225 | | | | | 230 | | | | | 235 | | | | | 240 |

| Ala | Glu | Gly | Glu | Cys | Pro | Trp | Gln | Ala | Leu | Leu | Val | Asn | Glu | Glu | Asn |
|---|---|---|---|---|---|---|---|---|---|---|---|---|---|---|---|
| | | | | 245 | | | | | 250 | | | | | 255 | |

| Glu | Gly | Phe | Cys | Gly | Gly | Thr | Ile | Leu | Asn | Glu | Phe | Tyr | Val | Leu | Thr |
|---|---|---|---|---|---|---|---|---|---|---|---|---|---|---|---|
| | | | 260 | | | | | 265 | | | | | 270 | | |

| Ala | Ala | His | Cys | Leu | His | Gln | Ala | Lys | Arg | Phe | Thr | Val | Arg | Val | Gly |
|---|---|---|---|---|---|---|---|---|---|---|---|---|---|---|---|
| | | 275 | | | | | 280 | | | | | 285 | | | |

| Asp | Arg | Asn | Thr | Glu | Gln | Glu | Glu | Gly | Asn | Glu | Met | Ala | His | Glu | Val |
|---|---|---|---|---|---|---|---|---|---|---|---|---|---|---|---|
| | 290 | | | | | 295 | | | | | 300 | | | | |

| Glu | Met | Thr | Val | Lys | His | Ser | Arg | Phe | Val | Lys | Glu | Thr | Tyr | Asp | Phe |
|---|---|---|---|---|---|---|---|---|---|---|---|---|---|---|---|
| 305 | | | | | 310 | | | | | 315 | | | | | 320 |

| Asp | Ile | Ala | Val | Leu | Arg | Leu | Lys | Thr | Pro | Ile | Arg | Phe | Arg | Arg | Asn |
|---|---|---|---|---|---|---|---|---|---|---|---|---|---|---|---|
| | | | | 325 | | | | | 330 | | | | | 335 | |

| Val | Ala | Pro | Ala | Cys | Leu | Pro | Glu | Lys | Asp | Trp | Ala | Glu | Ala | Thr | Leu |
|---|---|---|---|---|---|---|---|---|---|---|---|---|---|---|---|
| | | | 340 | | | | | 345 | | | | | 350 | | |

| Met | Thr | Gln | Lys | Thr | Gly | Ile | Val | Ser | Gly | Phe | Gly | Arg | Thr | His | Glu |
|---|---|---|---|---|---|---|---|---|---|---|---|---|---|---|---|
| | | 355 | | | | | 360 | | | | | 365 | | | |

| Lys | Gly | Arg | Leu | Ser | Ser | Thr | Leu | Lys | Met | Leu | Glu | Val | Pro | Tyr | Val |
|---|---|---|---|---|---|---|---|---|---|---|---|---|---|---|---|
| | 370 | | | | | 375 | | | | | 380 | | | | |

| Asp | Arg | Ser | Thr | Cys | Lys | Leu | Ser | Ser | Ser | Phe | Thr | Ile | Thr | Pro | Asn |
|---|---|---|---|---|---|---|---|---|---|---|---|---|---|---|---|
| 385 | | | | | 390 | | | | | 395 | | | | | 400 |

|     |     |     |     |     |     |     |     |     |     |     |     |     |     |     |
| --- | --- | --- | --- | --- | --- | --- | --- | --- | --- | --- | --- | --- | --- | --- |
| Met | Phe | Cys | Ala | Gly<br>405 | Tyr | Asp | Thr | Gln | Pro<br>410 | Glu | Asp | Ala | Cys | Gln<br>415 | Gly |
| Asp | Ser | Gly | Gly<br>420 | Pro | His | Val | Thr | Arg<br>425 | Phe | Lys | Asp | Thr | Tyr<br>430 | Phe | Val |
| Thr | Gly | Ile | Val<br>435 | Ser | Trp | Gly | Glu<br>440 | Gly | Cys | Ala | Arg | Lys<br>445 | Gly | Lys | Phe |
| Gly | Val<br>450 | Tyr | Thr | Lys | Val | Ser<br>455 | Asn | Phe | Leu | Lys | Trp<br>460 | Ile | Asp | Lys | Ile |
| Met<br>465 | Lys | Ala | Arg | Ala | Gly<br>470 | Ala | Ala | Gly | Ser | Arg<br>475 | Gly | His | Ser | Glu | Ala<br>480 |
| Pro | Ala | Thr | Trp | Thr<br>485 | Val | Pro |

(2) INFORMATION FOR SEQ ID NO: 54:

(i) SEQUENCE CHARACTERISTICS:
      (A) LENGTH: 790 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO: 54:

|     |     |     |     |     |     |     |     |     |     |     |     |     |     |     |     |
| --- | --- | --- | --- | --- | --- | --- | --- | --- | --- | --- | --- | --- | --- | --- | --- |
| Glu<br>1 | Pro | Leu | Asp | Asp<br>5 | Tyr | Val | Asn | Thr | Gln<br>10 | Gly | Ala | Ser | Leu | Phe<br>15 | Ser |
| Val | Thr | Lys | Lys<br>20 | Gln | Leu | Gly | Ala | Gly<br>25 | Ser | Ile | Glu | Glu | Cys<br>30 | Ala | Ala |
| Lys | Cys | Glu<br>35 | Glu | Asp | Glu | Glu | Phe<br>40 | Thr | Cys | Arg | Ala | Phe<br>45 | Gln | Tyr | His |
| Ser | Lys<br>50 | Glu | Gln | Gln | Cys | Val<br>55 | Ile | Met | Ala | Glu | Asn<br>60 | Arg | Lys | Ser | Ser |
| Ile<br>65 | Ile | Arg | Met | Arg | Asp<br>70 | Val | Val | Leu | Phe | Glu<br>75 | Lys | Lys | Val | Tyr | Leu<br>80 |
| Ser | Glu | Cys | Lys | Thr<br>85 | Gly | Asn | Gly | Lys | Asn<br>90 | Tyr | Arg | Gly | Thr | Met<br>95 | Ser |
| Lys | Thr | Lys | Asn<br>100 | Gly | Ile | Thr | Cys | Gln<br>105 | Lys | Trp | Ser | Ser | Thr<br>110 | Ser | Pro |
| His | Arg | Pro<br>115 | Arg | Phe | Ser | Pro | Ala<br>120 | Thr | His | Pro | Ser | Glu<br>125 | Gly | Leu | Glu |
| Glu | Asn<br>130 | Tyr | Cys | Arg | Asn | Pro<br>135 | Asp | Asn | Asp | Pro | Gln<br>140 | Gly | Pro | Trp | Cys |
| Tyr<br>145 | Thr | Thr | Asp | Pro | Glu<br>150 | Lys | Arg | Tyr | Asp | Tyr<br>155 | Cys | Asp | Ile | Leu | Glu<br>160 |
| Cys | Glu | Glu | Glu | Cys<br>165 | Met | His | Cys | Ser | Gly<br>170 | Glu | Asn | Tyr | Asp | Gly<br>175 | Lys |
| Ile | Ser | Lys | Thr<br>180 | Met | Ser | Gly | Leu | Glu<br>185 | Cys | Gln | Ala | Trp | Asp<br>190 | Ser | Gln |
| Ser | Pro | His<br>195 | Ala | His | Gly | Tyr | Ile<br>200 | Pro | Ser | Lys | Phe | Pro<br>205 | Asn | Lys | Asn |
| Leu | Lys<br>210 | Lys | Asn | Tyr | Cys | Arg<br>215 | Asn | Pro | Asp | Arg | Glu<br>220 | Leu | Arg | Pro | Trp |
| Cys<br>225 | Phe | Thr | Thr | Asp | Pro<br>230 | Asn | Lys | Arg | Trp | Glu<br>235 | Leu | Cys | Asp | Ile | Pro<br>240 |
| Arg | Cys | Thr | Thr | Pro<br>245 | Pro | Pro | Ser | Ser | Gly<br>250 | Pro | Thr | Tyr | Gln | Cys<br>255 | Leu |
| Lys | Gly | Thr | Gly | Glu | Asn | Tyr | Arg | Gly | Asn | Val | Ala | Val | Thr | Val | Ser |

|     |     |     |     |     |     | 260 |     |     |     |     |     | 265 |     |     |     |     |     | 270 |     |     |
|-----|-----|-----|-----|-----|-----|-----|-----|-----|-----|-----|-----|-----|-----|-----|-----|-----|-----|-----|-----|-----|

Gly His Thr Cys Gln His Trp Ser Ala Gln Thr Pro His Thr His Asn
     275               280              285

Arg Thr Pro Glu Asn Phe Pro Cys Lys Asn Leu Asp Glu Asn Tyr Cys
290                 295              300

Arg Asn Pro Asp Gly Lys Arg Ala Pro Trp Cys His Thr Thr Asn Ser
305                 310              315              320

Gln Val Arg Trp Glu Tyr Cys Lys Ile Pro Ser Cys Asp Ser Ser Pro
             325              330              335

Val Ser Thr Glu Glu Leu Ala Pro Thr Ala Pro Pro Glu Leu Thr Pro
          340               345            350

Val Val Gln Asp Cys Tyr His Gly Asp Gly Gln Ser Tyr Arg Gly Thr
          355               360            365

Ser Ser Thr Thr Thr Thr Gly Lys Lys Cys Gln Ser Trp Ser Ser Met
     370               375              380

Thr Pro His Arg His Gln Lys Thr Pro Glu Asn Tyr Pro Asn Ala Gly
385                 390              395              400

Leu Thr Met Asn Tyr Cys Arg Asn Pro Asp Ala Asp Lys Gly Pro Trp
             405              410              415

Cys Phe Thr Thr Asp Pro Ser Val Arg Trp Glu Tyr Cys Asn Leu Lys
         420               425              430

Lys Cys Ser Gly Thr Glu Ala Ser Val Val Ala Pro Pro Pro Val Val
         435               440              445

Leu Leu Pro Asn Val Glu Thr Pro Ser Glu Glu Asp Cys Met Phe Gly
450                 455              460

Asn Gly Lys Gly Tyr Arg Gly Lys Arg Ala Thr Thr Val Thr Gly Thr
465                 470              475              480

Pro Cys Gln Asp Trp Ala Ala Gln Glu Pro His Arg His Ser Ile Phe
             485              490              495

Thr Pro Glu Thr Asn Pro Arg Ala Gly Leu Glu Lys Asn Tyr Cys Arg
          500             505              510

Asn Pro Asp Gly Asp Val Gly Gly Pro Trp Cys Tyr Thr Thr Asn Pro
         515               520              525

Arg Lys Leu Tyr Asp Tyr Cys Asp Val Pro Gln Cys Ala Ala Pro Ser
     530               535              540

Phe Asp Cys Gly Lys Pro Gln Val Glu Pro Lys Lys Cys Pro Gly Arg
545                 550              555              560

Val Val Gly Gly Cys Val Ala His Pro His Ser Trp Pro Trp Gln Val
             565              570              575

Ser Leu Arg Thr Arg Phe Gly Met His Phe Cys Gly Gly Thr Leu Ile
         580               585              590

Ser Pro Glu Trp Val Leu Thr Ala Ala His Cys Leu Glu Lys Ser Pro
         595               600              605

Arg Pro Ser Ser Tyr Lys Val Ile Leu Gly Ala His Gln Glu Val Asn
     610               615              620

Leu Glu Pro His Val Gln Glu Ile Glu Val Ser Arg Leu Phe Leu Glu
625                 630              635              640

Pro Thr Arg Lys Asp Ile Ala Leu Leu Lys Leu Ser Ser Pro Ala Val
             645              650              655

Ile Thr Asp Lys Val Ile Pro Ala Cys Leu Pro Ser Pro Asn Tyr Val
         660               665              670

Val Ala Asp Arg Thr Glu Cys Phe Ile Thr Gly Trp Gly Glu Thr Gln
         675               680              685

```
Gly Thr Phe Gly Ala Gly Leu Leu Lys Glu Ala Gln Leu Pro Val Ile
    690             695                 700

Glu Asn Lys Val Cys Asn Arg Tyr Glu Phe Leu Asn Gly Arg Val Gln
705                 710                 715                 720

Ser Thr Glu Leu Cys Ala Gly His Leu Ala Gly Gly Thr Asp Ser Cys
                725                 730                 735

Gln Gly Asp Ser Gly Gly Pro Leu Val Cys Phe Glu Lys Asp Lys Tyr
            740                 745                 750

Ile Leu Gln Gly Val Thr Ser Trp Gly Leu Gly Cys Ala Arg Pro Asn
        755                 760             765

Lys Pro Gly Val Tyr Val Arg Val Ser Arg Phe Val Thr Trp Ile Glu
    770                 775                 780

Gly Val Met Arg Asn Asn
785             790
```

( 2 ) INFORMATION FOR SEQ ID NO: 55:

( i ) SEQUENCE CHARACTERISTICS:
        ( A ) LENGTH: 153 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO: 55:

```
Val Tyr Leu Gln Thr Ser Leu Lys Tyr Asn Ile Leu Pro Glu Lys Glu
1               5                   10                  15

Glu Phe Pro Phe Ala Leu Gly Val Gln Thr Leu Pro Gln Thr Cys Asp
            20                  25                  30

Glu Pro Lys Ala His Thr Ser Phe Gln Ile Ser Leu Ser Val Ser Tyr
        35                  40                  45

Thr Gly Ser Arg Ser Ala Ser Asn Met Ala Ile Val Asp Val Lys Met
    50                  55                  60

Val Ser Gly Phe Ile Pro Leu Lys Pro Thr Val Lys Met Leu Glu Arg
65                  70                  75                  80

Ser Asn His Val Ser Arg Thr Glu Val Ser Ser Asn His Val Leu Ile
                85                  90                  95

Tyr Leu Asp Lys Val Ser Asn Gln Thr Leu Ser Leu Phe Phe Thr Val
            100                 105                 110

Leu Gln Asp Val Pro Val Arg Asp Leu Lys Pro Ala Ile Val Lys Val
        115                 120                 125

Tyr Asp Tyr Tyr Glu Thr Asp Glu Phe Ala Ile Ala Glu Tyr Asn Ala
    130                 135                 140

Pro Cys Ser Lys Asp Leu Gly Asn Ala
145                 150
```

( 2 ) INFORMATION FOR SEQ ID NO: 56:

( i ) SEQUENCE CHARACTERISTICS:
        ( A ) LENGTH: 202 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO: 56:

```
Met Glu Leu Trp Gly Ala Tyr Leu Leu Leu Cys Leu Phe Ser Leu Leu
1               5                   10                  15
```

```
Thr Gln Val Thr Thr Glu Pro Pro Thr Gln Lys Pro Lys Lys Ile Val
            20              25              30

Asn Ala Lys Lys Asp Val Val Asn Thr Lys Met Phe Glu Glu Leu Lys
        35              40              45

Ser Arg Leu Asp Thr Leu Ala Gln Glu Val Ala Leu Leu Lys Glu Gln
    50              55              60

Gln Ala Leu Gln Thr Val Cys Leu Lys Gly Thr Lys Val His Met Lys
65              70              75              80

Cys Phe Leu Ala Phe Thr Gln Thr Lys Thr Phe His Glu Ala Ser Glu
                85              90              95

Asp Cys Ile Ser Arg Gly Gly Thr Leu Ser Thr Pro Gln Thr Gly Ser
            100             105             110

Glu Asn Asp Ala Leu Tyr Glu Tyr Leu Arg Gln Ser Val Gly Asn Glu
        115             120             125

Ala Glu Ile Trp Leu Gly Leu Asn Asp Met Ala Ala Glu Gly Thr Trp
    130             135             140

Val Asp Met Thr Gly Ala Arg Ile Ala Tyr Lys Asn Trp Glu Thr Glu
145             150             155             160

Ile Thr Ala Gln Pro Asp Gly Gly Lys Thr Glu Asn Cys Ala Val Leu
                165             170             175

Ser Gly Ala Ala Asn Gly Lys Trp Phe Asp Lys Arg Cys Arg Asp Gln
            180             185             190

Leu Pro Tyr Ile Cys Gln Phe Gly Ile Val
        195             200
```

( 2 ) INFORMATION FOR SEQ ID NO: 57:

( i ) SEQUENCE CHARACTERISTICS:
        ( A ) LENGTH: 246 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO: 57:

```
Gln Val Lys Leu Gln Gln Ser Gly Ala Glu Leu Val Lys Pro Gly Ala
1               5               10              15

Ser Val Lys Met Ser Cys Lys Ala Ser Gly Tyr Thr Phe Ala Ser Tyr
            20              25              30

Trp Ile Asn Trp Val Lys Gln Arg Pro Gly Gln Gly Leu Glu Trp Ile
        35              40              45

Gly His Ile Tyr Pro Val Arg Ser Ile Thr Lys Tyr Asn Glu Lys Phe
    50              55              60

Lys Ser Lys Ala Thr Leu Thr Leu Asp Thr Ser Ser Ser Thr Ala Tyr
65              70              75              80

Met Gln Leu Ser Ser Leu Thr Ser Glu Asp Ser Ala Val Tyr Tyr Cys
                85              90              95

Ser Arg Gly Asp Gly Ser Asp Tyr Tyr Ala Met Asp Tyr Trp Gly Gln
            100             105             110

Gly Thr Thr Val Thr Val Ser Ser Gly Gly Gly Gly Ser Asp Ile Glu
        115             120             125

Leu Thr Gln Ser Pro Ala Ile Leu Ser Ala Ser Pro Gly Gly Lys Val
    130             135             140

Thr Met Thr Cys Arg Ala Ser Ser Ser Val Ser Tyr Met His Trp Tyr
145             150             155             160

Gln Gln Lys Pro Gly Ser Ser Pro Lys Pro Trp Ile Tyr Ala Thr Ser
```

-continued

```
                                    1 6 5                               1 7 0                                   1 7 5
        Asn  Leu  Ala  Ser  Gly  Val  Pro  Thr  Arg  Phe  Ser  Gly  Thr  Gly  Ser  Gly
                       1 8 0                      1 8 5                     1 9 0

Thr  Ser  Tyr  Ser  Leu  Thr  Ile  Ser  Arg  Val  Glu  Ala  Glu  Asp  Ala  Ala
                  1 9 5                      2 0 0                     2 0 5

Thr  Tyr  Tyr  Cys  Gln  Gln  Trp  Ser  Arg  Asn  Pro  Phe  Thr  Phe  Gly  Ser
             2 1 0                      2 1 5                     2 2 0

Gly  Thr  Lys  Leu  Glu  Ile  Lys  Arg  Ala  Ala  Ala  Glu  Gln  Lys  Leu  Ile
        2 2 5                      2 3 0                     2 3 5                     2 4 0

Ser  Glu  Glu  Asp  Leu  Asn
                            2 4 5
```

( 2 ) INFORMATION FOR SEQ ID NO: 58:

( i ) SEQUENCE CHARACTERISTICS:
    ( A ) LENGTH: 101 amino acids
    ( B ) TYPE: amino acid
    ( C ) STRANDEDNESS:
    ( D ) TOPOLOGY: linear ( i i ) MOLECULE TYPE: protein ( x i ) SEQUENCE DESCRIPTION: SEQ ID NO: 58:

```
        Met  Ser  Asn  Thr  Gln  Ala  Glu  Arg  Ser  Ile  Ile  Gly  Met  Ile  Asp  Met
        1                   5                        1 0                     1 5

Phe  His  Lys  Tyr  Thr  Arg  Arg  Asp  Asp  Lys  Ile  Asp  Lys  Pro  Ser  Leu
                       2 0                       2 5                     3 0

Leu  Thr  Met  Met  Lys  Glu  Asn  Phe  Pro  Asn  Phe  Leu  Ser  Ala  Cys  Asp
                  3 5                       4 0                     4 5

Lys  Lys  Gly  Thr  Asn  Tyr  Leu  Ala  Asp  Val  Phe  Glu  Lys  Lys  Asp  Lys
             5 0                       5 5                     6 0

Asn  Glu  Asp  Lys  Lys  Ile  Asp  Phe  Ser  Glu  Phe  Leu  Ser  Leu  Leu  Gly
        6 5                       7 0                     7 5                     8 0

Asp  Ile  Ala  Thr  Asp  Tyr  His  Lys  Gln  Ser  His  Gly  Ala  Ala  Pro  Cys
                            8 5                       9 0                     9 5

Ser  Gly  Gly  Ser  Gln
                       1 0 0
```